United States Patent
Baker et al.

(10) Patent No.: US 7,676,384 B2
(45) Date of Patent: Mar. 9, 2010

(54) SYSTEM AND METHOD FOR THE AUTOMATED PRESENTATION OF SYSTEM DATA TO, AND INTERACTION WITH, A COMPUTER MAINTAINED DATABASE

(75) Inventors: Sidney M. Baker, Weston, CT (US); Miles K. Thompson, Wellington (NZ); Satheesh Ramachandran, Austin, TX (US)

(73) Assignee: Medigenesis, Inc., Stamford, CT (US)

( * ) Notice: Subject to any disclaimer, the term of this patent is extended or adjusted under 35 U.S.C. 154(b) by 1269 days.

(21) Appl. No.: 09/765,714

(22) Filed: Jan. 18, 2001

(65) Prior Publication Data

US 2003/0061072 A1     Mar. 27, 2003

Related U.S. Application Data

(60) Provisional application No. 60/176,535, filed on Jan. 18, 2000, provisional application No. 60/233,041, filed on Sep. 15, 2000.

(51) Int. Cl.
    *G06F 17/60* (2006.01)
(52) U.S. Cl. ............ 705/3; 705/2; 707/5; 600/300
(58) Field of Classification Search ............ 705/2–3; 435/6; 707/3, 101; 702/19
    See application file for complete search history.

(56) References Cited

U.S. PATENT DOCUMENTS

| | | | |
|---|---|---|---|
| 5,724,571 A * | 3/1998 | Woods | 707/5 |
| 5,915,240 A * | 6/1999 | Karpf | 705/2 |
| 5,924,074 A * | 7/1999 | Evans | 705/3 |
| 6,424,996 B1 * | 7/2002 | Killcommons et al. | 709/206 |
| 6,446,061 B1 * | 9/2002 | Doerre et al. | 707/3 |
| 6,463,430 B1 * | 10/2002 | Brady et al. | 707/3 |
| 6,484,166 B1 * | 11/2002 | Maynard | 707/5 |
| 6,684,188 B1 * | 1/2004 | Mitchell et al. | 705/3 |

(Continued)

OTHER PUBLICATIONS

Constantinos Pattichis; Neural Network Models in EMG Diagnosis; May 5, 1995; pp. 1-11.*

(Continued)

*Primary Examiner*—Vanel Frenel
(74) *Attorney, Agent, or Firm*—Kramer Levin Naftalis & Frankel LLP; Aaron Haleva, Esq.

(57) ABSTRACT

A system and method are provided for extracting a set of data from a system user descriptive of the complete health snapshot of the user's to interact with a database of numerous other users so as to generate a cluster of similar user's exhibiting a similar (within some system defined distance metric) health snapshot. The system guides the user to present his or her data via a complex questionnaire based upon a novel descriptive taxonomy, based upon the principles of "cyberhealth" as opposed to the standard medical "disease oriented" singular cause and effect model. The system generates the cluster of similar users, analyzes the cluster to obtain a ranked list of possible remedies or therapies to assist the user in dealing with health problems. The system further creates a computer networked virtual community of users with common health problems/interests, facilitates online chat, discussion groups, and the trading of health information. Additionally, the system provides listings of and links to health care providers and medical testing laboratories who are able to assist users of the system.

21 Claims, 57 Drawing Sheets

U.S. PATENT DOCUMENTS

| | | | | |
|---|---|---|---|---|
| 6,780,589 B1* | 8/2004 | Gulati | ............................ | 435/6 |
| 6,804,661 B2* | 10/2004 | Cook | ............................ | 706/20 |
| 2002/0065682 A1* | 5/2002 | Goldenberg | .................... | 705/2 |
| 2005/0005266 A1* | 1/2005 | Datig | ........................... | 717/136 |
| 2005/0165285 A1* | 7/2005 | Iliff | ............................ | 600/300 |

OTHER PUBLICATIONS

Pattichis (Neural Network Models in EMG Diagnosis; May 5, 1995).*

Elsevier Computer Methods and Programs in Biomedicine 54 (1997) 115-122; Automatic SNOMED classification-a corpus-based method by (.M. de Bruijn a, A. Hasman a, J.W. Arends b; 1997).*

David K.Y. Chiu and A.K.C. Wong, "An Event-Covering Approach for Cluster Analysis of Discrete-Valued Data with Application to Medical Diagnosis" The First Conference on Artificial Intelligence Applications, IEEE Computer Society (1984).

Dario Lucarella, "A document retrieval system based on nearest neighbour searching" Journal of Information Science 14 (1988), pp. 25-33.

W. John Wilbur, "Retrieval Testing by the Comparison of Statistically Independent Retrieval Methods" Journal of the American Society for Information Science 43(5) (1992), pp. 358-370.

LI.M. de Bruijn, A. Hasman, J.W. Arends, "Automatic SNOMED classifaction-a corpus-based method" Computer Methods and Programs in Biomedicine 54 (1997), pp. 115-122.

Leah S. Larkey and W. Bruce Croft, "Combining Classifiers in Text Categorization" Proceedings of the 19th Annual Inernational ACM SIGIR Conference on Research and Development in Information Retrieval (1996), pp. 289-297.

Jochen Bernauer, M.D., "A Controlled Vocabulary Framework for Report Generation in Bone-Scintigraphy" Fourteenth Annual Symposium on Computer Applications in Medical Care (1990), pp. 195-199.

* cited by examiner

PDV VECTOR

| Gender | Age | | | | | | | | | | | | | | | SFWs | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| 1 | 2 | | | | | | | | | | | | | | | | | | | | | | | | | | | | | | | | ... |

What is Medigenesis?

EDUCATE  ENABLE  EMPOWER

You are chatting with an old friend at a party. After catching up on the latest baseball scores, your progress on that big account at work, and the new recipe you tried last week for pasta primavera, you mention that you're worried about your oldest son. He's 14 years old, has developed acne and his eczema has gotten worse, too. He's really self-conscious-you know how kids are at that age. Maybe that accounts for why he's been getting such terrible stomachaches and headaches lately. The doctor wants to start him on antibiotics for the acne. You hate the thought of him taking that stuff but what else can you do? That's funny, says your friend, because his cousin's 13 year old had really similar problems and it turned out that he had developed an allergy to milk products. Can you believe that? Simply by

*did you know...?* M and M's were developed so that soldiers could eat candy without getting their fingers sticky.

Security and Privacy

At Medigenesis we value our members' security and privacy as our own. We believe that the success of our services will be substantially affected by the quality of our security and our commitment to your privacy.

Take the time to review this policy in its entirety. Medigenesis, Inc. is the entity collecting information on this site. If you have any questions or concerns, please email us at the following address: info@medigenesis.com. If you would like to reference a particular section please click on one of the following section headings:

- Site Security
- Information Collection and Use
- Children's Privacy
- Discussion Groups
- Account Sign-up
- Credit Card Processing Procedure
- Cookies
- Log Files
- Sharing of Information
- Links
- Administrative Access to Data
- Data Backups
- Site and Service Updates
- Correction/Updating Personal Information
- Leaving our Community
- Notification of Changes Site Security We have taken substantial precautions for security. Our site uses encryption (SSL) for all data that travels from you to our web site.

Our Public Keys, are provided by Verisign, a leading provider of Internet Trust Services.

You may select to use either 40 bit encryption or 128 bit encryption with our site. For the utmost in data security you should acquire 128 bit browser encryption software.

We employ an electronic firewall system and secured servers. We monitor these systems at all times.

All of our equipment is physically stored in secured areas, protected 24 x7 by guards, and logged security cameras. Access to these areas is limited and logged.

Information Collection and Use

Approximately three months after our site has undergone beta testing, we will officially launch Medigenesis.com. After the official launch, we will produce revenue from member subscriptions. We do not sell, assign, transfer or share mailing lists or personally identifiable data about our members except as described in this privacy policy. In fact, when you sign-up for our site, we don't ask you for a mailing address. Even using your name is optional. Note that if you choose to provide personally identifiable

FIG. 3A information to us, like your name or mailing address, that information will be available to our staff and can be linked to other information collected by us as to your use of our site. The information you provide to us is subject to disclosure pursuant to judicial or other government subpoenas, warrants or orders.

It is possible at some time in the future that you will be able to ask us to provide your data to a physician or researcher. If we provide this service, it will only be carried out at your request.

Our site is about health and wellness. We will ask you many questions regarding your health and how you are going about achieving good health. We store the data in our database, but it is only connected with the email address that you provide to us.

We do plan on providing aggregated data to the research community in order to further the cause of good health throughout the world and to others. This aggregated data never contains personally identifiable information.

Children's Privacy

We expect that parents will use our site for their children or with their children. Information provided about children must be entered with parental consent. If we find that we have inadvertently collected personally identifiable information from a child under the age of 16, we will immediately delete that information and will not share that information with any third party. Our site has a discussion group area where members can post messages and anyone on the Internet can read them. It is the parent's responsibility to monitor any messages that their children may post. We believe that members should never post addresses or phone numbers in our discussion area. Except as specifically provided in this privacy policy, information about children is cared for in the same way as all of our members.

Discussion groups

Our site has a discussion group area where members can post messages and anyone on the Internet can read them. Members should not post information here that they do not want to be accessible by anyone on the Internet. We believe that members should never post addresses or phone numbers in our discussion area.

Account Sign-up

In order to use this site, a user must first complete the sign-up form. During sign-up a user is required to give only his or her sex, age, email address, and country. Optionally you may provide your name, title, and zip code.

We have designed our site for you to remain truly anonymous if you wish. We use a site alias to refer to members on the site, not your name or social security number. You can utilize a third party mail provider such as Yahoo or Hotmail for our email contact requirement again enabling you to remain anonymous.

Credit Card Processing Procedure

Medigenesis has engaged a credit card payment processor ('Payment Processor') for credit card billing and payment information obtained through this Site. The Payment Processor directly obtains and verifies the payment information and charges your credit card for the services you designate. Medigenesis is notified only via your member alias if your card has been approved or declined. Medigenesis does not receive or store your name, credit card number or billing address. The Payment Processor has agreed to keep all of your personal information confidential.

Cookies

A cookie is a piece of data stored on your hard drive that we use to track your movement while you browse our site. Cookies are required to enable advanced system redundancy and so we can identify your data to your member alias when we write your data to our database.

Our cookies are not persistent. We create a cookie when you log-on. The cookie becomes useless when you choose to log-off.

Our site will not work properly if you choose to reject our cookies.

Log Files

We use IP addresses to determine which parts of our site are most popular and to administer the site. IP addresses are not linked to personally identifiable information.

We also log all data transactions both to disk and write-once media. This ensures that we have an indisputable record of information provided to us by our members. This information is solely kept for security measures and will never be sold or distributed in any way linked to you.

Sharing of information

We plan on providing aggregated data to the research community in order to further the cause of good health throughout the world and to others. This aggregated data never contains personally identifiable information.

FIG. 3B

We do provide links to organizations and companies that we believe may be interesting to our users. We provide these organizations and companies with no information about you or what you do on our site. Any information they require to fulfill your needs must come from you.

Some laboratories will electronically transfer your lab data to us if you so desire. Again you must provide the laboratory with your Medigenesis Member Alias in order to facilitate this transfer of information.

Links

Medigenesis provides links to other sites. Please be aware that we are not responsible for the privacy practices of such other sites. We encourage our users to be aware when they leave our site and to read the privacy statements of each and every web site that collects personally identifiable information. This privacy statement applies solely to information collected by this web site.

Administrative Access to Data

It is of course necessary for our staff and persons who provide services to us to work with the data in our databases. Whenever this work is performed security is always kept in mind. We perform all of our work either locally on our systems directly or over a Virtual Private Network using encryption technology, if performed from remote locations. All access to data is controlled via passwords and all access is logged.

Data Backups

The data in our database are extremely valuable to our community, and we therefore make copies of this data on a regular basis. We take extreme caution with our backup tapes and CDs. The media is kept locked away at all times except when it is in transit from one location to another.

Site and Service Updates

We may send you site and service announcement updates. Members are not able to un-subscribe from service announcements, which contain important information about the service. We communicate with you to provide requested services and in regards to issues relating to your account via email or phone if you provide us with your phone number along with your service request.

Correction/Updating Personal Information:

If your personally identifiable information changes (such as your zip code) we will endeavor to provide a way to correct, update or remove the personal data you have provided to us. This can usually be done at the member details page or by emailing our Customer Support at info@medigenesis.com.

Leaving our Community

If you no longer desire our service we would like to keep your data in our database so we can use it to help the other members of our community. Remember that your data is only identified to your member alias. If you feel strongly that your data should be removed from our database, please write a letter to our customer service department asking for your data to be removed, and we will endeavor to remove all the data stored using your member alias.

Notification of Changes

If we decide to change our privacy policy, we will post those changes on our 'What's News' page so our users are always aware of what information we collect, how we use it, and under circumstances, if any, we disclose it. If at any point we decide to use personally identifiable information in a manner different from that stated at the time it was collected, we will notify users by way of an email. Users will have a choice as to whether or not we use their information in this different manner. We will use information in accordance with the version of the privacy policy under which the information was collected. To make it easier for you to determine, we post at the top of the policy the last date that the policy was revised.

FIG. 3C

New Member Information

Create Member Alias: _____ (member aliases must not exceed 12 characters, and must be all letters and/or digits)

Create Password: _____

Reenter Password: _____ (password must be at least 4 characters)

Current Email Address: _____

Your Title: [Select ▼]

First Name: _____

Last Name: _____

Your Zip Code: _____

Country of Residence: [United States ▼]

Your Birthday: [Month ▼] [Day ▼] [Year ▼]

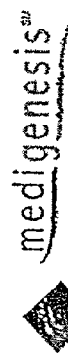

FIG. 7A medigenesis℠
*a new beginning in medicine* did you know...? Your stomach has to produce a new layer of mucus every two weeks otherwise it will digest itself.

laboratory directory

Provider Directory > Laboratory Directory

These labs can provide you with testing kits for issues such as immune dysfunctions, food allergies and environmental allergies. Please contact the lab directly for ordering and testing instructions.

A.A.L. Reference Laboratories, Inc.
1715 E. Wilshire, Ste. 715
Santa Ana, CA 92705
(800) 522-2611 - Phone
(714) 534-2034 - Fax
www.aalrl.com
Specializing in Immune Disease testing, Cardiac Risk Assessment testing, Anti-aging programs and Hormone replacement studies.

Great Plains Laboratory, Inc.
9335 W. 75 St.
Overland Park, KS 66204
(913) 341-8949 - Phone
(913) 341-6207 - Fax
gpl4u@aol.com
Specializing in testing for Autism, Developmental Disorders, and Related Conditions.

Great Smokies Laboratory
63 Zillicoa Street
Asheville, NC 28801-1074
(800) 522-4762 - Phone
(828) 252-9303 - Fax
www.gsdl.com
Specializing in Comprehensive Functional Assessments.

Immuno Laboratories
1620 West Oakland Park Boulevard
Fort Lauderdale, FL 33311
(800) 231-9197 - Phone
(954) 739-6563
www.betterhealthusa.com
Specializing in Food and Environmental Testing Return to the Provider Directory >>

medigenesis℠
*a new beginning in medicine*

*The average person falls asleep in seven minutes.*
did you know...?

library directory

Provider Directory > Library Directory

These web sites and resources will provide you with quality general health care information, and access to extensive information about many diseases and conditions.

www.medlineplus.gov
Provides information from the National Library of Medicine at the National Institutes of Health. Also provides links to dictionaries, lists of hospitals and physicians, health information in Spanish and other languages, and clinical trials.

www.os.dhhs.gov
Web site of the US Department of health and Human Services.

www.nih.gov
Web site of The National Institutes of Health.

igm.nlm.nih.gov
Provides assisted searching of 15 of the National Library of Medicine's databases.

www.library.tmc.edu
The Houston Academy of Medicine - Texas Medical Center Library provides many links to medical information on the local, state and national levels. It features an entire section dedicated to consumers and non-professionals.

Return to the Provider Directory >>

FIG. 7B

medigenesis℠
*a new beginning in medicine*

*did you know...?*
Every time you lick a stamp, you're consuming 1/10 of a calorie.

discussion

The Discussion area allows our members to discuss health issues with the entire Medigenesis community. Medigenesis creates groups based on health areas that we feel will be of interest to the community. If you have an idea for a group but don't see it on the list, please contact us and request that we add it.

Both members and visitors to the site can read the messages in a group. To post a message to a group you must subscribe to the group.

Please select one of the following options to access a discussion area.

| my recommended groups | my subscribed groups |
|---|---|
| Browse our group recommendations for you. This is a great place to start if you're not sure what to do. | Browse the groups you have subscribed to. This is the first step to posting you own messages. | message search
*Coming soon.* Search for messages of interest to you and your family. By doing this, you'll find interesting information from the community for your problems.

FIG. 9A medigenesis℠
a new beginning in medicine

*did you know...?*
Every time you lick a stamp, you're consuming 1/10 of a calorie.

member homepage

Hello rebecca and welcome to your homepage. Please choose from the options below.

your health profile [go]
This page is the command center of the site. Go here first to enter all your personal health information. That will be the basis for our database and recommendations. Then, go here periodically to update your information and see how you are achieving your health goals.

progress report [go]
This report illustrates how all of your reported problems have been affected by our advice as well as any treatments you have subscribed to on your own.

medical summary [go]
This report is the culmination of all your effort. It reports all of your problems, treatments, and diagnostic results along with your health options and supporting research.

member details [go]
Go here to modify some of the personal information that you have provided for the Medigenesis site. You may change any of your personal information except your member alias.

my recommended groups [go]

my subscribed groups [go]

Oh-no! You have come to our help page. Well please relax and we will try to help you find the guidance you need. This section is divided into several areas based on the tasks for which we think members will need help. You may find the help you're looking for by selecting one of the following sections or scrolling through this page.

- I'm confused about everything I should do to get the most out of the site.
- What is the "your health profile" all about?
- I want to add a problem but I can't find it in the "add a problem" page.
- I want to add a treatment but I can't find it in the "add a treatment" page.
- I really think there should be a discussion group about...
- Why should I update my problem severity?
- Why should I update my treatment information?
- How can I enter information for my child?
- What is the Medical Summary all about?
- How can I see my progress?
- What is required to sign up for Medigenesis?

I want to add a problem but I cant find it in the "add a problem" page

We have attempted to make the problem entry pages as easy as possible to navigate through. If you can't find a problem you are having, you should first try to take the questionnaire. During the questionnaire you will be adding many *secondary problems to your health profile*. You may find that the problem you are looking for is in this list. If it is, you can promote it to your *primary problem* list from within the *manage secondary problems page*, which is accessible from *your health profile*.

When you choose to promote a secondary problem we will prompt you to enter a "rating" for this problem. This is the same rating that you gave us for primary problems. Rating tell us how important this problem is to you on a scale from 1 to 10 where 1 is highest importance and 10 is lowest importance. Problems can have the same rating if you consider them to be of equal importance in the sense of what bothers you the most in your life. A mild problem may be #1 on your list depending on circumstances. For example mild acne may be rated highly if you are a model!

If after taking the questionnaire you still need a problem added to the system, please send an email describing your problem in detail to: problem.request@medigenesis.com by clicking on this link. We will process your request as quickly as possible and reply with a message explaining what you should do to add your problem.

I want to add a treatment but I can't find it in the "add a treatment" page

We have attempted to make treatment entry as easy as possible for our members. We offer both list and search functions to find a treatment. If you have tried unsuccessfully to find your treatment using both of these methods, then send a detailed message to the following address treatment.request@medigenesis.com by clicking on this link.

I'm confused about everything I should do to get the most out of the site

There are two sections of the site that require member participation to get the most out of your experience, the discussion and your health profile.

FIG. 26

Discussion

You can access your discussion groups by clicking on the discussion group icon. There you will find the list of groups we think you will be interested in.

In the discussion area you may view messages in any group but you must subscribe to a group in order to post a message. Once you have subscribed to a group it will always appear in your *subscribed group* list. You may also unsubscribe from a group in order to remove it from your *subscribed group* list.

Soon we will be adding a message search feature. From this search you will be able to find items in groups that may be of interest to you and groups that you may want to subscribe to.

If you have a good idea for a group that we have not added, you can request that we add it by sending an email explaining your reasoning to group.request@medigenesis.com .

Your Health Profile

This page is the command center of the site. From here you enter and update all the information that enables us to provide the information that will help you achieve better health.

The page is laid out in six sections.

1. Member information
2. Treatments
3. Primary Problems
4. Questionnaire/Secondary Problems - Other Attributes
5. Medical Summary Reports
6. Diagnostic Tests The first time you use your *health profile* you should fill out these sections in order. There is a lot of information to provide but you can do this at your own pace. In each section you can enter information, quit when you want and come back to the task at any later date.

This information will be used to match you with others in the community in order to provide you with options that may help you achieve your goal of better health. You of course only have to give the information that you are comfortable providing. However, the more information we have about your problems and treatments the better we will be able to provide options for achieving your goals.

Member Information

In this section we will get information about your height, weight.

FIG. 27

Treatments

In the treatments section we will ask you to tell us what treatments you are following. And then how the severity of your problems is made better or worse by the set of your treatments. We believe that there are many different types of treatments that may benefit your health. We want you to tell us about all the things you do or take to try and solve your problems. You can also tell us both a good response and bad response to your treatments.

In order to update your treatments you should select update from the manage treatments page. If you set an end date on the treatment we will know that you are no longer taking it and move it to your inactive treatments list.

This information will be one of the cornerstones of our community. As we grow we will have more and more information about which treatments work to help our members achieve better health. That information from our community will then be used by all our members to help themselves.

If you have a question about adding a treatment click here.

Primary Problems

In this section you will tell Medigenesis about the problems that you feel most affect your health. These problems are the things you tell your family and friends when they say "How are you feeling lately" and the answer may be "well I keep getting these annoying headaches", "for some reason I always have a really upset stomach", or "I feel really light headed all the time". They are also the symptoms, life events, worries or changes that you would tell a specialist, family doctor, or other health professional when he or she asks "what seems to be the matter?"

We want you to tell us about, as many of these problems as you feel are important. We will also ask you in the questionnaire about things that may be affecting your health to a lesser degree.

Entering Problems

You enter your problems using our problem entry page which is accessed from the manage problems page. It is critical for us to let you choose problems using the language you are comfortable with while maintaining the integrity of our database that will be used to provide health data to the community.

Therefore we don't allow you to just enter your problems in text form. We have a large list of problems stored with the terms you are used to calling them. During problem entry you will select these terms from our problem entry page. The problem entry page uses a body metaphor to make it easier for you to find the problems as we have defined them. You select problems by first choosing the part of the body where you are experiencing the problem. For instance for a headache you would click on the head in the problem entry figure. There are many body areas available on the figure. As you move your mouse over each area a hint box will appear to let you know which area you are over. You may want to hunt around a little to become familiar with the areas.

Once you have clicked on an area the right frame of the page will be populated with the sub-areas of the body area that you have chosen. These are listed in the list labeled Area. For instance, if you select head you will see eyes, nose, and mouth amongst others in the Area list.

Next to the Area list is the problem section where problems are listed for you to choose from. When you first select a body area we will fill this problem list with the

FIG. 28 top 20 problems for that body area as listed in our database. This should make it easier for you to select one of the top 20 problems.

If your problem is not in that list you may then select a problem area, for instance eyes in our example. When you click on eyes, all of the problems that affect eyes from our database are listed in the problem list. You may then scroll through the list to find the problem you are trying to add.

You may also remove a problem from the *Your Chosen Problem List* by just clicking on the problem.

You have probably also noted that there are many words around the figure. These are for areas that don't easily map to the body. For instance pain or balance. Some of these words give you a way of entering information about problems that don't have a recognizable location in the body (life events, emotions, balance). Others provide an alternative way of finding problems that you could also get to by clicking on the body part, such as pain and itching. You may experiment to find, for example, that for elbow pain clicking on pain will get you a much bigger list to start from than if you start by clicking on elbow.

Feedback (Incomplete Primary Problems)

After you add your problems you will be brought back to the manage primary problems page. Here we will ask you for some critical information about your primary problems. Until you provide this information these problems are considered incomplete.

The information we will ask you for is as follows:

> Rating: How important to you is this problem on a scale from 1 to 10 where 1 is highest importance and 10 is lowest importance. Problems can have the same rating if you consider them to be of equal importance in the sense of what bothers you the most in your life. A mild problem may be #1 on your list depending on circumstances. For example mild acne may be rated highly if you are a model! This rating is different from severity. For example, acne may be the problem you most want to get rid of and you may rate it as a 2, even though its severity, as judged by how bad acne can sometimes be, is mild.
>
> Frequency: How often does the problem occur? We have tried to supply any answer that you would need for frequency.
>
> Severity: When the problem happens how would you characterize its severity. The choices are mild, moderate, severe or variable. We do not attempt to define severity for you, but leave it to you to give us your best judgment as to how severe the problem usually tends to be when it occurs. Generally speaking a severe problem interferes significantly with normal activities and or sleep and a mild problem does not. Moderate is in between...
>
> Onset Date: When did this problem first start? There are two ways that you can fill out this information. You can enter x days/weeks/months/years ago where x can be from 1 to 12 or you can select from the list of text answers for instance in twenties or in thirties.

When you have entered this information for all your incomplete problems you should press the update button. This will add all of these problems to your primary problem list. Once on your primary list they should never be deleted unless you added the problem by mistake. See the next section to learn about how to say that a problem is no longer bothering you and thus moving it to your inactive primary problem list. We need to keep all problems in the database so we can help others with similar problems.

FIG. 29

Once you have added all of our primary problems you may then go on to the Medigenesis questionnaire.

Updating Problem Severity

Periodically you will need to update the severity of your problems. This information is used to create your *progress report*, which is used to give you a concise listing of how your problems are being affected by your treatments.

You update severity using the *manage primary problems* page. Severity in this instance is slightly different from the initial severity we asked you for when adding a problem. Here we want you to give us a number from 0 to 12 that relates your overall feelings about this particular problem. Everything you feel about it all rolled in to one number. 1 means that it is not much of a problem any more, 12 means that it is a serious, incapacitating problem in your life that is not getting any better. If you set the severity to 0 it means that the problem has gone away and we should move it to your inactive problem list.

Secondary Problems/Other Attributes (Questionnaire)

Secondary Problems and Other Attributes are created by answers to our comprehensive questionnaire. The questionnaire will ask you many questions about your health and health history. You can leave the questionnaire at any time and save all the answers you have made to that point. All of the questions require some answer, quite often a yes or no but also things like frequency, severity, onset, duration of episode, and end date. You may be asked if some things aggravate or alleviate certain problems.

We may also ask you to provide information on critical lab tests that you may have taken. We will attempt to make it easy for you to fill in the lab test results.

We will attempt to make this process as interesting as possible. It is important to keep in mind that after you have completed the information required for these pages you will have a comprehensive blueprint of your health profile that you can share with your medical practitioners, plus all the benefits of the recommendations of our community. So hang in there, it's worth all the effort.

Once you have taken the questionnaire there should be no reason to take it again unless there are major changes to your health. If you do take the questionnaire again we will make answering the questions a second time easier by including your original answers as the defaults if possible to all the answers.

Periodically you should update the severity of your secondary problems as you do for primary problems. If you set your secondary problem severity to zero, then the problem will move to the inactive secondary problem list.

Medical Summary Reports

FIG. 30

The medical summary report is the culmination of all this effort. It reports all of your problems, treatments, and diagnostic results. It also gives you health options designated by our staff based on the experiences of our community and important discoveries and knowledge of current practices in medicine.

With this report you will be able to find or go to a Physician or Medical Practitioner empowered with both your health profile and many options that you may wish to consider, based on the experiences of our community, to achieve your goal of better health.

You may run a medical summary report at any time. This report uses all the current information we have on file for you in our database. The reports are stored so that you can access old or new reports at any time.

Diagnostic Tests

In your medical summary report we may report options for lab testing based on the experience of groups of individuals with profiles of problems like yours. The results of such tests may place you more accurately in a group with more specific options. For example if you are in a cluster in which troublesome digestive problems are an issue our database can be more helpful to you if it includes the results of a test for intestinal parasites.

We also may offer a list of Laboratories where the test is not only provided but the results will be automatically forwarded to Medigenesis electronically and added into your profile. These labs have been chosen due to their quality standards and their ability to electronically interact with our database. We receive no remuneration from any of these organizations.

In the *manage diagnostic tests* page we will show you any of the recommended tests that we have not received results for along with the results of all the tests you have told us about. You will have the ability to tell us that you are not planning on taking one of the recommended lab tests.

Entering Information for another member

We expect that quite often a parent or guardian will be the one entering information for their charge. Each member requires their own account. In order to enter information for a particular member you must simply login to the site as that member. On the bottom navigation bar there is a link to both logout and login to the site. So to switch between two accounts you would just click logout, then click login where a page would prompt you for your Alias and password. We may periodically prompt the user to determine what your relationship is to the member so that we know who was giving us the information.

Progress Report

This report illustrates how all of your reported problems have been affected by, the advice of our community and any treatments you have subscribed to on your own. Information will only appear on this report if you periodically update your problems and treatments. Apart from giving you an accurate way of accounting for your progress or lack of it over time - a very valuable

FIG. 31 document for you and your health care providers - the progress report helps the community of Medigenesis users by providing outcome information linked to the treatment options you and your physician have chosen and the problem profile you started with. That is to say that many of us, when we have a good or bad response to a particular kind of treatment, want to "tell the world." Medigenesis gives you a way of doing just that!

The progress report may be run and printed at any time. It will show the latest information pertaining to your problems, treatments and diagnostic tests. It is an excellent aid for communicating your current and past conditions to your medical practitioner.

Medigenesis Sign-up

The sign-up process for our "soft launch" is very easy. You will need to supply an Alias, a password, country, birth date, email account, and gender. You may provide a title, first and last name. If you provide your name you will be able to use it for messages posted to a discussion group. If you do not provide your name you will only be able to post messages as your member alias or anonymous.

For the utmost in anonymity you should use a third party email provider such as Yahoo or Hotmail with say your alias as the address. Then give us this anonymous account to use for our communications.

If you use this option you should probably use a very unusual Alias to sign up for our site so that you will be likely to obtain that same alias from the email vendor. Of course you can use any name for your email address so this is not a requirement.

If you are interested in obtaining an anonymous email address follow one of these links. Medigenesis has no relationship with either of these email providers and you can be assured that we have no way to link your real credentials to the email account you provide to us.

www.hotmail.com where you can read more or select New User - Signup Now in the upper right of the page.

http://mail.yahoo.com Again you can read more to find out about this email provider or select Sign Me Up in the top left of the page.

Once you have established your account you are ready to sign-up for Medigenesis anonymously.

FIG. 32

a new beginning in medicine your health profile

Return to: Member Home Page > Your Health Profile

Welcome to Your Health Profile where you may create a detailed well-organized portrait of your health problems. Follow the numbered steps below. You may return here at any time to update your profile.

— 3401

1. • Member Information [go!]
Your height and weight information

2. • Treatments [go!]
Share the effectiveness of the treatments you are following.

3. • Primary Problems [go!]
Tell us about the problems that you feel most affect your health.

4. • Secondary Problems and Other Attributes [go!]
These problems are created from your answers to our questionnaire.

5. • Medical Summary [go!]
This report is the result of all of the profile information you have given us.

6. • Diagnostic Tests [go!]
A listing of the lab tests that you have told us about.

FIG. 34 member information
member information

Return to: Member Home Page > Your Health Profile > Member Information

Go to:  | 1. Member Information | go |

Please select Manage > to update your Height and Weight.

Member Information

Age: 3
Gender: male
Height: 3' 5"
Weight: 51 lbs

Manage member information >>

medigenesis℠
a new beginning in medicine treatments

Go to: 1. Member Information [go]

Return to: Member Home Page > Your Health Profile > Treatments

Treatments

These are the treatments that you have told us you are following. If any of this information has changed or if you have additional comments to make about your treatments please click on "manage treatments>" below. If you are taking a new treatment please add it to the list buy going to the "add treatment>" page.

| Name | | Approximate Start Date | Approximate End Date | Following |
|---|---|---|---|---|
| Nystatin | 1 tsp. Teaspoon 4 x Daily | 8th November 2000 | | As stated |
| Cod Liver Oil | | 10th November 2000 | | As stated |
| Milk free diet | | 15th October 2000 | | As stated |
| Yeast free diet | | 8th November 2000 | | As stated |

Add treatment >>
Manage treatments >>

FIG. 36

3. Primary Problems

Please review the primary problems you have listed below. You may add a new problem to your list at any time by clicking the add> button below. You should also periodically select manage> in order to update how you are feeling about each problem.

Active Problems:

| Problem Name | Rating | How Often | Started When | Initial Severity | Latest Severity |
|---|---|---|---|---|---|
| Elbow alias 1 | 8 | constantly | 15 September 2000 | moderate | moderate |

Inactive Problems:

| Problem Name | Rating | How Often | Started When | Ended When | Initial Severity |
|---|---|---|---|---|---|

Add primary problem >>

Manage primary problems >>

FIG. 37

Medical Summary Report for liamg on 16th January, 2001.

This Medigenesis Medical Summary is intended to communicate the medical condition of our members. The alias used above is how the member is tracked on our Internet site. The report includes all of the member's problems, treatments and lab test results. It also provides health options designated by our staff, based on the experiences of our community and important discoveries and knowledge of current practices in medicine.

We at Medigenesis expect that this report will be used by you and your physician or medical practitioner to aid you in your quest for better health. We urge you to consult a medical professional before you decide on any course of treatment based on the options we provide here.

Summary Information

|  | Subject | Responsible person |
|---|---|---|
| Name: | ———————————— | ———————————— |
| Address: | ———————————— | ———————————— |
| City: | ———————————— | ———————————— |
| State: | ———————————— | ———————————— |
| Zip: | ———————————— | ———————————— |
| Phone: | ———————————— | ———————————— |

The spaces above allow you to personalize this report before you share it with a physician or medical practitioner.

Member Information

Age: 3
Gender: male
Height: 3' 5"
Weight: 51 lbs

Active Problem List

The following problems were designated by liamg as the Primary Problems affecting his or her health in an adverse way. Rating is a scale from 1 to 10 (where 1 is highest) of how important the problem is. Initial severity captures the severity of the problem when it was first listed. Generally speaking, a severe problem interferes significantly with normal activities and/or sleep and a mild problem does not. Moderate is in between. Latest severity is a number from 0 to 12 that relates an individual's overall feelings about this particular problem-everything about it rolled into one number. 1 means that it is not much of a problem any more, 12 means that it is a serious, incapacitating problem that is not getting any better.

FIG. 38

| Problem Name | Rating | How Often | Started When | Initial Severity | Latest Severity |
|---|---|---|---|---|---|
| Diarrhea | 1 | many times | 1999 | moderate | moderate |
| Lactose intolerance | 3 | | at birth | severe | severe |
| Asthma | 3 | 3 times ever | at birth | moderate | moderate |
| Eczema on leg | 1 | constantly | June 2000 | severe | severe |
| Eczema on arm | 2 | constantly | June 2000 | mild | mild |
| Eczema on chest | 2 | constantly | 5th week of October 2000 | mild | mild |
| Nightmares | 4 | frequently | May 2000 | moderate | moderate |

Secondary Problem List

The following problems were created in response to the Medigenesis Questionnaire.

| Problem Name | How Often | Started When | Initial Severity |
|---|---|---|---|
| Wheezing | | 1999 | moderate |
| Cradle cap | constantly | at birth | moderate |
| Awakens screaming/crying | many times | 2000 | mild |

Other Attributes List

The following Other Attributes were created in response to the Medigenesis Questionnaire.

| Attribute Name |
|---|
| DPT 2(Diphtheria-Pertussis-Tetanus) |
| Experienced no complications first month of life |
| Eye contact when spoken to |
| Fluoridated water |
| Follows instructions |
| Full term birth |
| Good behavior at school |
| Good diet |
| Good energy levels |
| Good long term memry |
| Good short term memory |
| Good with the computer |
| Happy childhood |
| Head normal |
| Healthy childhood |

FIG. 39

DPT 1(Diphtheria-Pertussis-Tetanus)
DPT 2(Diphtheria-Pertussis-Tetanus)
Experienced no complications first month of life
Eye contact when spoken to
Fluoridated water
Follows instructions
Full term birth
Good behavior at school
Good diet
Good energy levels
Good long term memory
Good short term memory
Good with the computer
Happy childhood
Head normal
Healthy childhood
Hib 1(H Influenzae)
Hib 2(H Influenzae)
High endurance
High IQ
Home air conditoner
Home gas stove
Home oil heating
Imagination
Imitates others
Initiates play
Intelligent
Intolerance, Yeast
Jumped by 2 years
Learned to walk by 12 months
Leggos
Light skin
Likes school
Matching and sorting
Move to present home
Municipal water/home
Normal development
Normal stature
Physical coordination
Pincer grasp (thumb and index finger)
Plays well with small objects
Pleasant/easy to care for
Polio Vaccine Injection 1
Polio Vaccine Injection 2

FIG. 40

SYSTEM AND METHOD FOR THE AUTOMATED PRESENTATION OF SYSTEM DATA TO, AND INTERACTION WITH, A COMPUTER MAINTAINED DATABASE

CROSS REFERENCE TO RELATED APPLICATIONS

This application claims the priority and benefit of U.S. Provisional Application No. 60/176,535 filed Jan. 18, 2000, as well as U.S. Provisional Application No. 60/233,041, entitled "SYSTEM AND METHOD FOR THE AUTOMATED PRESENTATION OF HEALTH DATA TO, AND ITS INTERACTION WITH, A COMPUTER MAINTAINED DATABASE, TO GENERATE INFORMATION REGARDING POSSIBLE REMEDIES, THERAPIES, PROBLEM SOLUTIONS AND BENEFICIAL PRACTICES, TO IMPROVE USER HEALTH" filed on Sep. 15, 2000, Sidney M. Baker, Inventor, the disclosures of each of which are hereby incorporated herein in their entirety.

BACKGROUND OF THE INVENTION

1. Field of the Invention

The present invention relates generally to the fields of data mining, expert systems, and system theory. In particular, the preferred embodiment relates to interactive data mining regarding the health of a human organism, described as a system.

General System Theory was introduced in the early twentieth century by the German/Canadian Biologist Ludwig Von Bertalanffy. Classical science, and its diverse disciplines, be they chemistry, biology, psychology, or the social sciences, tended to isolate individual elements of the observed universe, such as chemical compounds and enzymes, cells, elementary sensations, freely competing individuals, etc. and assumed that by putting theses elements together again, either conceptually or experimentally the whole or system under consideration—i.e., the cell, mind, or society—would result and be intelligible. In engineering terminology this approach was equivalent to reducing every system to the linear response of its various components and superposing or aggregating those linear responses to monitor the system as a whole. The problem with such an approach, or opistimology, is the fact that a whole is often more than the sum of its parts. There is often nonlinear and non-intuitive interaction and interdependence between the so called "components" of any system. General system theory is the scientific exploration of wholes and wholeness. General system theory assumes that for a true understanding of any system comprehension not only of the elements is required but of their varied interaction and interrelations as well. This requires exploration of systems in their own right and specificities.

The application of general systems theory to medicine would require nonlinear medical thinking. It mostly has to do with the approach one takes towards understanding what has caused and event, such as a symptom or a collection of symptoms, signs, and lab tests which are referred to as an illness. As present most medical thinking remains linear. Doctors and patents alike are tempted by the idea that an illness has a single cause that can be treated with a single remedy; such as a pill or a surgical procedure. General systems theory, when applied to medicine, presents ideas about causality in which a web of interactions produces a result that is not easy to pin on a single causative facture. Therefore the resolution of medical problems, or health is sustained by achieving a state of balance among countless strands of the web of genetic, physiologic, psychic, developmental, environmental factors all of which contribute to the state of well being, or lack thereof of human beings. When something goes wrong with ones health, it makes sense to pay attention of all aspects of this web that can be addressed with reasonable cost and risk.

The notion of systems is not unknown to traditional medical thinking. However, its meaning is quite different from the sense it is acquired among the inheritance of general systems theory. Traditionally, medical education is organized via various bodily systems such as the cardiovascular, nervous, immune, reproductive, gastrointestinal, integumentary (skin), musculoskeletal, endocrine, reticuloendothelial and hematologic. It is theses systems that serve as the basis for classifying disease. Upon graduation from medical school novice doctors are expected to choose a particular system and become a specialist. On the other hand, systems theory as applied to medicine provides a unifying model of how things operate, and allows the viewing of biological systems as interconnected and interacting unity of their various components. As a result, one can make functional—as opposed to anatomical—divisions, as overall balances assessed within the system. The theory that has dominated medical science for the greater part of the twentieth century is that people get sick because they are the victims of disease. A better theory is that people get sick because of a disruption of the dynamic balance that exists between themselves and their environment. This latter theory works just as well to describe what happens when one gets chicken pox as it does when there is a more complex problem in which many genetic, environmental, and nutritional factors interact.

Because of the prevailing disease oriented approach of medical language the illusion is created that if one possesses the name of a disease responsible for a patients complaints, then one can solve that patients health problem. A better mental model would be one in which all of the details of a person's problem are preserved as opposed to abstracting our theoretical based notions of important as opposed to unimportant "symptoms". Such a language would allow the totality of the information content of the state of a person's health at a given time be preserved. All that would remain needed is the means to extract it and to analyze it.

Digital computers are particularly adapted to such a task. Portraits of a human health status, including reported symptoms, observant indications and laboratory reports can be constructed in such a way so as to preserve the totality of information contained in such a health "snapshot" while still using the names commonly used in medical science to describe the main features of illness. Computers are utilized to make complex pictures out of human health data. If the data is detailed, accurate and structured, the pictures will reflect reality and allow patterns to emerge which are not necessarily visible to the naked eye. The computer can be used as a "microscope" for viewing large patterns as much as the microscope is used to view the exceedingly small.

In order to use a digital computer in such a way, a format must be created that can be easily encoded into digital data, processed, and decoded into a meaningful output. Users' verbal descriptions of their medical states must be carefully guided into precise and orthogonal categories which can each be assigned a number value, resulting in a multidimensional set of numbers representative of each user's health snapshot. Each dimension would represent some medical attribute. The presence of absence of some condition, sensation, or state, the severity, frequency, or character of the condition, and the duration, onset in correlation to other states or user activities of the problem, to name some general examples.

2. Related Art

Related art in the field of the invention is sparse. Although there are numerous medical database/medical information computer programs and websites, accessible via a local computer, the Internet or other data network, all offering the user the ability to search for a variety of information, none offers the user an opportunity to express the totality of his or her current health snapshot using system provided categories and divisions of the semantic plane. As a result these sites function as efficient and highly accessible medical encyclopedias. Noting more. There is no actual interaction between knowledge stored in the websites server and the health snapshot of the user to generate information that the user would not otherwise know.

In fact, across the gambit of medical web sites and related and equilivent interactive informational tools, the "mental map" or "semantic plane" and the corresponding technical language or taxonomy, by means of which both the queries are posed to, and the information, or output is generated from, the system database—is the traditional disease based singular cause and effect model discussed above. Therefore, one can at these sites and their equilivent, learn the "causes" and treatments, of a variety of "diseases". As well, one can learn the "disease" causing ones reported symptomology usually, but one cannot discover what percentage of other persons reporting similar symptomology also have similar problems as the user which are not commonly considered to be part of the symptomology of the "disease". For example, suppose someone reports a shortness of breath. Because the medical informational tools currently available to the public do not dynamically interact with the information reported by a user (to the extent that they extensively query the user at all) a given user cannot know that eighty three percent (83%) of persons reporting or seeking the assistance of the medical website also had a strange rash on the soles of their feet. Or, as another example, persons reporting shortness of breath could acquire a variety of information about cardiovascular health and potential problems, but could never know how many people reported a folic acid deficiency and poor night vision as well.

It is only through the articulation of the totality of events (in reality a reasonable tractable representative set thereof) indicative of a human organisms health, including the various mental, biochemical, physical and other processes that completely describes the system as a whole that ones health "system" can be objectively described.

What is therefore desired or needed to truly exploit the massive automated information extraction and handling and processing capabilities of the digital computer, and by extension, a network of digital computers, is the creation of (i). A carefully constructed taxonomy that facilitates the exhausts of mapping of a human organisms health snapshot into words (ii). System of querying the user so as to translate his or her responses into the categories of said taxonomy that would allow complete mapping of their health snapshot, (iii). A means of encoding information content of the user health snapshot into numerical values that can be manipulated by digital computer, and finally (iv) a method of processing the encoded information representing a user's health snapshot so as to allow the interaction of that user's health snapshot with a database of other user's health snapshots so as to generate meaningful inferences and analysis of the user's health snapshot so as to output meaningful information to the user.

SUMMARY OF THE INVENTION

A system and method are presented for the articulation, in data structures which can be operated upon by digital computers, of the health snapshot of a human being, and the interaction of that human's health snapshot with a database of other system users' health snapshots so as to obtain information and meaningful problem solving approaches with regard to the state of the human being's health. Although the techniques described can be applied to any comprehensive description of an organic or other system (e.g., horses, a chemical manufacturing system, an automobile) and any database cataloging events and problems experienced by, possessed by, or involving such systems, in the preferred embodiment the system under consideration is the mental and physical health of the human organism, and the database of systems and their events is a collection of the comprehensive descriptions of the health of a multitude of people. Each such health snapshot, or systemic description, comprehensively describes a persons health in terms of system common categories.

BRIEF DESCRIPTION OF THE DRAWINGS

The present invention will be more readily understood from a detailed description of the preferred embodiments taken in conjunction with the following figures. Many of the drawings consist of screen shots of an exemplary embodiment of the invention adapted to the World Wide Web. In this embodiment the trade name "Medigenesis" is used to denote the system, and as such, appears on many of the screenshots.

FIG. 1D depicts the fields of a Patient Description Vector;

FIG. 1E depicts the clustering concept;

FIG. 2 is a screenshot of an exemplary "What is Medigenesis" informational page;

FIGS. 3-3C depict an exemplary "Your Privacy and Security" page;

FIG. 4 depicts an exemplary "New Member Information" box from the account signup page;

Figure 5:
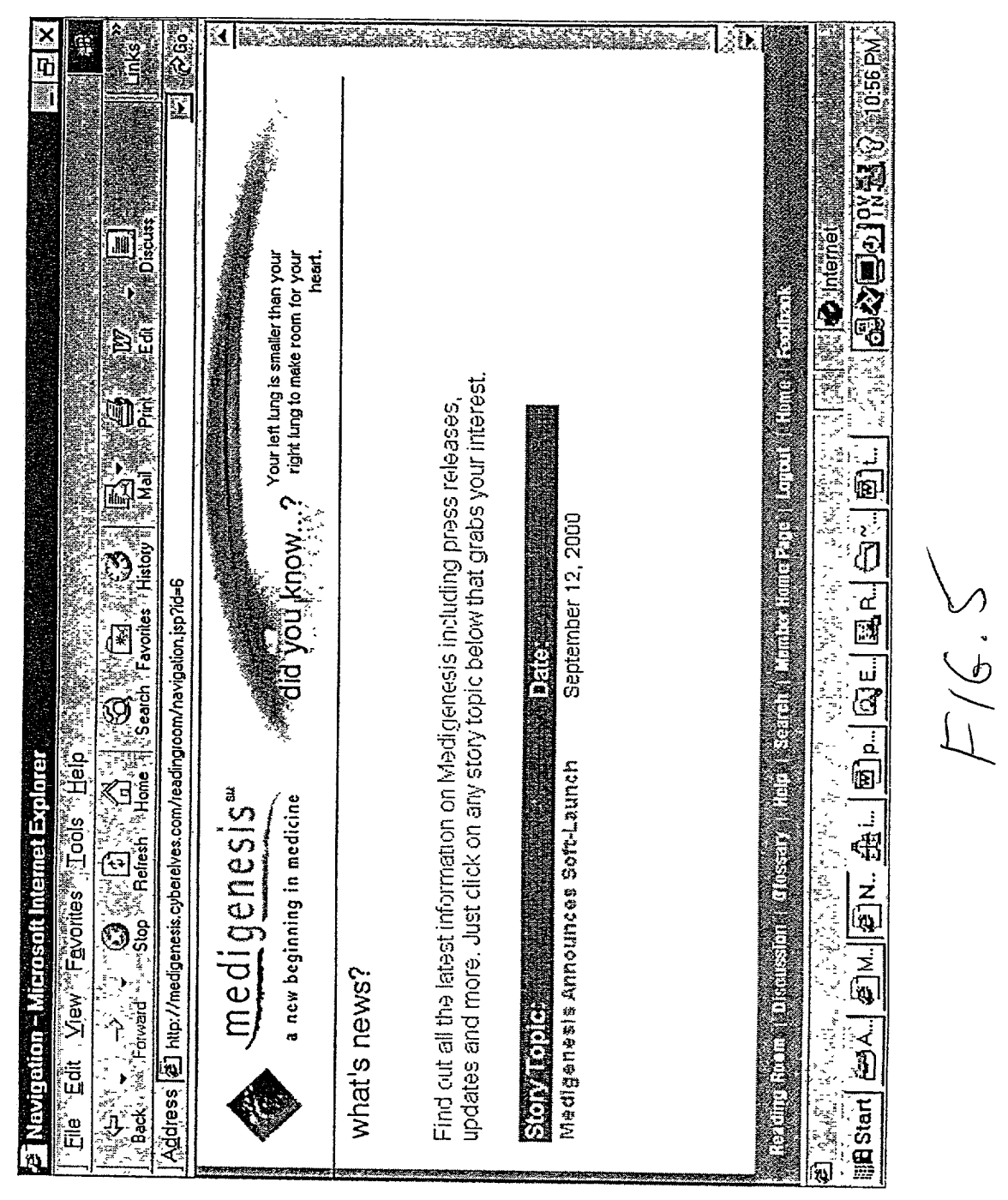

FIG. 5 depicts an exemplary "What's News" screen;

FIGS. 9 and 9A depict an exemplary "Discussion" screen;

FIGS. 12 and 12A depict an exemplary "Member Homepage" screen;

FIGS. 16-17 depict an exemplary "Event Locator" shown for a child female user;

FIGS. 26-32 depict examples of the help screens;

FIG. 33 is an exemplary depiction of

FIG. 33 is an exemplary depiction of the Member Homepage;

FIG. 34 is an exemplary depiction of the Your Health Profile page;

FIG. 36 is an exemplary depiction of the Treatments page;

FIG. 37 is an exemplary depiction of the Primary Problems interface;

FIGS. 38-41 are an exemplary depiction of a Medical Summary Report; and

FIG. 42 is an exemplary depiction of the Diagnostic Tests page.

DETAILED DESCRIPTION OF THE PREFERRED EMBODIMENTS

Figure 1:
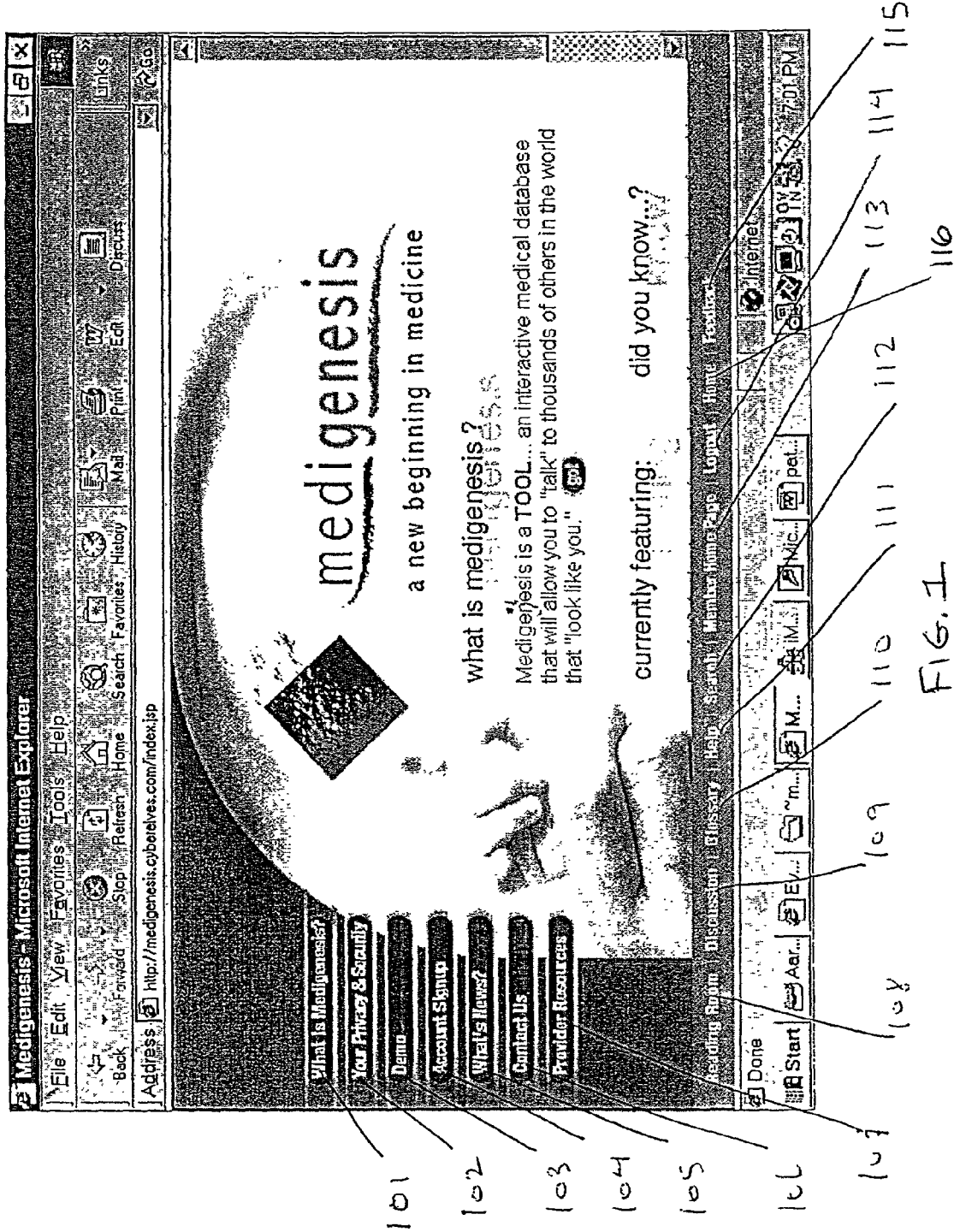
FIG. 1 is a screenshot of an exemplary system homepage.

You are chatting with an old friend at a party. After catching up on the latest baseball scores, your progress on a new project at work, an interesting recipe you tried recently for pasta primavera, and you mentioned you are worried about your oldest son. He is fourteen (14) years old, has developed acne, and his egama has gotten worse. He is really self-concious about his skin; one knows how children are at that age. That may account for why he has been getting such terrible stomach aches and headaches lately. The doctor wants to start him on antibiotics for the acne. You hate the though of him taking that stuff but what else can you do? "That's funny" replies your friend, as it turns out his cousin has a thirteen (13) year old daughter with strikingly similar problems; as it turns out she has developed an allergy to dairy products. Your friend continues, that simply by cutting most milk, cheese, and ice cream out of her diet her acne, eczema and stomach problems cleared up in less than one month.

Take that scenario and multiply it by thousands and thousands of people, and you have the idea of the preferred embodiment of the present invention. The system allows the user to tell it, via an automated graphical interface, about his or her medical problems, symptoms, lab test results, history, intuitive vague feelings about his or her health—in short, all the details that make a person, medically speaking, who they are—then automatically guides the user through a comprehensive questionnaire to take the user's comprehensive health description. Handing the acquired data to an information processing module the system then matches up the user with others within the system database that medically speaking "look just like the user", on the assumption that what has worked for them has a solid chance of working for the user.

The system of the preferred embodiment of the invention is therefore a tool of efficiency. It takes into account everything that makes the user who he or she is, mines the data inherent in the system database, and uses that interaction to generate a report that lists a variety of proposed therapies that have given other similarly situated users benefit. The system is also a tool of empowerment. It helps its users take better care of themselves and their families. After interacting with the system database, a user will be able to generate a medical profile of themselves, their child, or their parent, to share with their doctor. This allows the user to become a better informed patient of his or her doctor, thereby increasing the effiencies of physician provided therapies, as well as being able to ask the relevant questions, having been mentally prepared and informed by the system of the preferred embodiment of the invention well in advance.

In the past, medical databases were available only to medical professionals. The data they contained were in a language commonly spoken only by such professionals. By contrast, the system of the present invention uses ordinary language to interface with its users. It describes symptoms in the same words that a user might utter when talking to their doctor. It can be used by anyone, for anyone, at any time. Since it avails itself of widely accessible computer networks linking multitudes of individuals, such as the Internet, and is completely scaleable, the database can easily accommodate hundreds of thousands, or even millions, of users. The vast scale of the invention implies that there are bound to be a significant number of other users who look, medically speaking, very similar to the user. This offers him or her the benefit of the medical experiences and data of these other "medically similar" users. In effect, the system of the preferred embodiment of the invention is the largest continually operating cocktail party ever known.

However, in the case of the preferred embodiment of the invention, what the user finds transcends the best of imaginable cocktail parties. The system functions as an expert system that knows how to, most efficiently and comprehensively, query each attendee at the virtual cocktail party so as to coax them to articulate a comprehensive and complete expression of their medical state of being. Further, and at the same time, functioning like the stereotypical cocktail party gadabout, the system immediately communicates all useful information contained in the totality of the minds, bodies, and experiences of all of the other guests at the cocktail party to the user, so as to better inform and empower the user as to the state of their health and well being.

The system of the preferred embodiment of the present invention is constructed to accomplish three (3) functions. Information acquisition, information processing, and information output. Between the steps of information extraction and information processing there is an additional step of information encoding, and subsequent to the information processing step is another step of information decoding. While these coding/encoding steps are fundamental, they are simply means to interface the information between the user and the processing capability of a digital computer; in that sense they are secondary functions to the three main objectives of the preferred embodiment of the present invention.

Figure 1A:
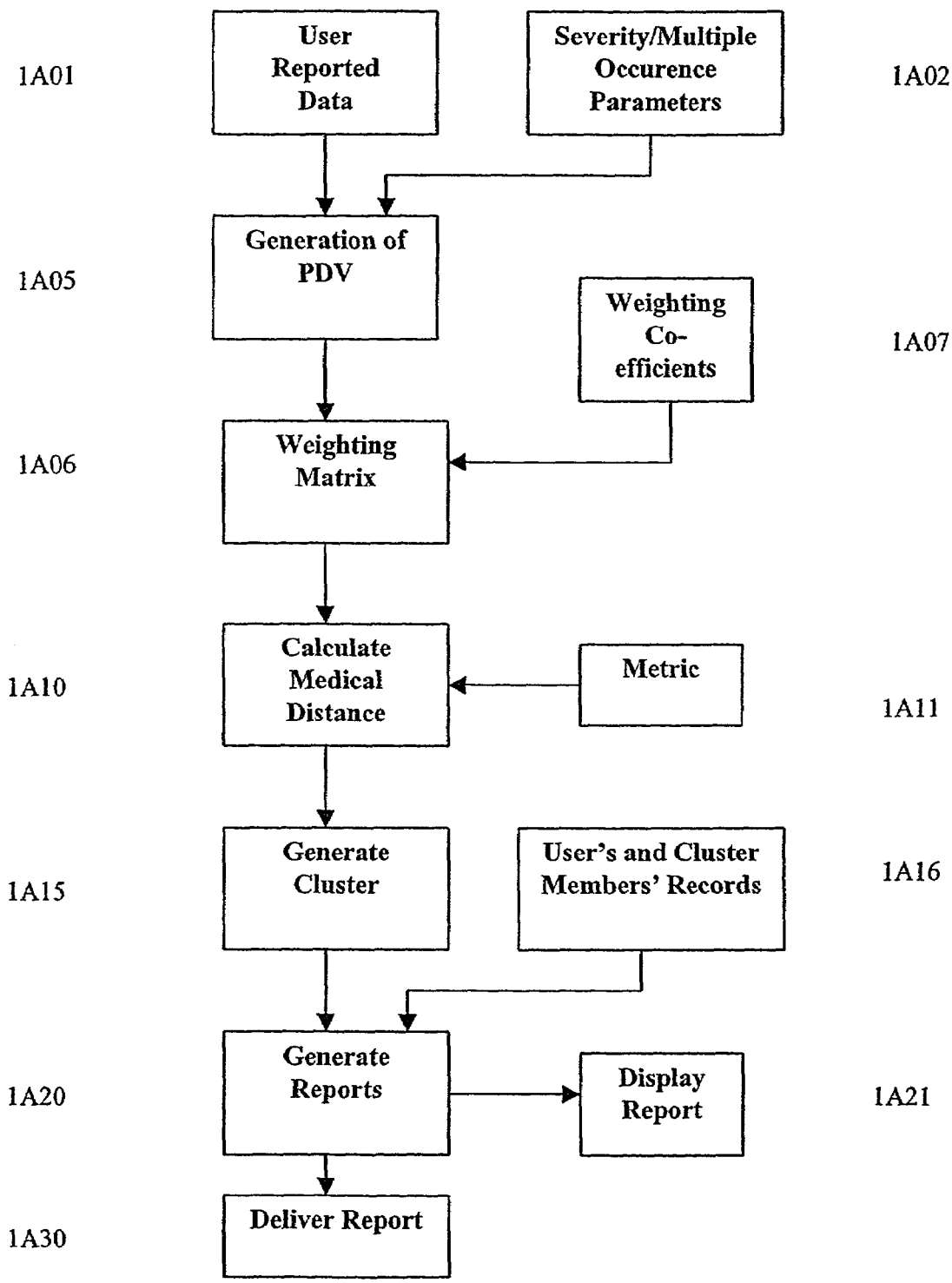
FIG. 1A depicts the system structure and data flow.
Figure 1B:
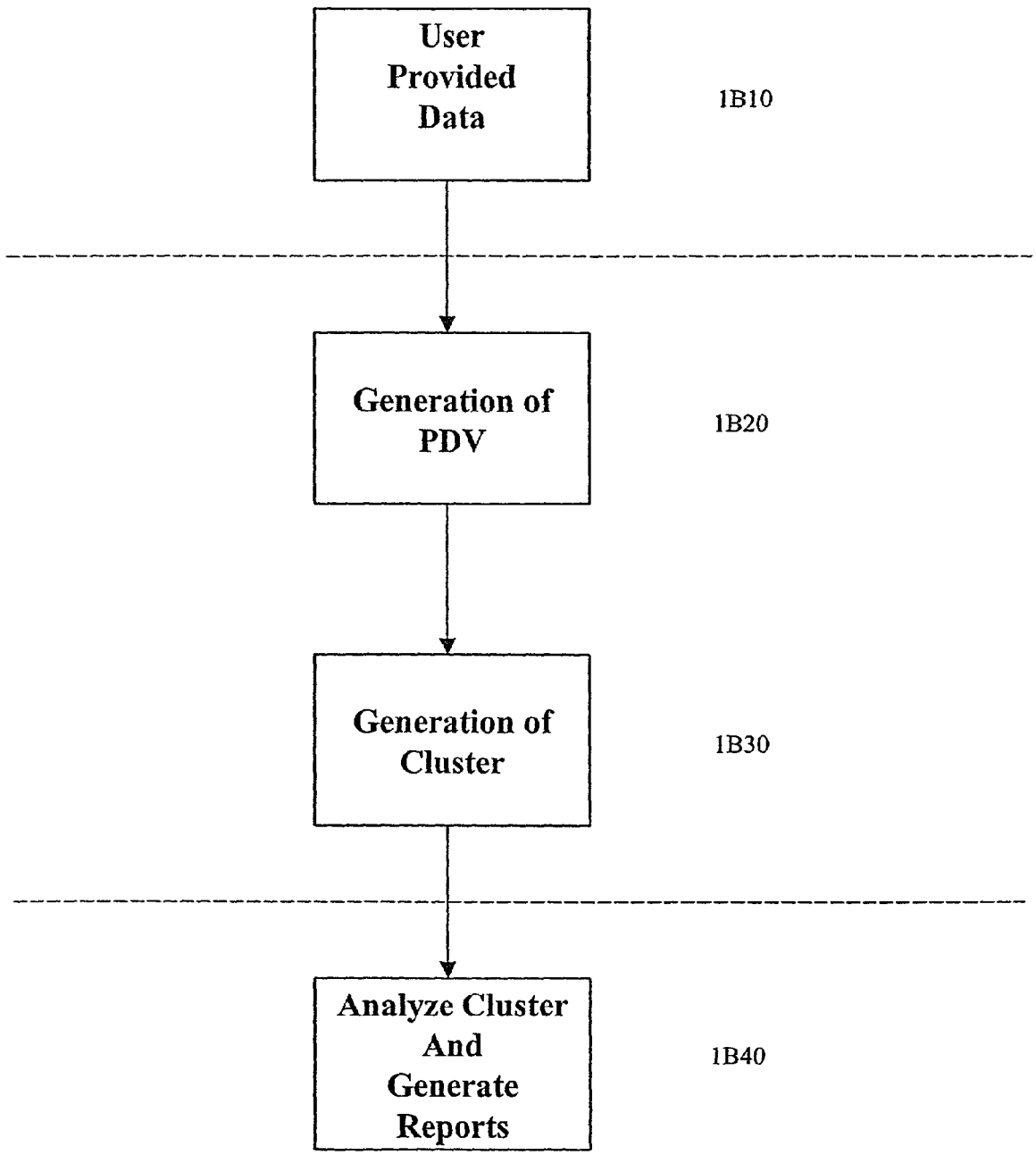
FIG. 1B depicts a simplified version of the system structure and data flow.

FIG. 1B illustrates a simplified overall process flow, illustrative of these three phases. The three phases are delineated by the horizontal lines dividing the chart into three parts. The information acquisition phase comprises obtaining the User Provided Data 1B10. The information processing phase comprises (a) generating the Patient Description Vector, or PDV 1B20, which is how the system "sees" the user, and (b) the generation of the cluster of similar users 1B30 in a "medical distance" sense, where greater similarity generates a larger score. Finally, the information processing phase comprises analysis of the cluster of medically similar users and the generation of reports 1B40 to the original querying user.

The information extraction phase consists of obtaining a complete and comprehensive snapshot of the individual user's health picture. In the language of system theory, a complete description of the system state is here elucidated. This is accomplished using the system's unique taxonomy.

The taxonomy is a language or lexicon that is detailed enough so as to allow the system to store a comprehensive description of the user which facilitates finding medically meaningful similar users, and at the same time comprises language that is natural enough to allow even the uneducated and unsophisticated user to meaningfully articulate his or her own medical state of being.

The information processing functionality is a unique method of what is known in the art as data mining or knowledge discovery. It involves a two (2) step process: (i) statistical processing of the system database to locate a set of other users similar to the querying user, and (ii) analysis of the set of similar users to find hidden patterns and useful remedies, possible solutions, therapies, and information. A simple example of such remedies would be the idea avoiding of dairy products which was exchanged between the two attendees to the example cocktail party discussed above. In the system of the preferred embodiment of the invention, however, this would not be a random, anecdotal, and unquantified piece of information exchanged between people chatting at a cocktail party. Rather, a statistically significant correlation between persons in the system database similar enough to the querying user to provide meaningful health analogies.

Knowledge Discovery in the Preferred Embodiment of the Present Invention

Before describing in detail the three stages of the system of the preferred embodiment of the invention and the detailed interactions with it which a user would undergo, it is first necessary to understand what the actual goal or functionality of the system is. This requires some appreciation of the underlying analytical techniques that support knowledge discovery from the system database. Because the system of the preferred embodiment of the invention is interdisciplinary in nature, i.e. it touches on the areas of semantics and the creation of a linguistic version of an orthogonal basis set, system theory, medicine and healthcare, and finally, data mining, knowledge discovery, and statistical analysis, it is felt necessary to provide some general conceptual background.

Next described, therefore, is what was termed above the information processing step of the preferred embodiment of the present invention, which relates to the general discipline of statistical analysis and data mining.

Different data mining methods can be employed to provide a "microscopic view" of the data which enable the detection of invisible patters among large numbers of recorded user histories. Using an assortment of data mining techniques users will be able to have a direct "knowledge exchange" with a structured database containing records of other users, their symptoms, and what medical options have worked for them. A key knowledge extraction technique that is employed in the preferred embodiment of the present invention is cluster analysis, sometimes known in the art as proximity analysis, or nearest neighbor analysis. Cluster analysis is an exploration of a data set of vectoral representations of database members, or entities, for the identification of natural groupings. The resulting natural groupings class similar entities together, and within a group the entities share similarities in the attributes that characterize them. In such cluster analysis no assumption is made about the number of underlying groups or any other structural aspect. Grouping is done after defining an appropriate similarity or distance measure. Typical example applications of clustering are customer segmentation and database marketing. Once the customers are divided into homogenous clusters, each cluster can be identified by cluster profiles or average cluster behavior. In the system of the present invention users are characterized in term of a representational vector, where the vector represents the user's medical situation/experiences, or what has been termed herein the "medical state of being."

As those who are skilled in the art will readily understand, this technique is sometimes referred to as nearest neighbor analysis. In nearest neighbor analysis an algorithm is constructed to find the nearest neighbors in a certain class or universe to which a given element belongs. In the system of the preferred embodiment of the present invention, not just the nearest neighbor is desired, but an entire set, or cluster, of nearest neighbors is desired to provide medical analogies for the query user. The set of nearest neighbors is defined by a dynamic algorithm which decides how near the set of nearest neighbors must be to the querying user in the multidimensional vectoral space which is the conceptual computing environment of the system. As will be readily obvious to those skilled in the art, one of the operands of the nearest cluster algorithm will be the "medical distance" measure assigned to the distance in the multidimensional vector space between the querying user and each of the other users in the database. This distance metric algorithm is itself dynamic and will be continually self optimizing so as to more and more optimally articulate the distance, in a meaningful medical/health sense (measured as the capability to provide useful treatment or diagnostic analogies and guidance) between any two users in the system database.

Another data mining technique that is often employed is the discovery of association rules. Association rules discover the correlations between attributes, such as, the presence of one particular attribute implying the presence of other attributes for an entity. An example of an association rule is that "whenever a given customer purchases salmon and mussels he also buys white wine". In commercial contexts, association rules are often used in cross marketing, store layout planning, catalog design, and the like. For two (2) sets of items x and y, an association rule is usually denoted as x~y to convey that the presence of the attribute x in a transaction implies the presence of y. The role of associations would be complementary to clustering (once the clusters are determined, mining for association rules within the cluster would provide useful information on the medical experiences of the cluster members).

These two primary techniques, clustering analysis and association rule discovery, are further extended in the system of the preferred embodiment of the present invention to include classification approaches, where real time classifiers are run to answer user posed questions. Classification deals with sorting a given set of observations into two (2) or more classes. The emphasis is on deriving a rule that can be used to assign a new observation to one of the classes, i.e., future predication. A classic example of classification is depiction of a disease. A classifier can be calibrated using a data set containing disease present and non-present vectors. Then it can be used to predict whether new patient vectors have the disease or not. Another example, from recent medical literature in the area of autism, is the detection of an environmental factor or factors significantly increasing the risk of autism. As is well known in the medical community dealing with autism, there has been established, in a statistically significant sense, a connection between children receiving the combined MMR vaccine (mumps, measles, and rubella) and the incidence of autism. Thus, a classifier could then be calibrated using a data set from the system database of autistic children containing those who received the combined MMR vaccine and those that did not. Then the classifier can be used to predict whether new users who received the combined MMR vaccine have, or, have a risk of developing, the disease or not.

FIG. 1A depicts the data flow in the preferred embodiment of the invention. Beginning with the User Reported Data 1A01, a user logs on to the site, and via an anatomical user interface and a comprehensive questionnaire, as described below in connection with the user interface, reports all relevant data to his health snapshot. Conceptually, this data allows the system to comprehensively describe the user's health "system" (to analogize to system theory), or her comprehensive medical state of being. This report is in the language of, and is stored in, the system databases allocated to each user, as a series of User Reported Problems/Events. How this information is elicited from the user is fully described below in connection with the user interface, and relates to the information acquisition aspect of the preferred embodiment.

Figure 1C:
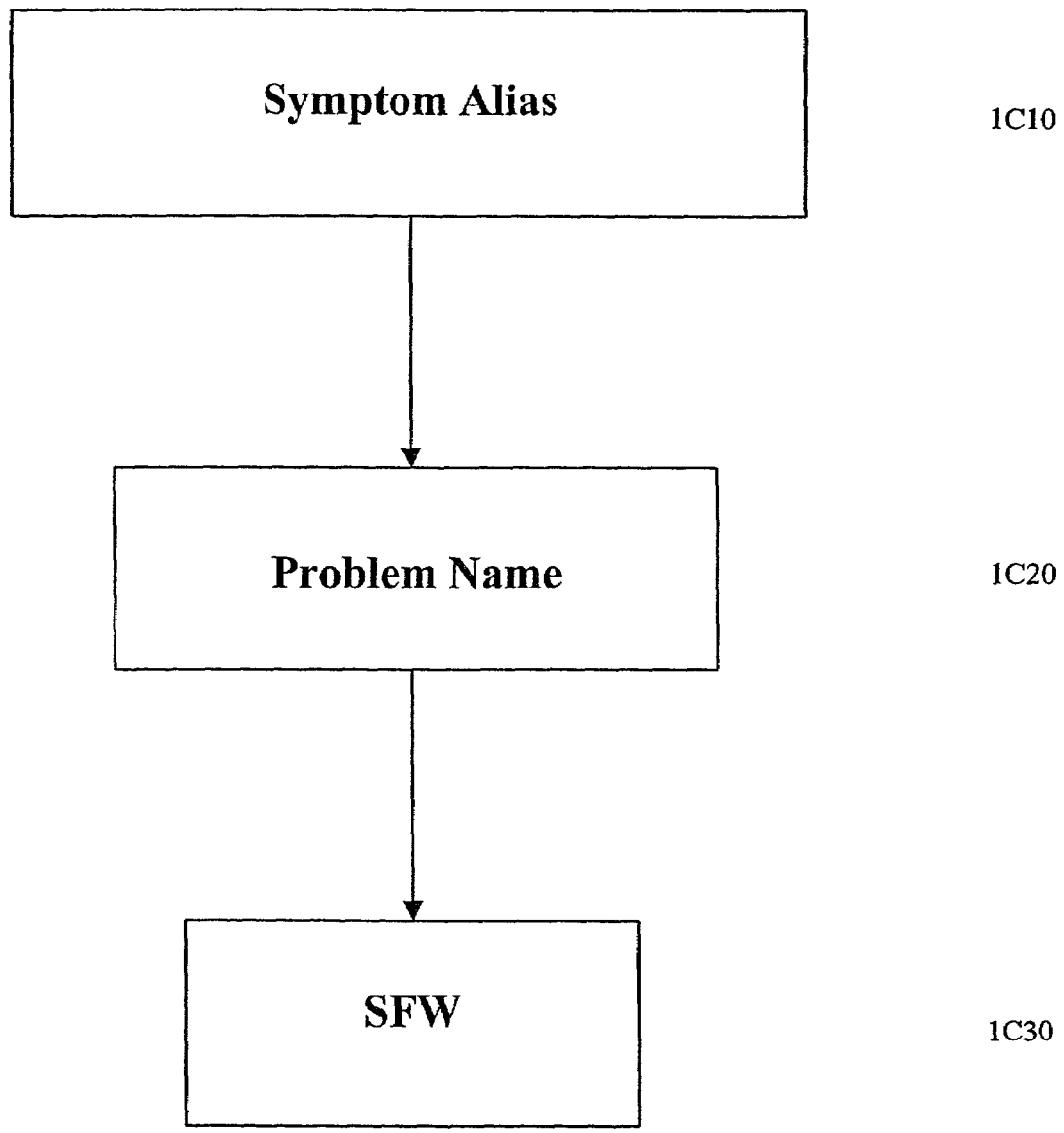
FIG. 1C depicts the descending levels of abstraction of user events.

Exhibit A-1 is an example listing of all user reportable or identifiable Problems/Events that are possible in the preferred embodiment, entitled EVENT LOCATOR. This list is dynamic, however, and can be modified as warranted by the continual internal system monitoring, for efficiency, clarity and comprehensiveness. As its name implies, the listing is oriented towards the Anatomical User Interface and the Questionnaire, as described below, and thus is organized first by the anatomical location on the body where the problem or attribute is manifested. This listing, having some 32,000 possible ailments or attributes, is simply too large to be used to represent the user in the system. Thus, it must be collapsed into more general groupings. Exhibit A-2, entitled "Medex_ Formal Problem", is such an example distillation. This Exhibit has three columns. The middle column, MEDEX-NAME, contains 5,597 unique user events, to which the entire 32,000 symptom aliases can be mapped. The third column (rightmost) describes whether the event is a medical problem, such as, for example, a spine injury or an allergy to latex, or simply a pertinent medical fact, termed an "attribute", such as, for example, having had a certain standard vaccine, or having traveled to a particular foreign country. The first (leftmost) column of Exhibit A-2 is the SFWID, which is an example set of 2204 possible System Function Where ("SFW") combinations. The SFWs, as more fully explained below, are the orthogonal categories by which a user is comprehensively represented in the system. FIG. 1C illustrates the increasing level of abstraction (going down the page) moving from the circa 32,000 symptom aliases to the circa 5600 problem names to the some 2200 SFWs.

Obviously there are two levels of abstraction ending up at the same place—the 2200 SFWs. Why? One purpose of the symptom alias is that it provides for members to describe a specific problem 'in their own words'. The example that always seems to get used to demonstrate this was 'stinky poop' versus 'smelly feces' versus wickedly pungent excrement. All say the same thing, yet each uses different words reflective of the user's soci-economic stratum and linguistic habits. Thus the some 32,000 symptom aliases have significant synonymy and semantic redundancy.

The other reason for duplication is that a symptom can appear, as shown below, in more than one place in the event locator—a person may click on arm, then skin, then 'eczema on the arm', or they may click on skin, then 'eczema on the arm'.

SFW—System Function Where:

the Central Data Structure of the System

SFWs are organized not by location (visually perceived spatial orientation), but much more efficiently by bodily system and function (conceptually perceived functionality), the latter being the reported problem or condition. The lowest level of abstraction of the SFW is the Where element, and identifies where anatomically that particular system's particular ailment or condition is manifest.

Exhibit A-3 contains an example listing of a set of 2204 SFWs, comprising an orthogonal basis set of medical conditions and facts by which a user's health state of being can be thoroughly expressed. The information processing module of the system of the preferred embodiment sees each user as a vector comprising an age component, a gender component, and N SFW components, where N is the number of all SFWs possible in the system. In the example listing of Exhibit A-3, N=2204. FIG. 1B depicts the increasing levels of abstraction between Exhibits A-1, A-2, and A-3.

Because an individual user may report data a number of times, but is represented by only one data structure within the system, multiple occurrences of a user event are collapsed into one value for that particular SFW, using an equation that maps one value to the SFW in question, including information regarding the number of occurrences and the severity of each occurrence. Referring again to FIG. 1, the reported information by the user 1A01, and the severity parameters 1A02, are distilled and combined to create the Patient Description Vector, or "PDV", which, as described above, is how the user is "seen" by the system's information processor.

An example of an SFW component of the PDV encoding the fact that a user has Eczema on the arm would be, in the example of Exhibits A, coded as "Skin-Inflammation-Not Specified" as is shown on the top record of page 110 of Exhibit A-2. Similarly, every member problem (or, synonymously, member event) from Exhibit A-1 has a corresponding SFW in Exhibit A-3.

PDV—Patient Description Vector

Figure 1D:
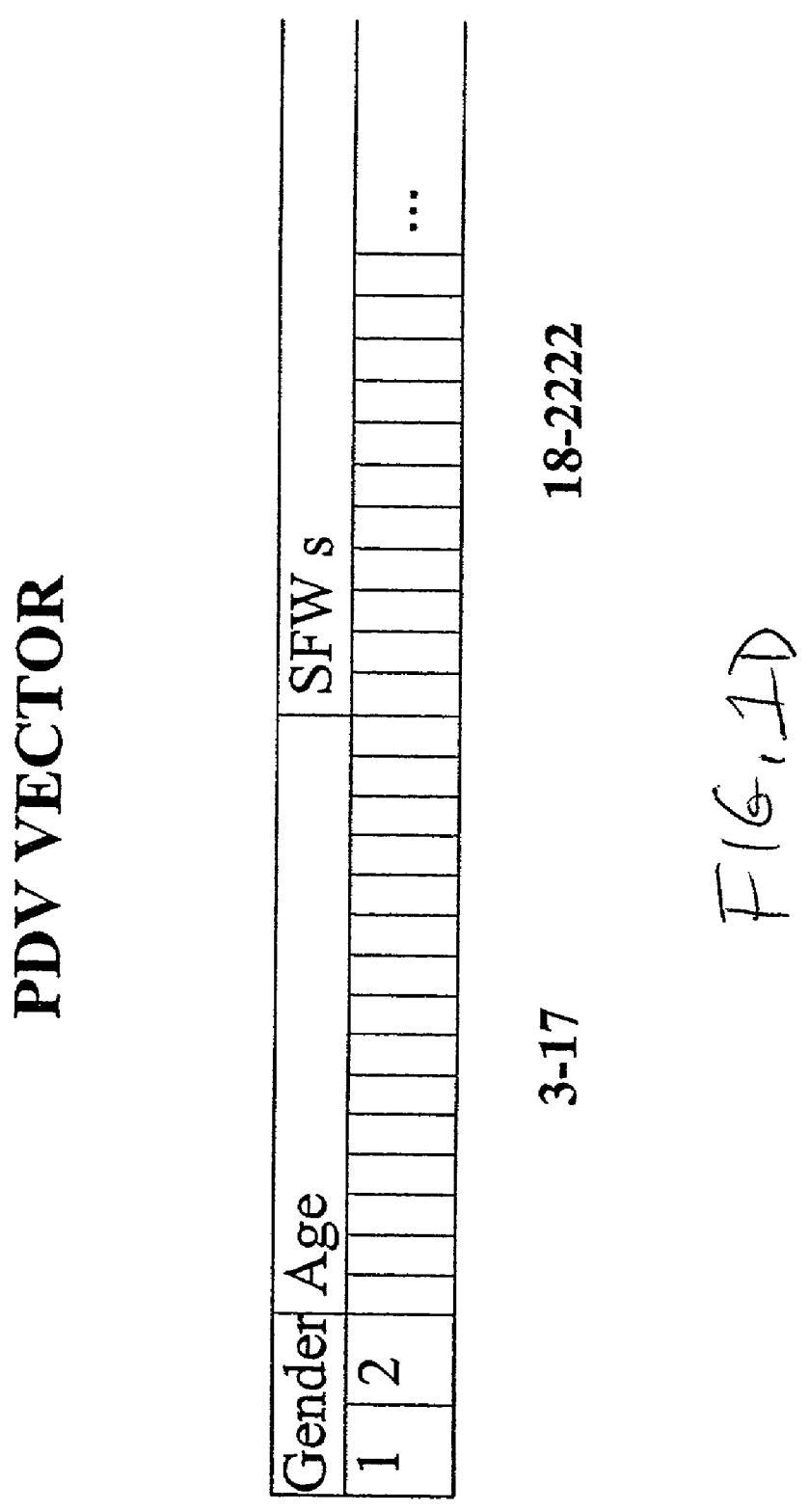

The PDV is a row of numbers that collectively define the point the relevant user occupies in the multi-dimensional hyperspace of all possible (considered) medical conditions. Each column in the row corresponds to a dimension in the hyperspace, and columns will be set aside for the following pieces of information, with reference to FIG. 1D: user's age, gender, and a column for each valid SFW.

Column 1: Gender=Male and Column 2: Gender=Female

The members' gender information will be encoded by placing a 1 in the appropriate column. No information (equivalently, a zero) will be placed in the other column.

Columns 3-17: Age

The age information will be encoded by placing a 1 in the appropriate column, and zero in the other columns. Each column will represent an age range of 7 years. So, if the member is younger than 7 a 1 will be placed in the first column, if they are younger than 14 (but older than 7) a 1 will be placed in the second column, etc.

Columns 18-2221: SFWs

As per Exhibit A-3, in an example of the preferred embodiment there are 2204 different, valid combinations of SFWs. Each of these will be assigned an identification number (an 'SFWid'), and each SFWid will in turn be assigned a 'column' in the PDV vector. Thus, the total columns in the vector in such an example are 2221, 17 for storage of the age and gender information, and 2204 for the SFWs.

The value which will be placed in the column corresponding to a given sfwid is given by the following equation.

$$PDV_{sfwid} = 1 + U_{pperB} \cdot \left[1 - \left(\frac{1}{a}\right)^i \left(\frac{1}{b}\right)^j \left(\frac{1}{c}\right)^k \left(\frac{1}{d}\right)^l\right]$$

Where:

$PDV_{sfwid}$=The number to be placed into the PDV vector for this sfwid. The parameters allow multiple occurrence information, as well as severity information (since there is no separate SFW for a severe, mild, or medium occurrence of the same event) to be encoded in the SFW value. These parameters operate as follows:

UpperB this parameter bounds the maximum that can be reached in an entry. (The actual maximum that can be reached is 1+UpperB);

a—parameter that controls the rate at which each extra 'mild' event (classified within this particular sfwid) brings the entry towards the upper bound;

b—parameter that controls the rate at which each extra 'moderate' or 'variable' event (classified within this particular sfwid) brings the entry towards the upper bound;

c—parameter that controls the rate at which each extra 'severe' event (classified within this particular sfwid) brings the entry towards the upper bound;

d—parameter that controls the rate at which each extra 'variable' event (classified within this particular sfwid) brings the entry towards the upper bound;

Input numbers (dependent on user data)

i, j, k, l—these numbers count the number of (respectively) mild, moderate, severe, and variable events that the given member has had, or currently has, which are classified to fall within this sfwid.

These severity parameters (which include the multiple occurrence information) are shown as an operand to the PDV in FIG. 1A, item 1A02.

These equations operating on the user provided data will lead to the generation of a vector 1A05 with reference to FIG. 1, where the number of columns, or the dimensionality of the hyperspace (n), will be on the order of 2200. Basically the PDV is simply a format to describe the member in a way conducive to 'proximity analysis'. Once the PDV is generated in the above fashion, it will be stored in the database for later retrieval, and for usage in reporting/debugging purposes.

Metric Calculation

Having To find the similarity between two members (as represented by their respective PDVs) a 'metric calculation' is undertaken. This metric operates as a variation on the dot product (which is a scalar measure of the extent that one vector lies along the direction of another, itself a measure of similarity; the dot product of a vector with itself is thus unity). The metric can be weighted to take into account that the dimensions, being word based and subject to interpretation, may not be absolutely orthogonal, or independent, and thus the coincidence of two different SFWs may actually deserve a significant similarity rating.

Calculation of the Metric

A crucial part of the system is the calculation of the 'similarity' between two PDV vectors. This step is shown as 1A10 in FIG. 1A. In the preferred embodiment, the formula used to calculate the 'similarity' between two PDV vectors, x, and y is given by:

$$\text{similarity\_measure} = \sum_{i=0}^{n-1} \sum_{j=0}^{n-1} w_{ij} \cdot x_i \cdot y_i$$

$$(\forall_{i,j} : w_{ij} > \tau)$$

Basically, the system multiplies every non-zero entry in x against every non-zero entry in y, using the corresponding component of the appropriate weighting factor matrix W, 1A06. The system then sums the result, completing the medical distance calculation 1A10.

However, where the weighting term (w) is zero, or when w is less than some (adjustable) threshold tau, that term is not counted in the summation, and no similarity is credited for the coincidence of the two SFW fields involved.

The above medical similarity metric 1A11 is actually a variation, or extension, of the well known 'dot product'. Obviously, it is dynamic, and can be easily changed so as to optimize the meaningfulness and usefulness of the medical similarity concept. The calculation of the metric can be understood, by considering, first, the 'dot product'. If we have two vectors in an n-space (in 2-space we might consider the closeness between two directions, or between two 2-D vectors), the simple dot product of those two vectors, x, and y, is given by:

$$= \sum_{i=0}^{n-1} x_i \cdot y_i$$

In the case that W in the metric discussed above had all ones in the diagonal, then the metric reduces to a normal dot product. That is, if $$W = \begin{bmatrix} 1 & 0 & 0 & 0 \\ 0 & 1 & 0 & \ldots \\ 0 & 0 & \ldots & 0 \\ 0 & \ldots & 0 & 1 \end{bmatrix}$$

then the metric is simply a straightforward dot product.

The way that the similarity metric calculation works can be adjusted by adjusting the parameters in W. It can also be adjusted, more easily, by changing the threshold tau.

Finding the Cluster

By repeated application of the metric (or some optimized equivalent) it will be possible to find the n members who are 'closest' to the current member 1A15. This list of 'cluster buddies' (having the highest scores on the similarity metric) will then be stored temporarily, for use in subsequent calculations.

Storage and Retrieval

The system of the preferred embodiment supports the storage and retrieval of data relating to cluster analysis. PDV information in particular, being multiple thousands of columns wide, needs to be stored in a data-compressed way, and yet, be retrievable in a vector format. The primary data stores include the following.

- PDVs (the latest PDV for every member, including the calculated length of that PDV);
- Similarity matrix information (the matrix of similarities calculated between PDV's, or equivalently, members, being of size M×M, where M is the number of members, or alternatively, a vector of 1×M for each member, stroing his or her similarity measure from all of the others); and
- Supporting information for the metric calculation (the weighting matrix W).

Performance

A good part of the accuracy for this method of measuring 'similarity' between members depends on the exact values chosen for the weights matrix W, and for the threshold Tau. A high threshold (or a lot of zeros in W) leads to less dimensionality in the calculation and consequently more tractability in trying to find similar members. On the other hand, a low threshold tau (or a lot of high numbers in W) is equivalent to saying that all factors in the body are tightly interrelated, and consequently a high dimensionality in the calculation. The same trade off applies to the question of whether the Upper-Bound, and the a, b, c, d parameters are set high or low during the generation of the PDV. Therefore, it is expected that the method for generating W, and the choice of optimum values for the other parameters will evolve to higher precision and better predicatability. The method of the preferred embodiment for achieving this evolution is to define one or more success measures, and create a genetic algorithm to automatically periodically diagnose system performance in terms of the one or more success measures, and automatically modify the various equations for the similarity metric, for W, and for the severity and multiple occurrence parameters.

Determining the Optimal Number of People to Display (Creating Dynamic Clusters)

In basic applications of clustering, groups (or clusters) are formed a priori in the metric space, and a new individual is mapped to the closest group. In the approach of the preferred embodiment, the distance (metric) of the new person to each of the persons (historical) in the database is calculated, and we select people that are "close" to him in a ranked manner. In such a scheme, the question arises: How many people are "close enough" to the new person? One logic would be to show the people that closer than a certain threshold (these people would then be showed in a ranked manner, closest to the farthest). Similarly, a certain fixed number of cluster buddies or a percentage of the total number of database members could be chosen. Optimally, it is desirable to let the data itself determine the natural boundary. Other users in the vicinity are included in the cluster until a gap is encountered that is bigger than a gap threshold. The logic can be visualized in the plot shown in FIG. 1E:

In FIG. 1E, the points lying in the Region A are considered close, and the points lying outside region B are considered "not close".

Consider the following series of distances:

Distances: 1, 1.2, 2, 2.5, 3.0, 4.0, 7.0, 8.0, 8.5

The gaps between successive prospective "cluster buddies" are then:

Gaps: 0.2, 0.8, 0.5, 0.5, 1.0, 3.0, 1.0, 0.5

Gap Moving Averages:

Moving Average 1=0.2;

Moving Average 2=(0.2+0.8)/2=0.5

Moving Average 3=(0.2+0.8+0.5)/3=0.5

Moving Average 4=(0.2+0.8+0.5+0.5)/4=0.5

Moving Average 5=(0.2+0.8+0.5+0.5+1.0)/5=0.6

At this stage, the next gap (=3.0) is significantly greater (order of magnitude=5) than the current gap moving average of 0.6. Hence the point may not be desired to be included in the group, and the cluster is restricted to the first 5 cluster buddies.

User Interface and Data Acquisition

What has been described above relates to the information processing aspect of the preferred embodiment of the invention. Temporally, this information processing stage occurs after the information acquisition stage, where the complete systemic description of a user's medical/health state of being is elicited, and mapped to the SFW's comprising the Patient Description Vector, PDV. What will next be described is the information acquisition aspect of the preferred embodiment.

Figure 3:
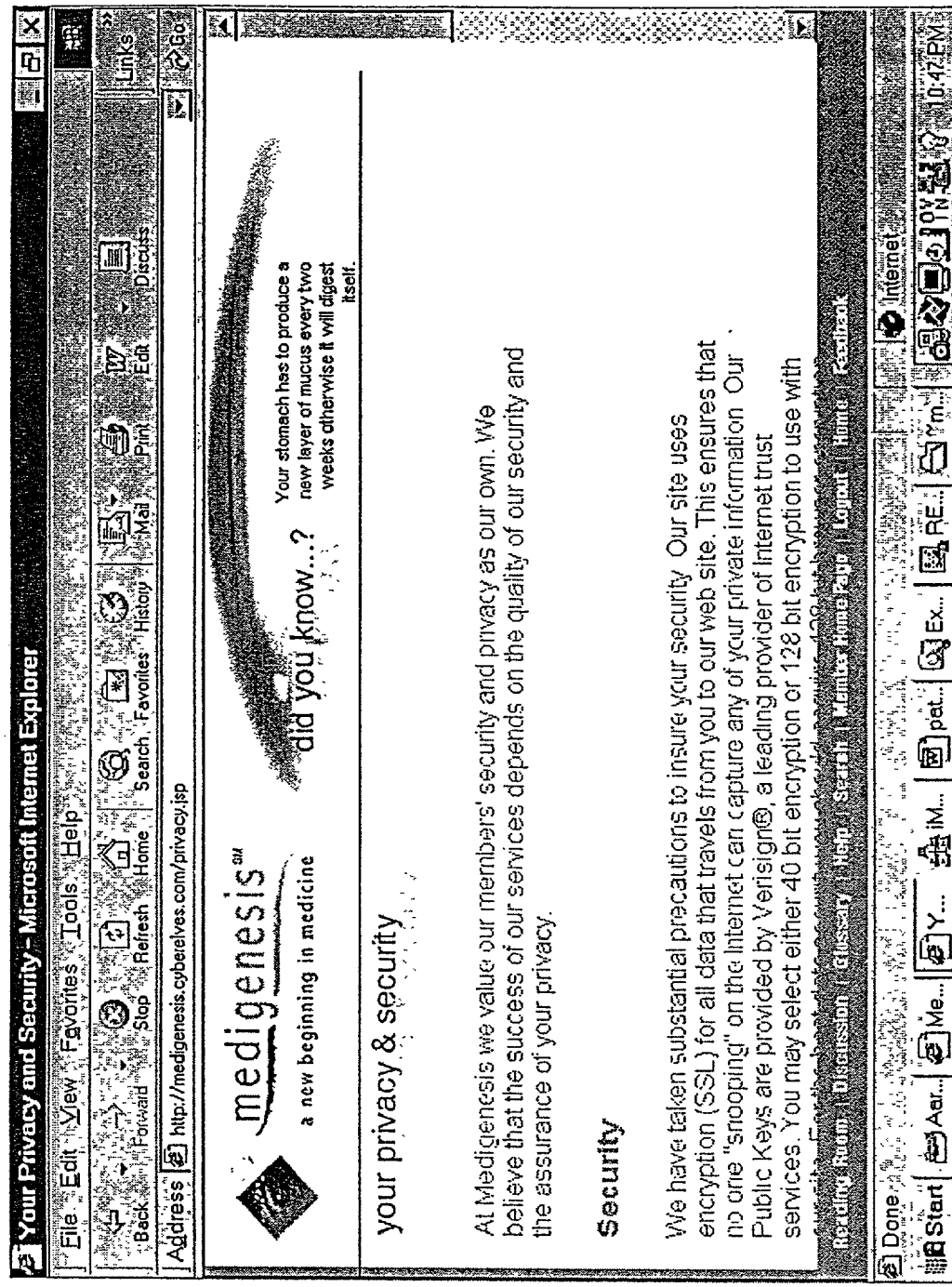

The system of the preferred embodiment of the present invention is implemented on a computer network, such as the Internet. The user's gateway to the system is the Home Page, as shown in FIG. 1. Clicking on button 101 leads to a mission statement page, as shown in FIG. 2. Clicking on button 102 leads to the Your Privacy and Security page, shown in FIGS. 3-3C.

Figure 7E:
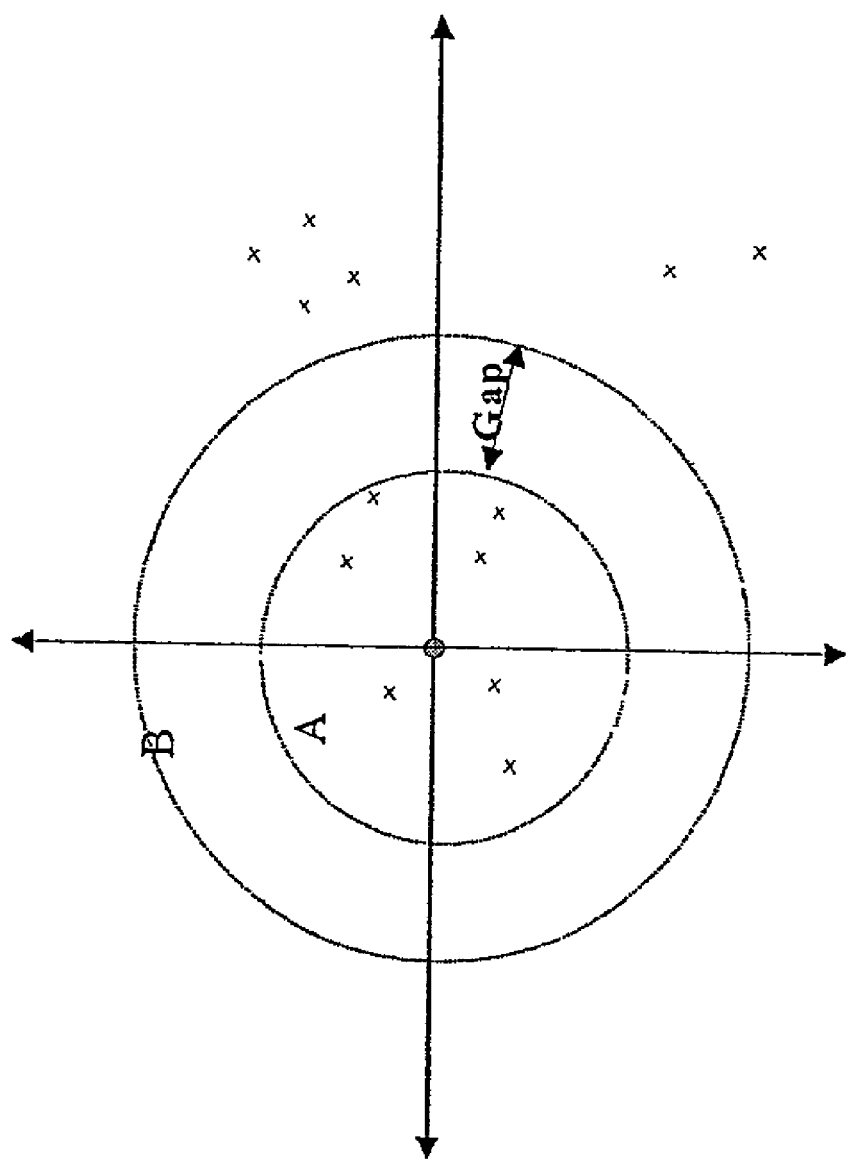
FIG. 7 depicts an exemplary "Provider Resourses" screen.
Figure 6:
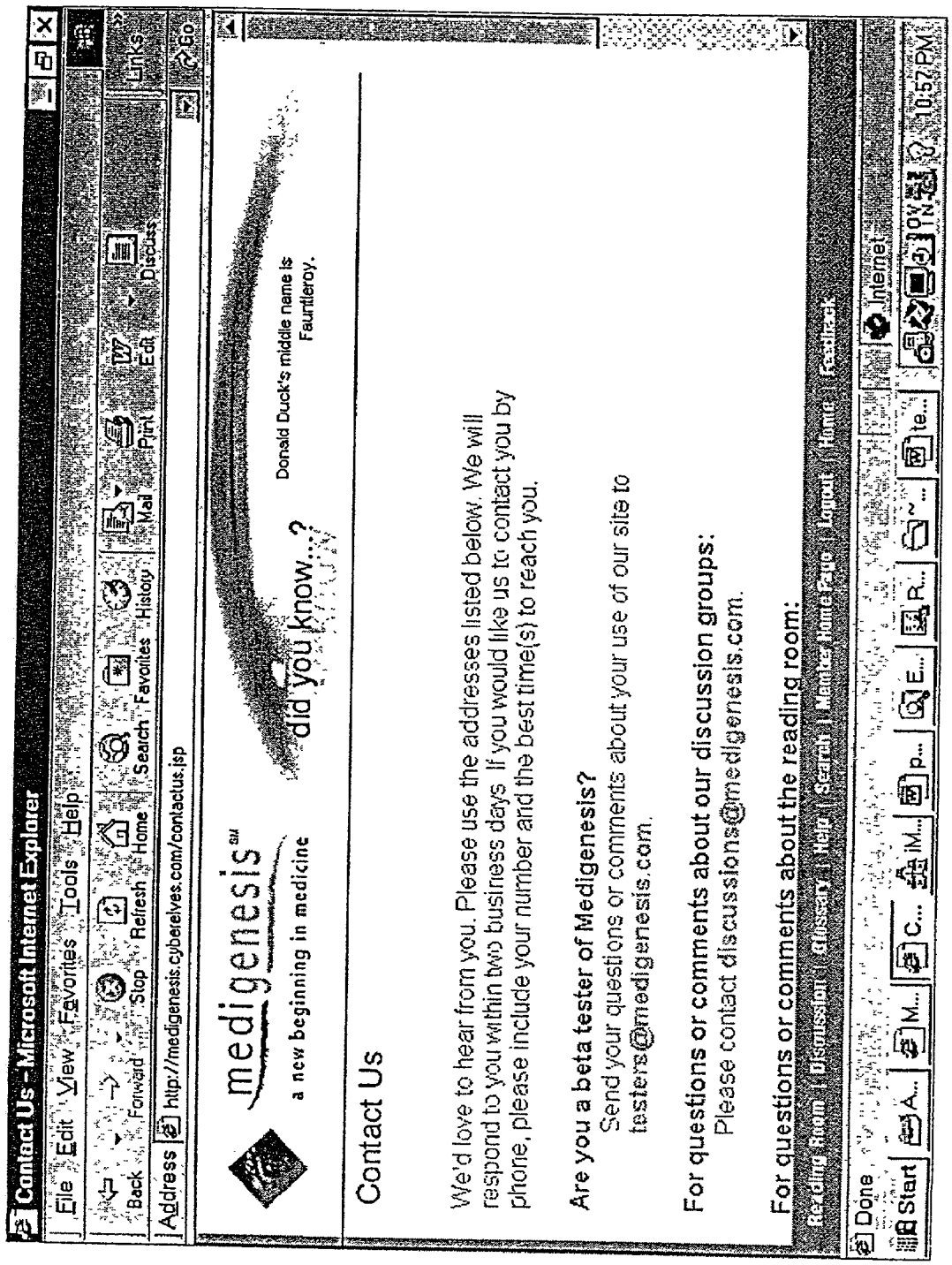
FIG. 6 depicts an exemplary "Contact Us" screen.
Figure 7:
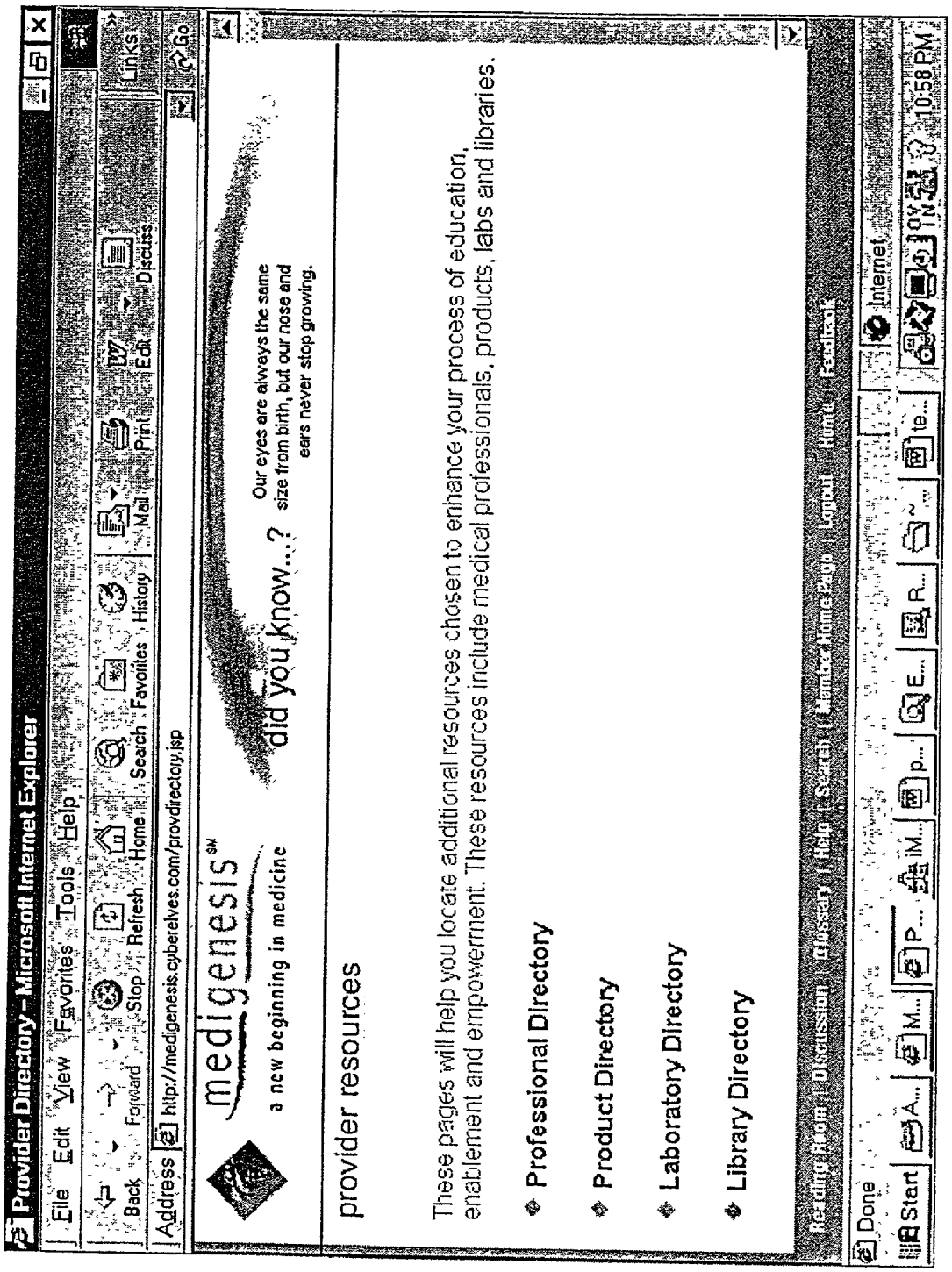
Figure 8:
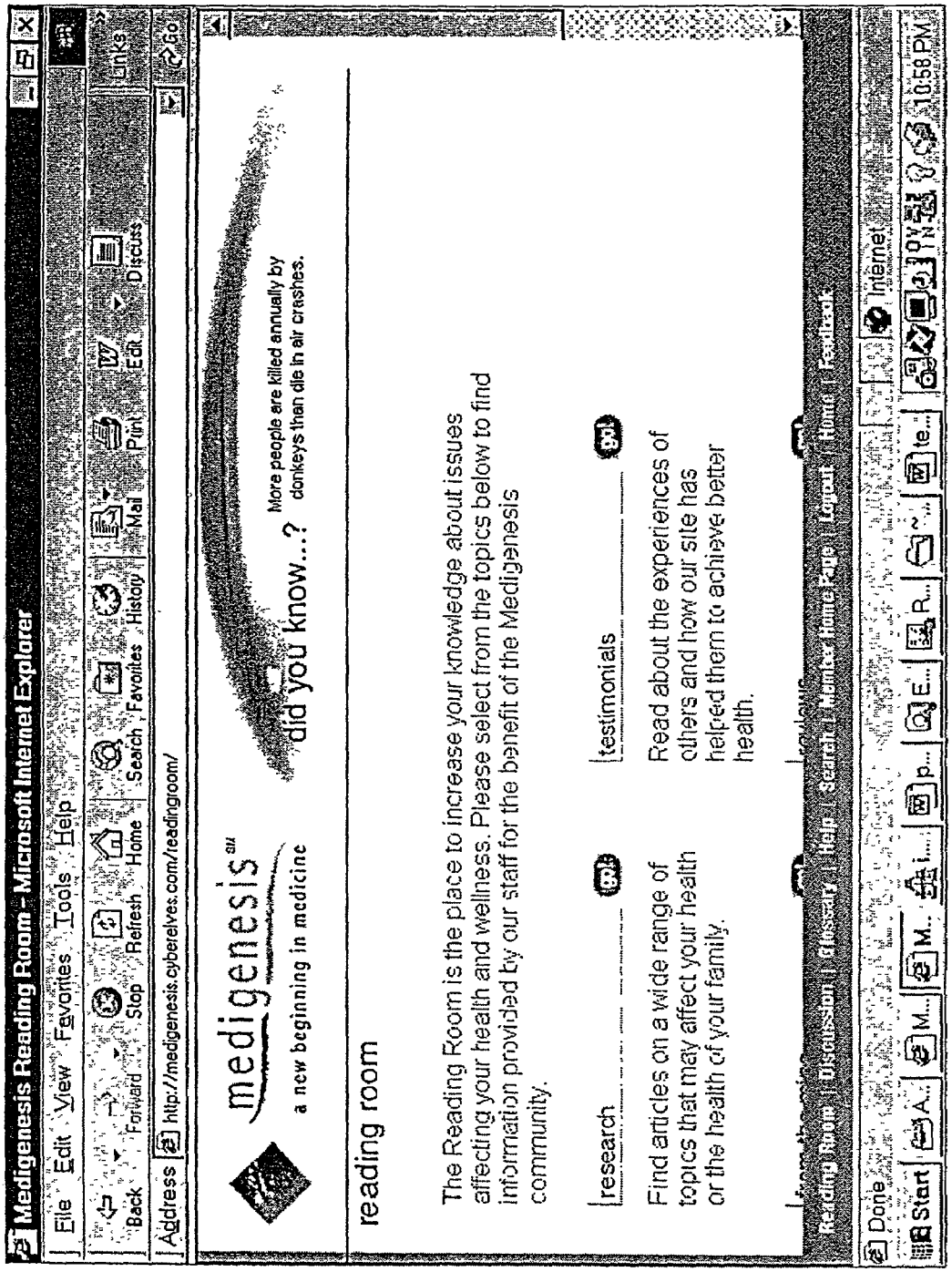
FIG. 8 depicts an exemplary "Reading Room" screen.
Figure 8A:
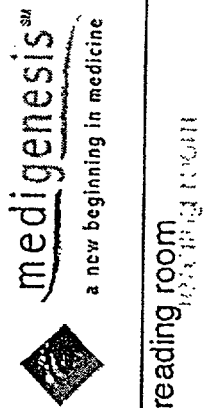
FIG. 8A depicts a fuller view of the exemplary "Reading Room" screen.
Figure 9:
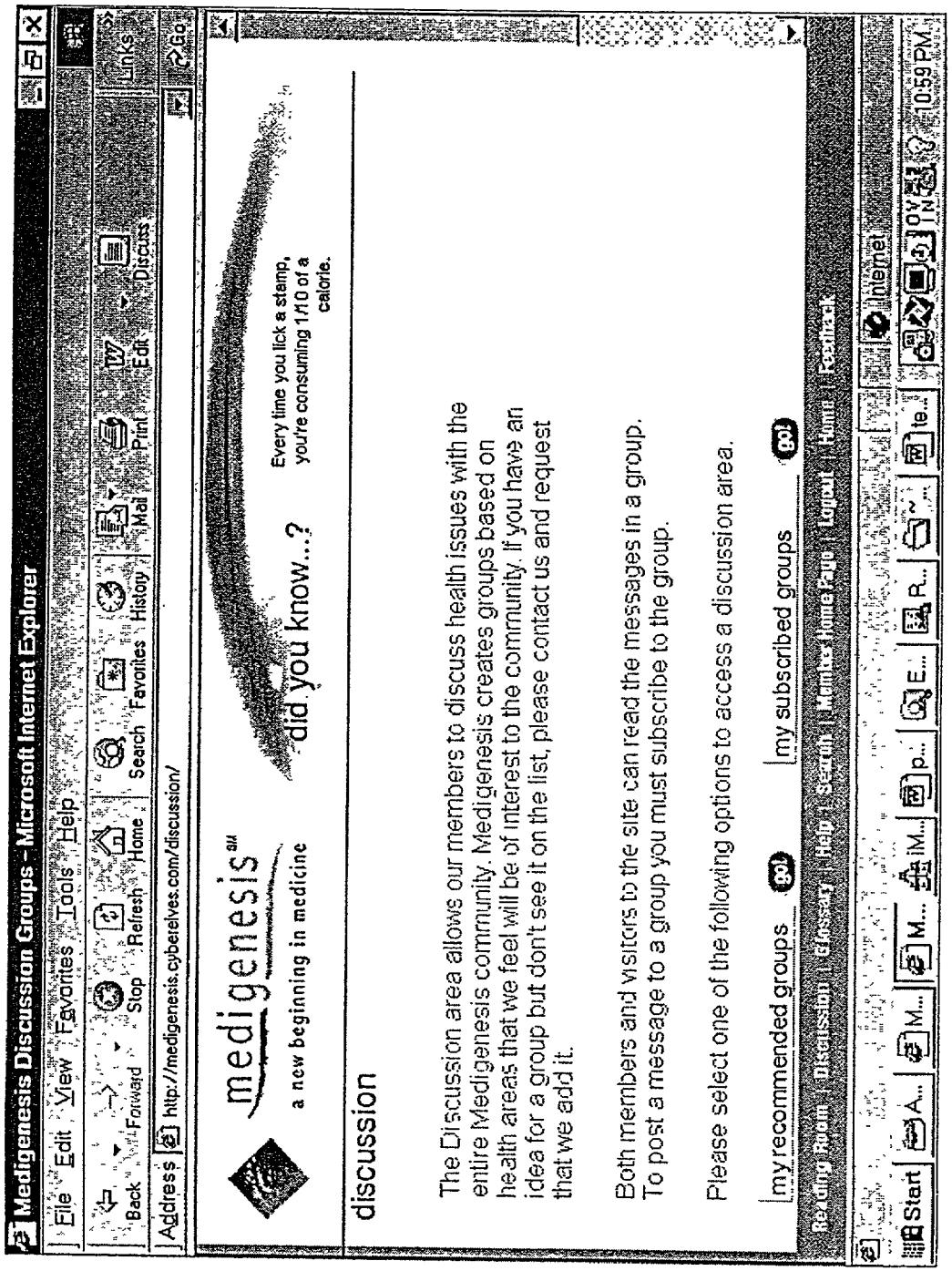
Figure 10:
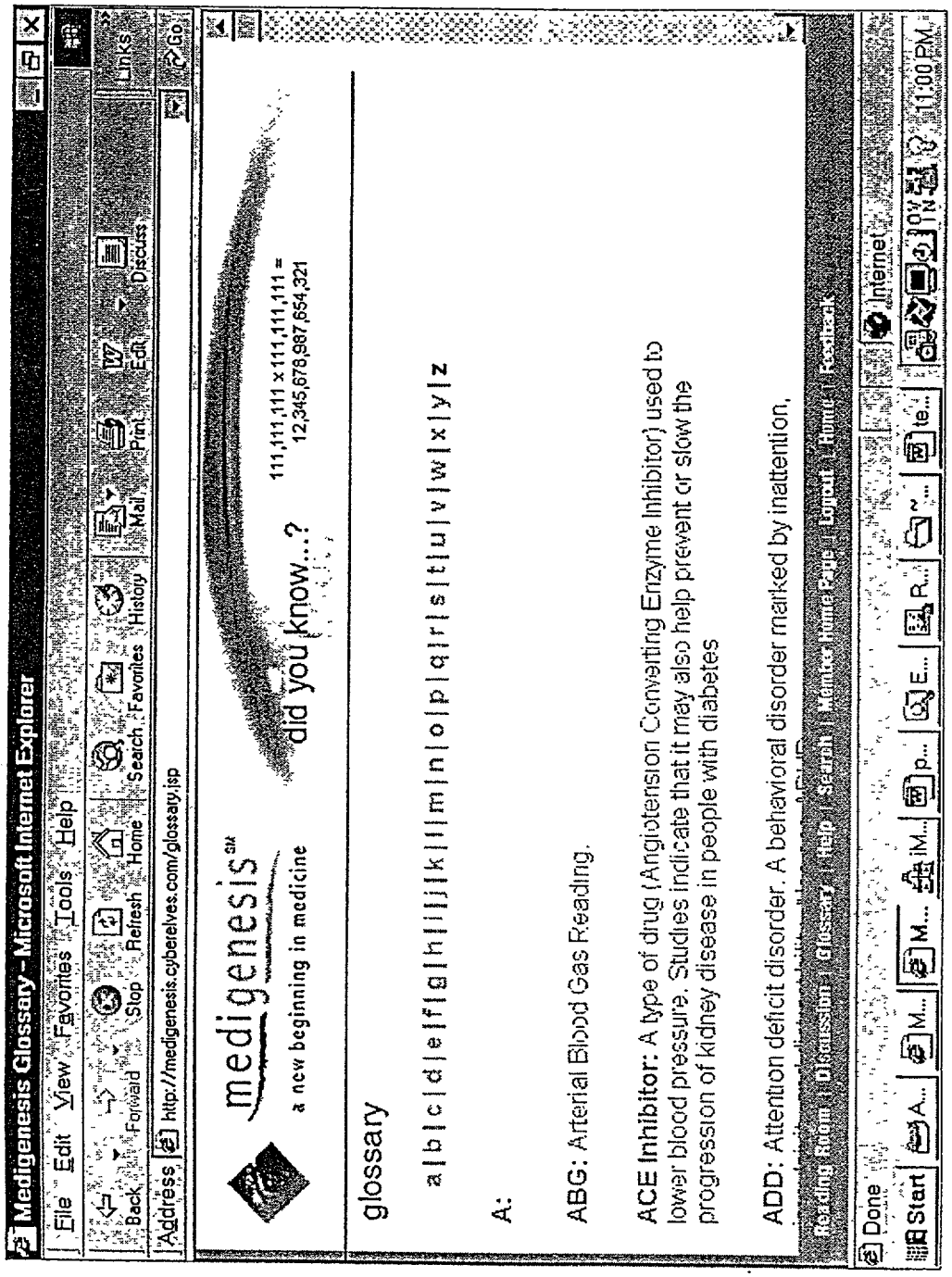
FIG. 10 depicts an exemplary "Glossary" screen.
Figure 11:
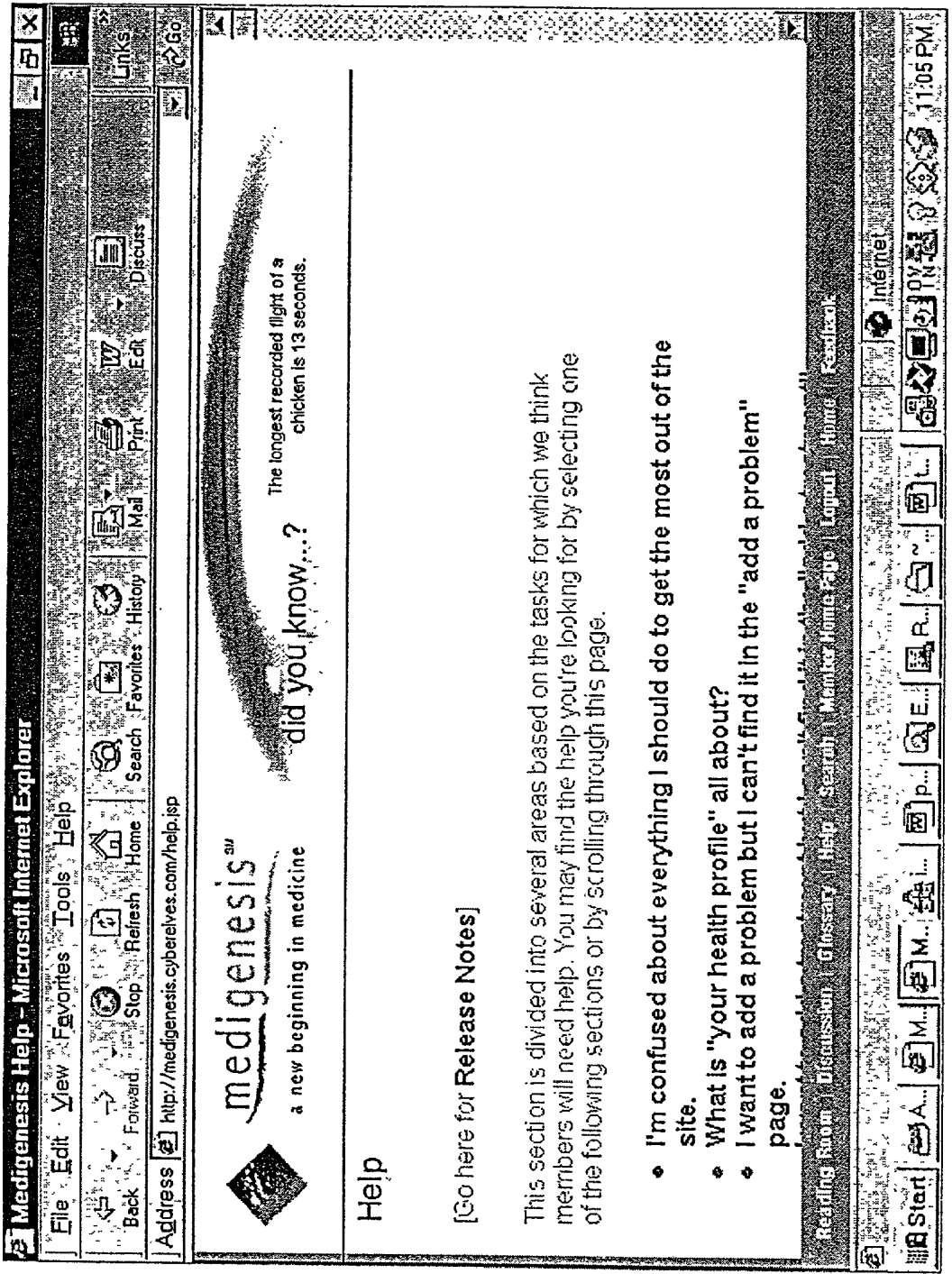
FIG. 11 depicts an exemplary "Help" screen.
Figure 12:
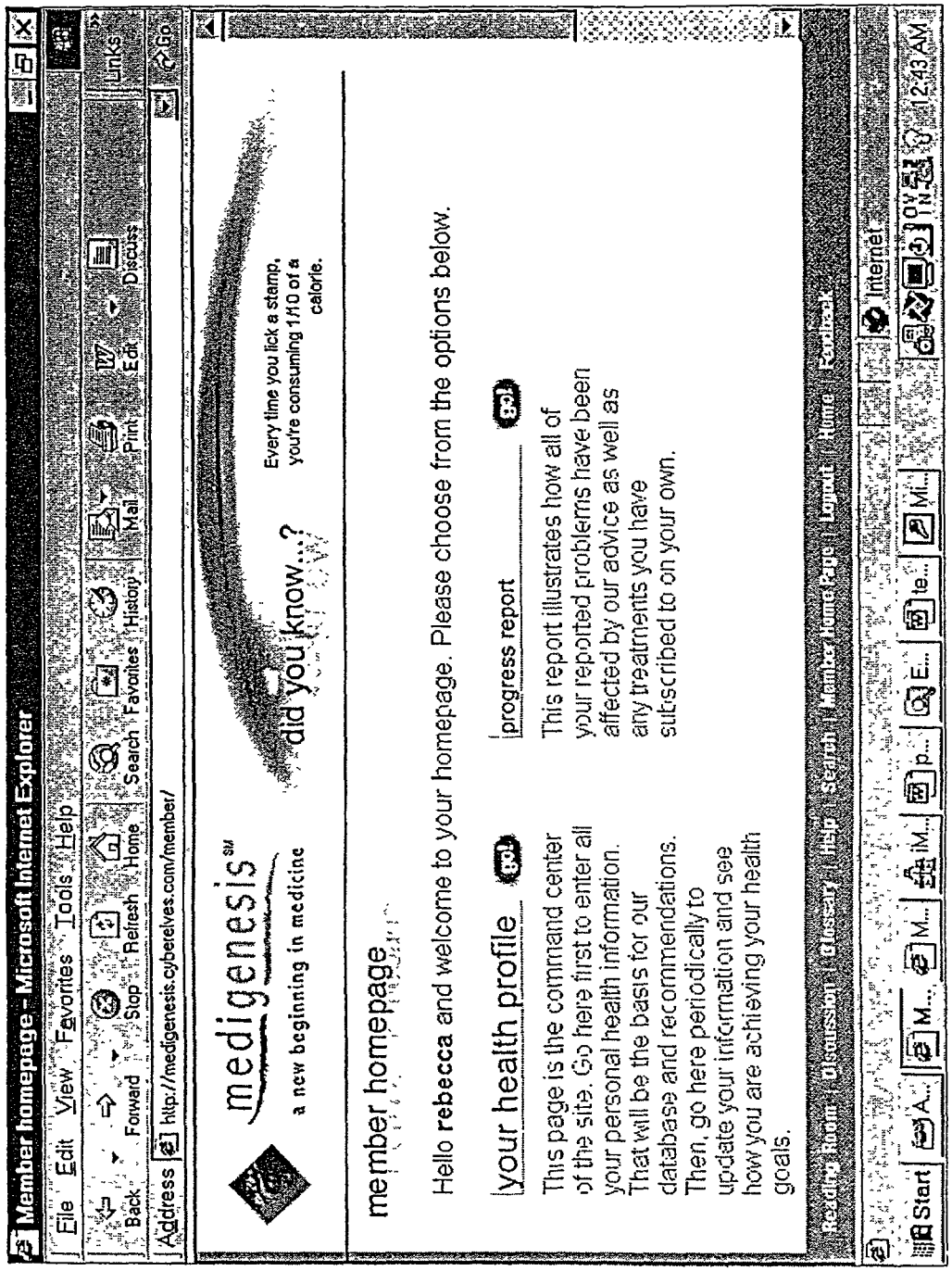
Figure 13:
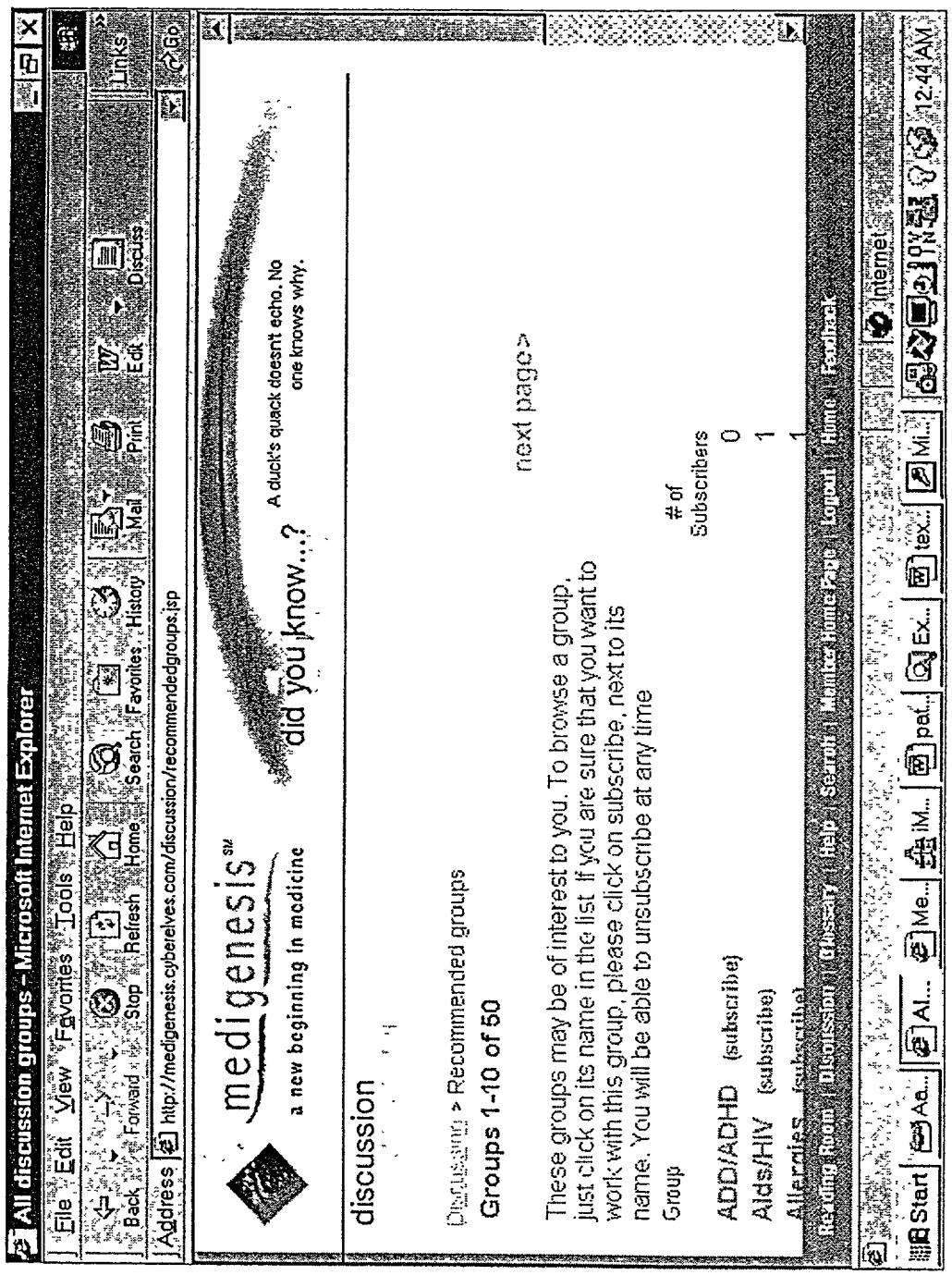
FIGS. 13 and 13A depict an exemplary "Recommended Groups" screen.
Figure 13A:
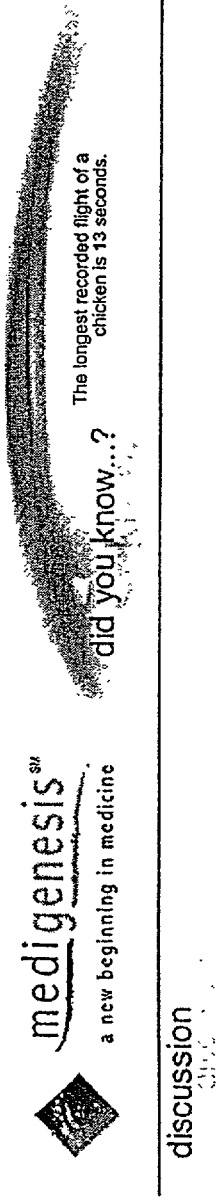
Figure 14:
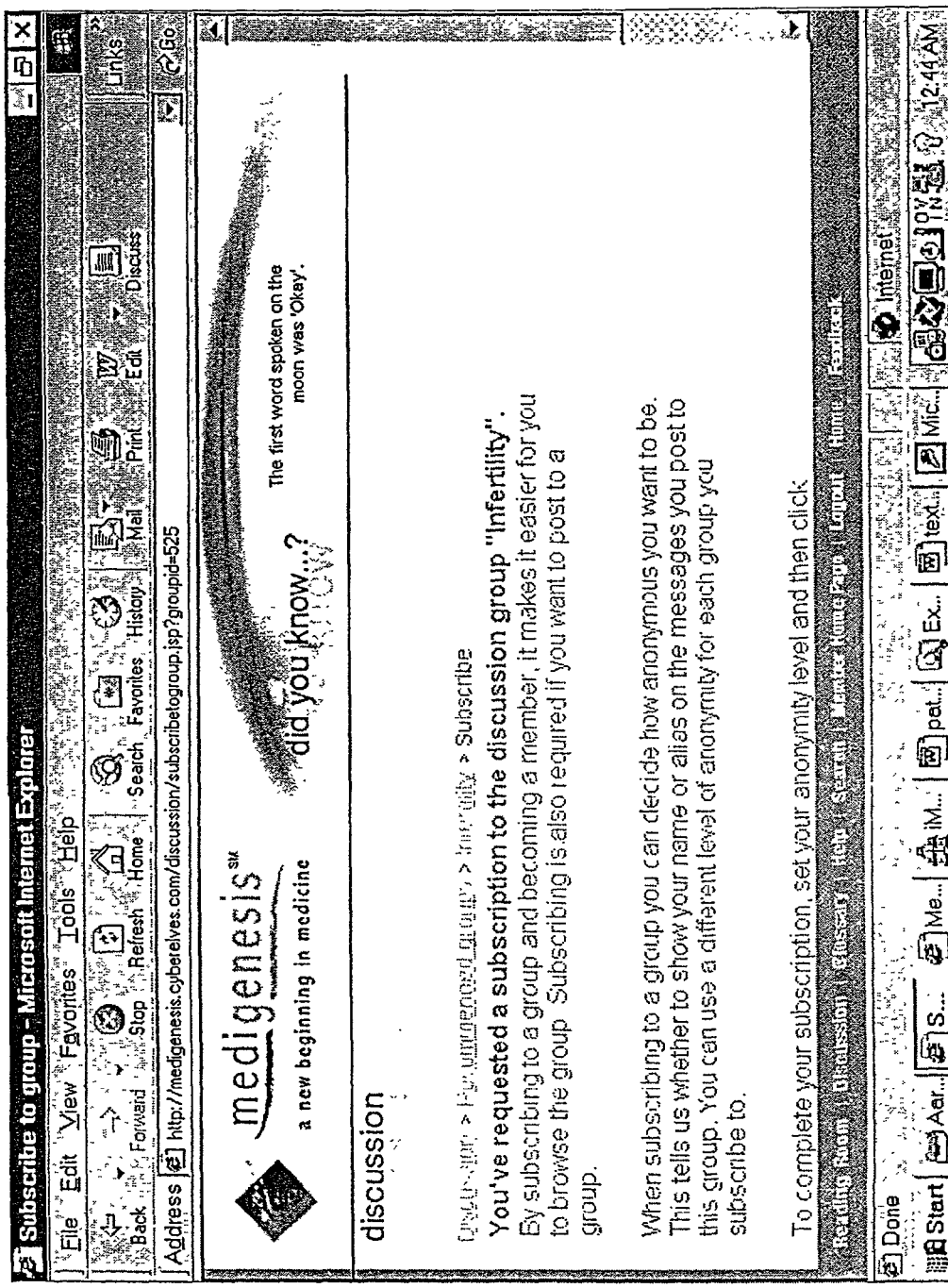
FIG. 14 depicts an exemplary "Infertility>Subscribe" screen.
Figure 15:
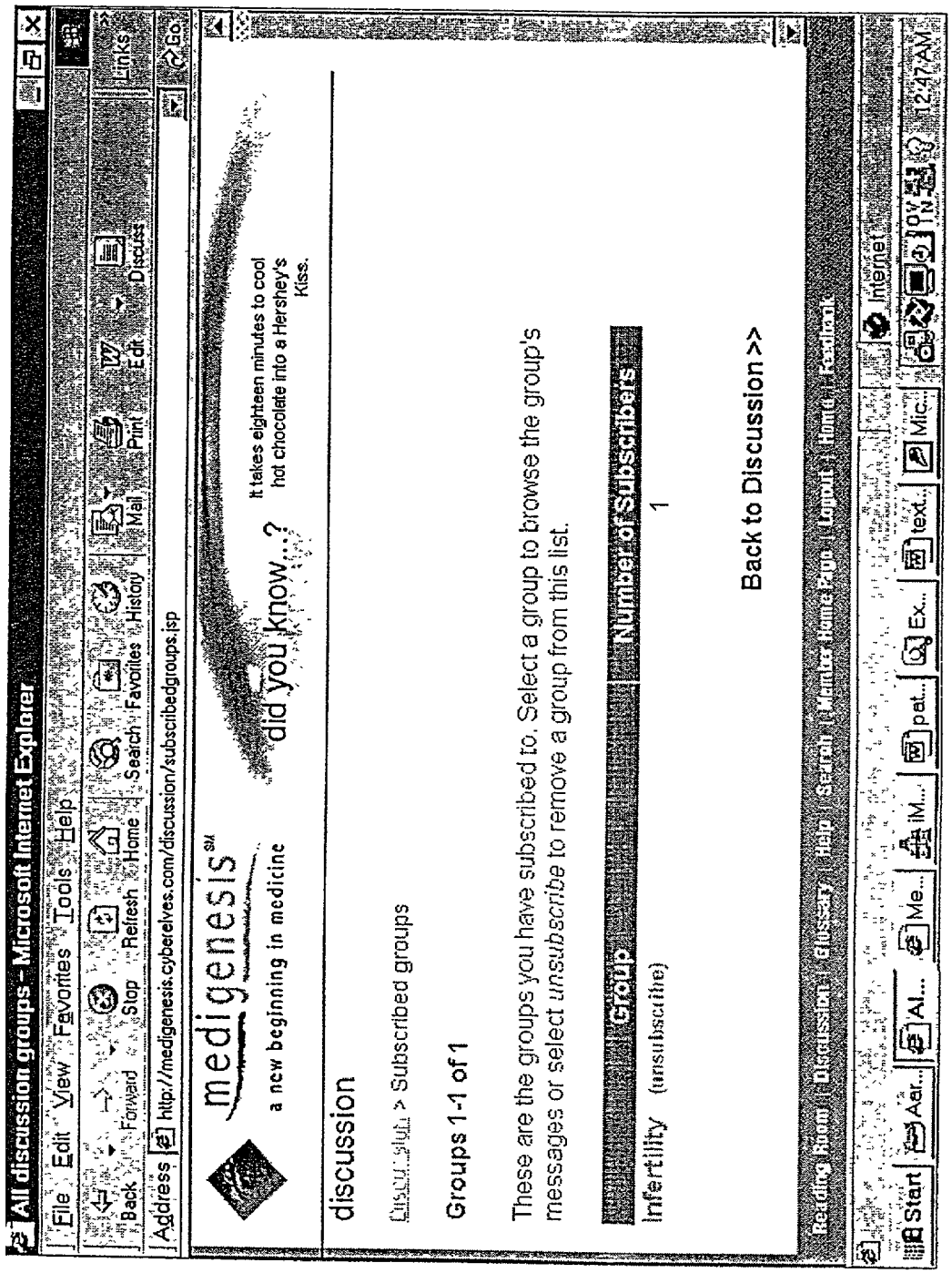
FIG. 15 depicts an exemplary "Discussion>Subscribed Groups" screen.
Figure 19:
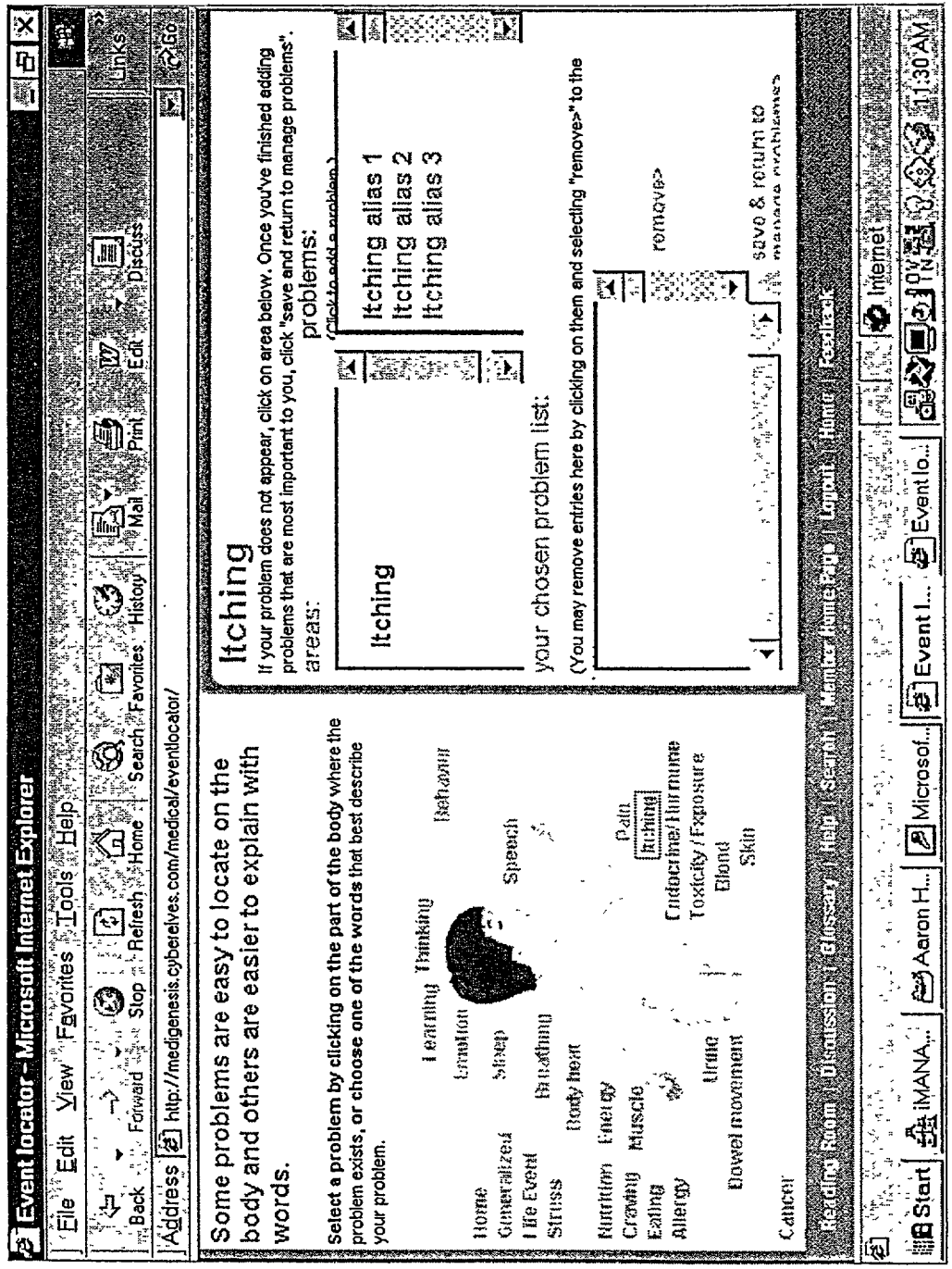
FIGS. 18-22 depict the "Event Locator", shown for an adult male user.

Clicking on button 104 accesses the Account Signup page, as shown in FIG. 4, and the New Member Information box appears as therein depicted. The user fills out the interactive box and receives access to the site. Button 105 leads to the What's News? page, as shown in FIG. 5, and button 106 leads to the Contact Us page, as shown in FIG. 6. Finally, button 107 leads to the Provider Resources page and subpages, as shown in FIGS. 7-7B. The menu bar, which is always at the bottom of the system screen, wherever one is in the system, will now be described, still with reference to FIG. 1. Menu Item 108 leads to the Reading Room, as shown in FIGS. 8 and 8A, Item 109 leads to the Discussion Area, as shown in FIGS. 9 and 9A. Item 110 leads to the Glossary, depicted in FIG. 10. Recall that one of the functions of the site and the system is to educate the user in the terms used to describe his or her health, so the glossary is quite an important tool. Item 111, Help, displays the help informational screen as shown in FIGS. 26-32.

Item 112 leads the user to a system search screen.

The critical interactions between the user and the system of the invention occur in the information acquisition phase, which occurs when the user, interacting with the system interface, describes his detailed state of health, the treatments he is taking, his primary and secondary problems, and the results of lab tests.

Figure 33:

The interface operates as follows. From the system Home page, shown in FIG. 1, upon clicking on the Member Home Page button 113, the user is taken to the Member Home Page, and sees the screen depicted in FIG. 33.

Upon clicking on the Your Health Profile button 3301, or the "go" sign to the right of it, the user is taken to the Your Health Profile page, and sees the screen depicted in FIG. 34.

Figure 35:
FIG. 35 is an exemplary depiction of the Member Information page.
Figures 41, 42:

There are six categories of information which can be entered and managed (i.e., edited) by the user at this page. Member Information, Treatments, Primary Problems, Secondary Problems, and Diagnostic Tests. The Medical Summary category cannot be edited, inasmuch as it represents the output from the system to the user, or for the benefit of the user's physician, but new summaries can be run by the user at any time, and are intended tobe run if any of the other data has changed. Clicking Member Information 3401 takes the user to that page, and displays the screen depicted in FIG. 35.

At this juncture the user can modify or add to any desired information that has already been stored, and then click at the button labeled Return to: Your Health Profile to return to the Your Health Profile page.

Figure 23:
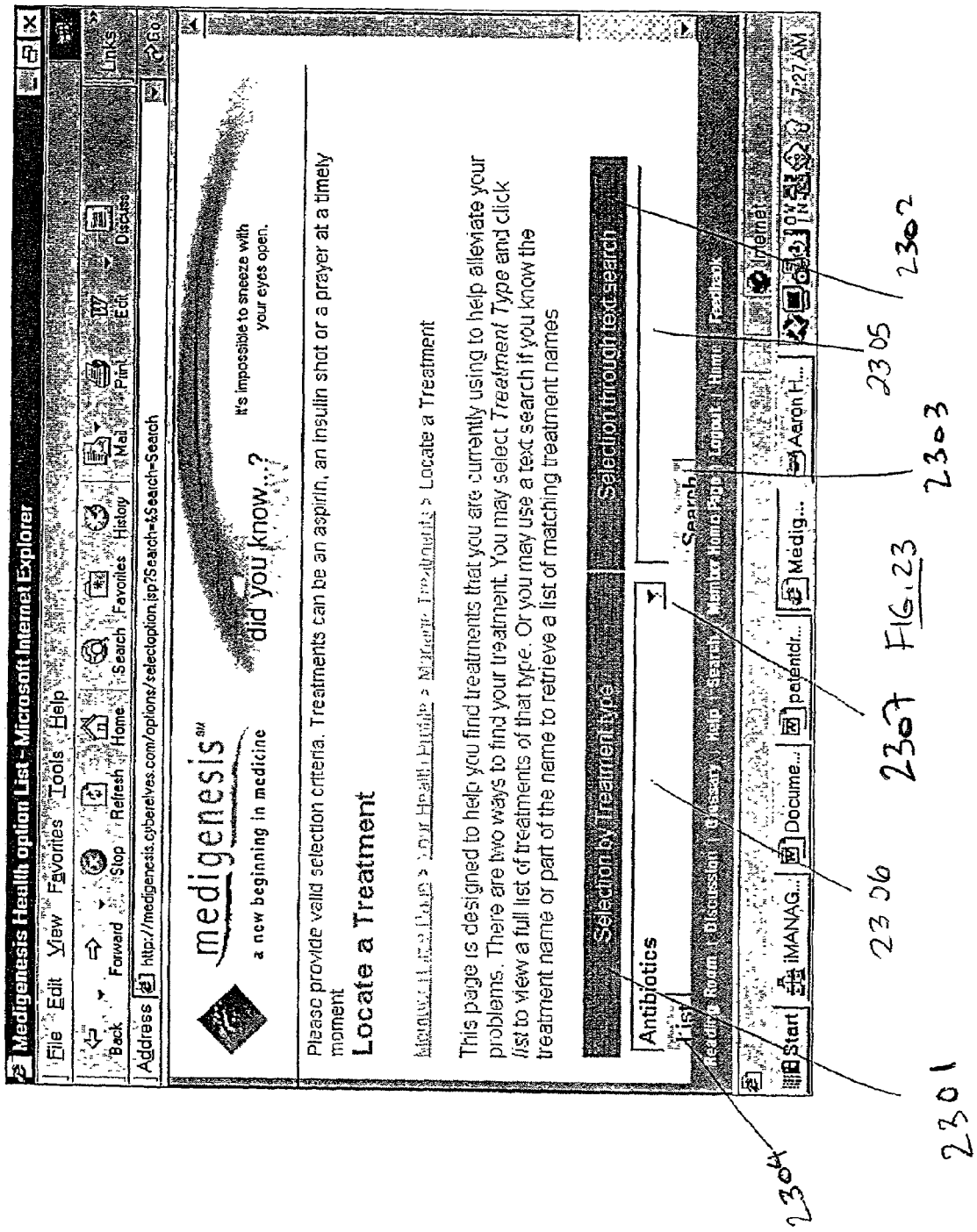
FIG. 23 depicts an exemplary "Locate a Treatement" screen.
Figure 24:
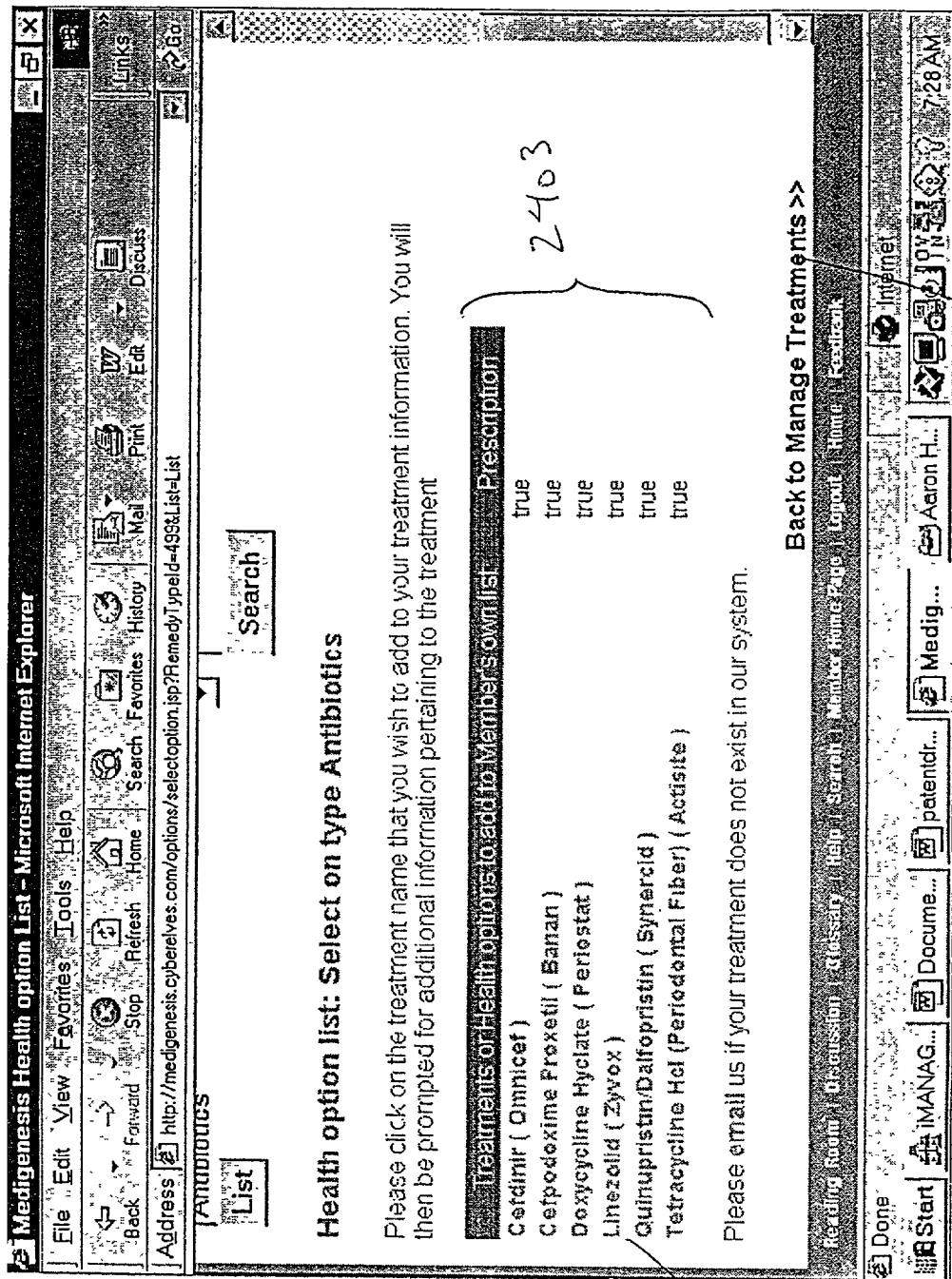
FIG. 24 depicts an exemplary "Locate a Treatment Screen" with a list of antibiotics displayed.

With regard to Treatments, listed as the second category on the Your Health Profile page, Clicking on Add Treatment brings the user to the Add Treatment page, and the text and interactive box appears as depicted in FIG. 36:

The function of this screen is for the user to tell the system database which treatments, meaning primarily medications, that he or she is currently taking. This information is necessary to obtain the true picture of the user's health. With reference to FIG. 23, the user sees the Locate a Treatment interactive box, and can either search for a treatment by typing in a text string in the type-in box 2305, or choose a treatment category 2306, by clicking the menu selector 2307, and clicking on the list button 2304. The latter action will bring up the Health Option List for the selected type, as in FIG. 24, where a list 2403 of the chosen type, here antibiotics, is shown. Clicking on a particular listed treatment, such as, for example, the antibiotic Zyvox 2402, brings the user to the treatment details screen.

Figure 25:
FIGS. 25 & 25A depict an exemplary "Treatment Details" screen.
Figure 25A:
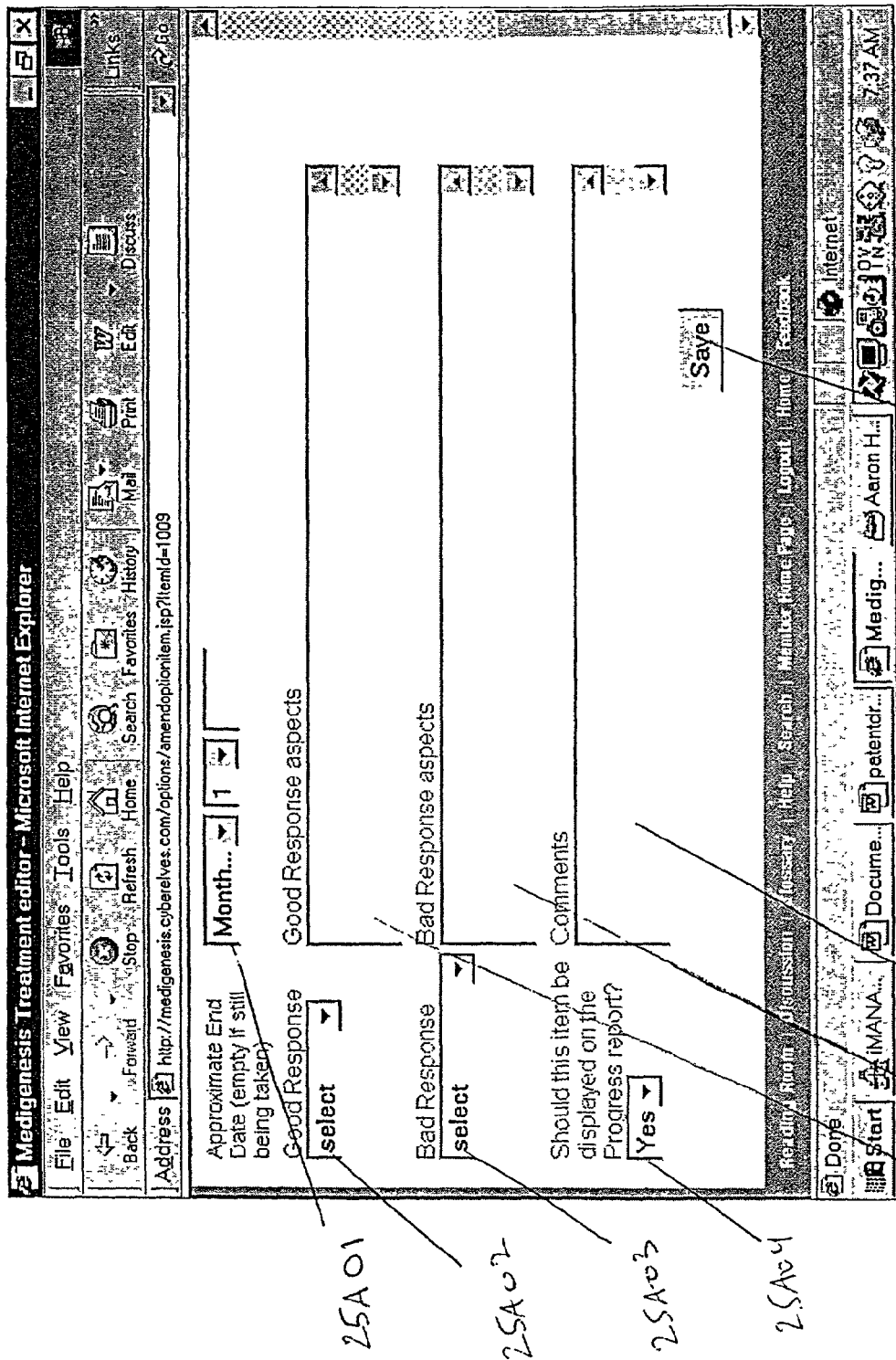
Figure 25B:
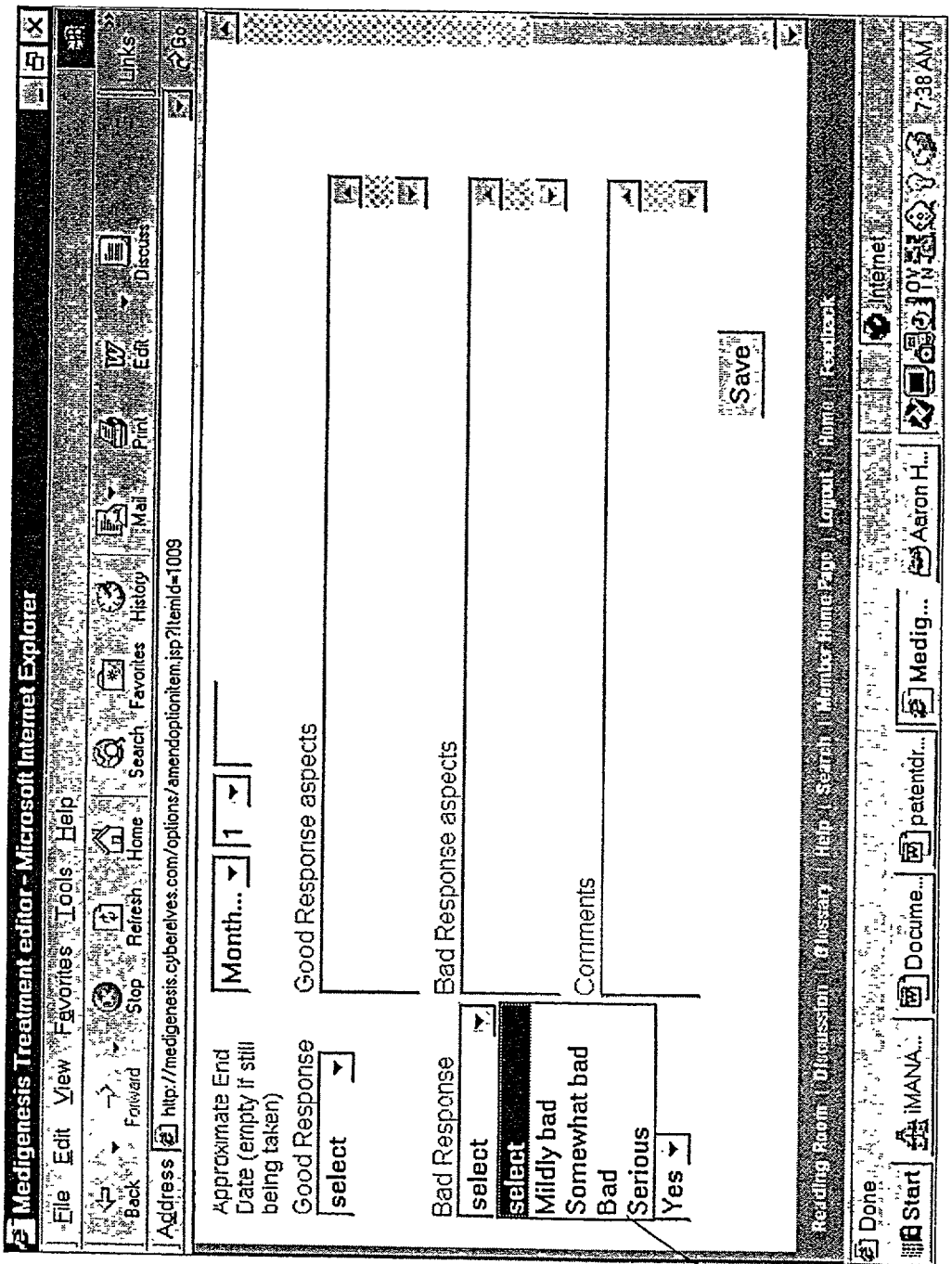

FIGS. 25-25B also depict this screen. Here, with reference to FIG. 25A, the user discloses the date the user stopped taking the medication 25AO1, the good response descriptor 25A02, or the bad response descriptor 25AO3, comments for either good or bad responses, 2SAOS and 2SAO6, respectively, whether the treatment should be displayed on the progress report 25AO4 and any further comments 25AO7. The information is saved by clicking on "Save" 25AO8. The response descriptors for good and bad are shown in FIG. 25B, in box 25BO1, and range from mildly bad (good), somewhat bad (good), bad (good), to seriously bad (good). After completing the information for the treatment, the screen depicted in FIG. 37 is next seen.

The user either adds a new treatment and repeats the process just described, or continues with the health profile of the six information categories found at the "Your Health Profile" page, the most important are the Primary Problems and the Secondary Problems. These will be next described in detail.

Figure 16:
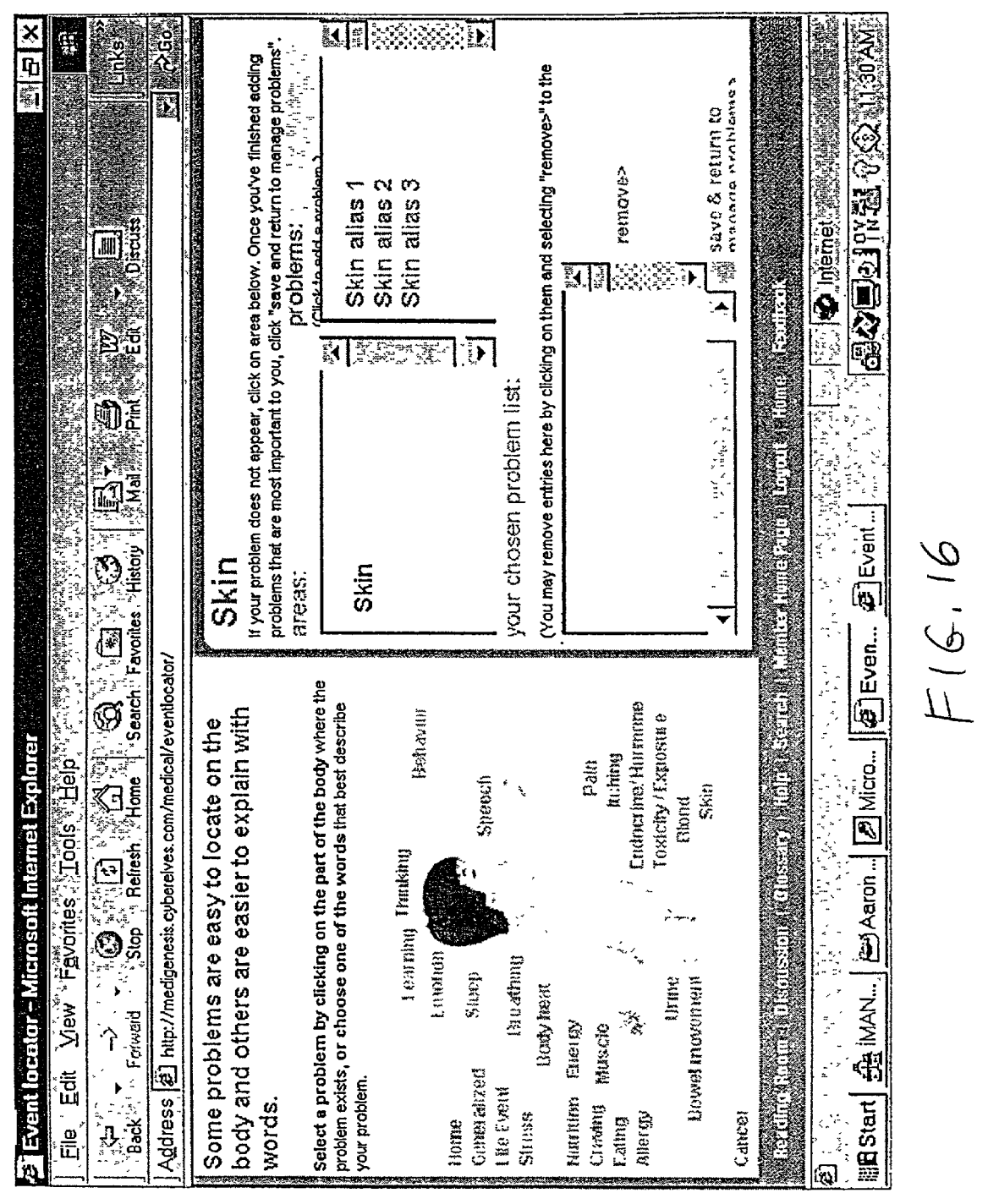
Figure 18:
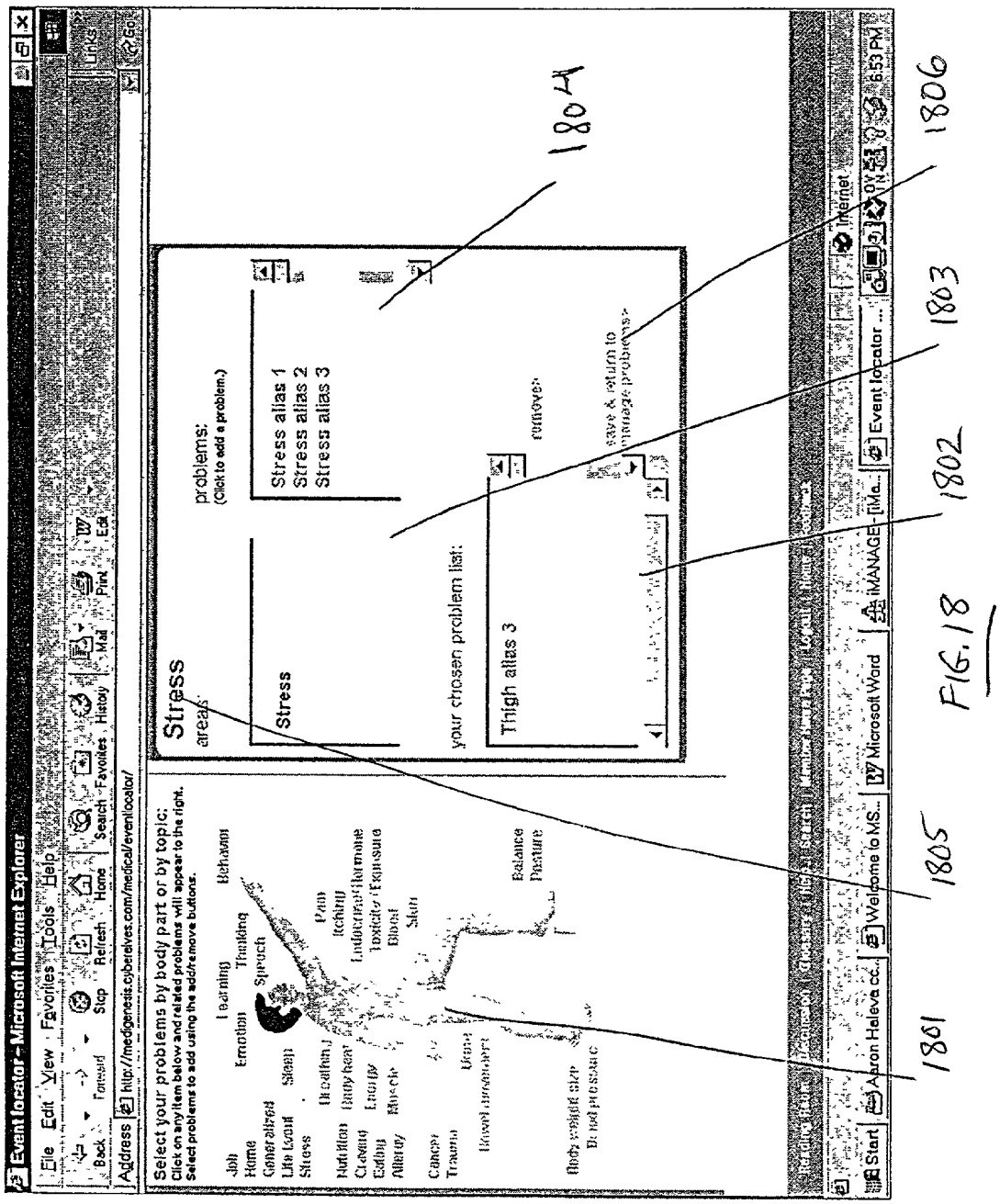
Figure 19:
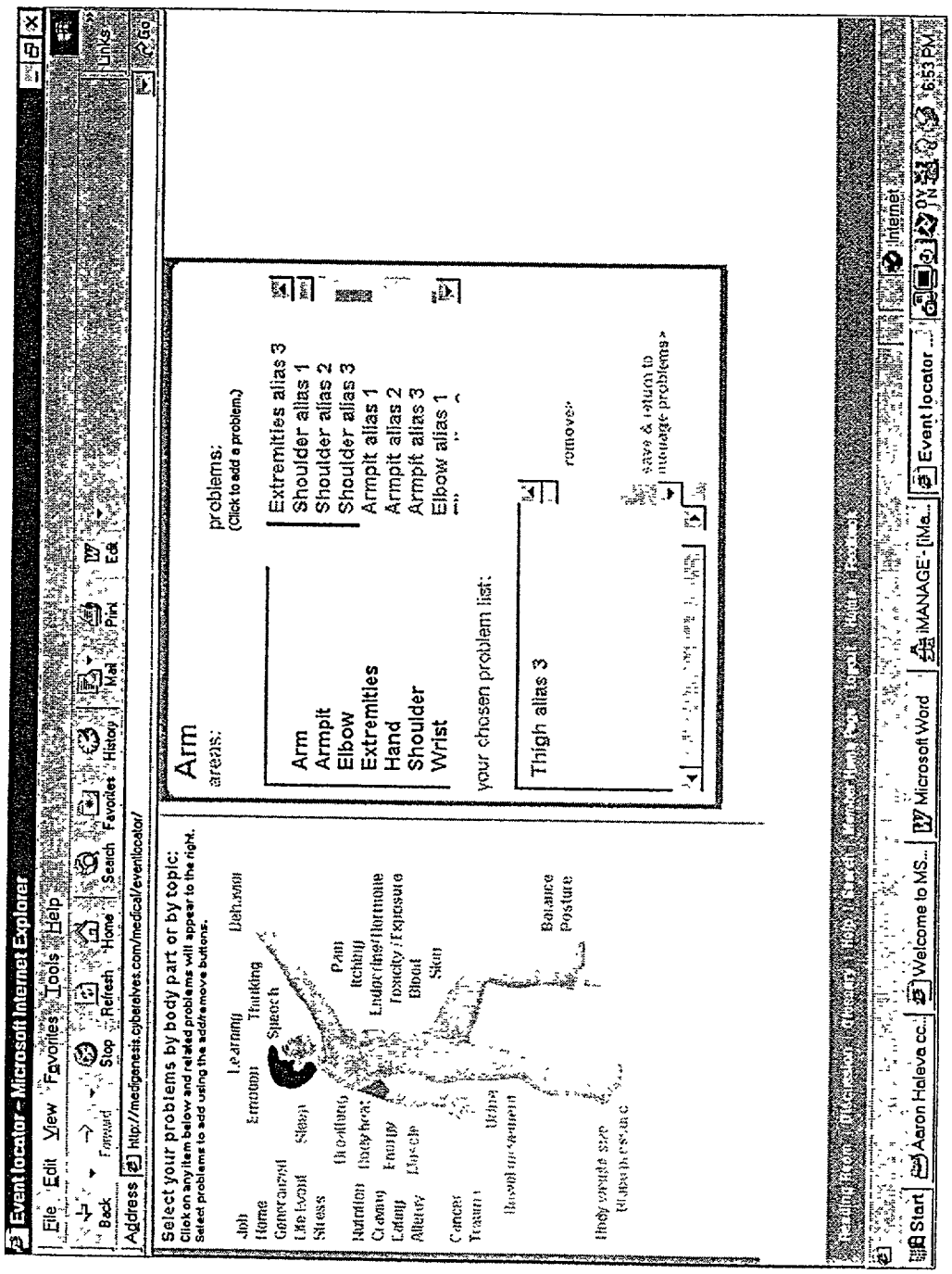
Figure 20:
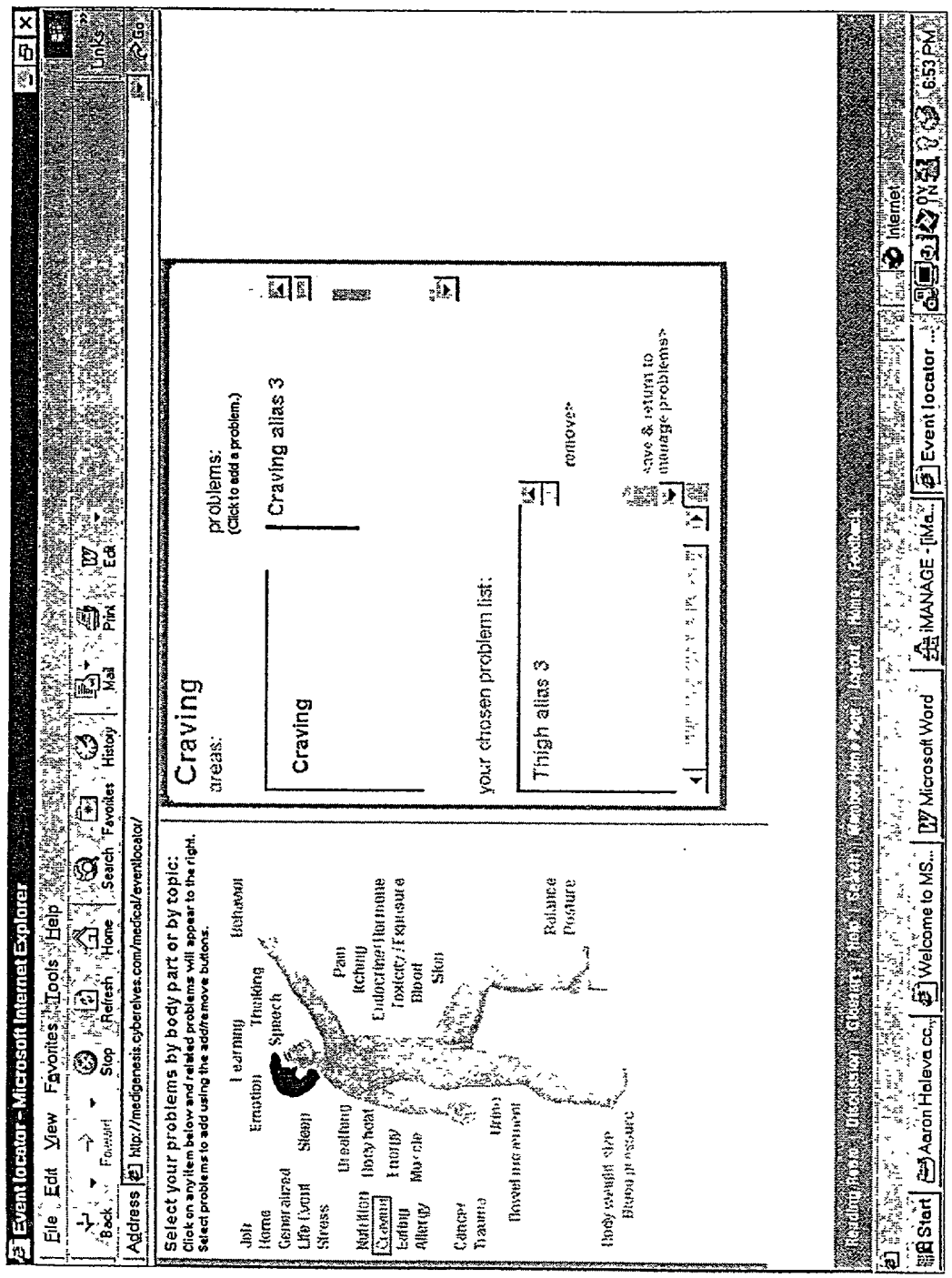
Figure 21:
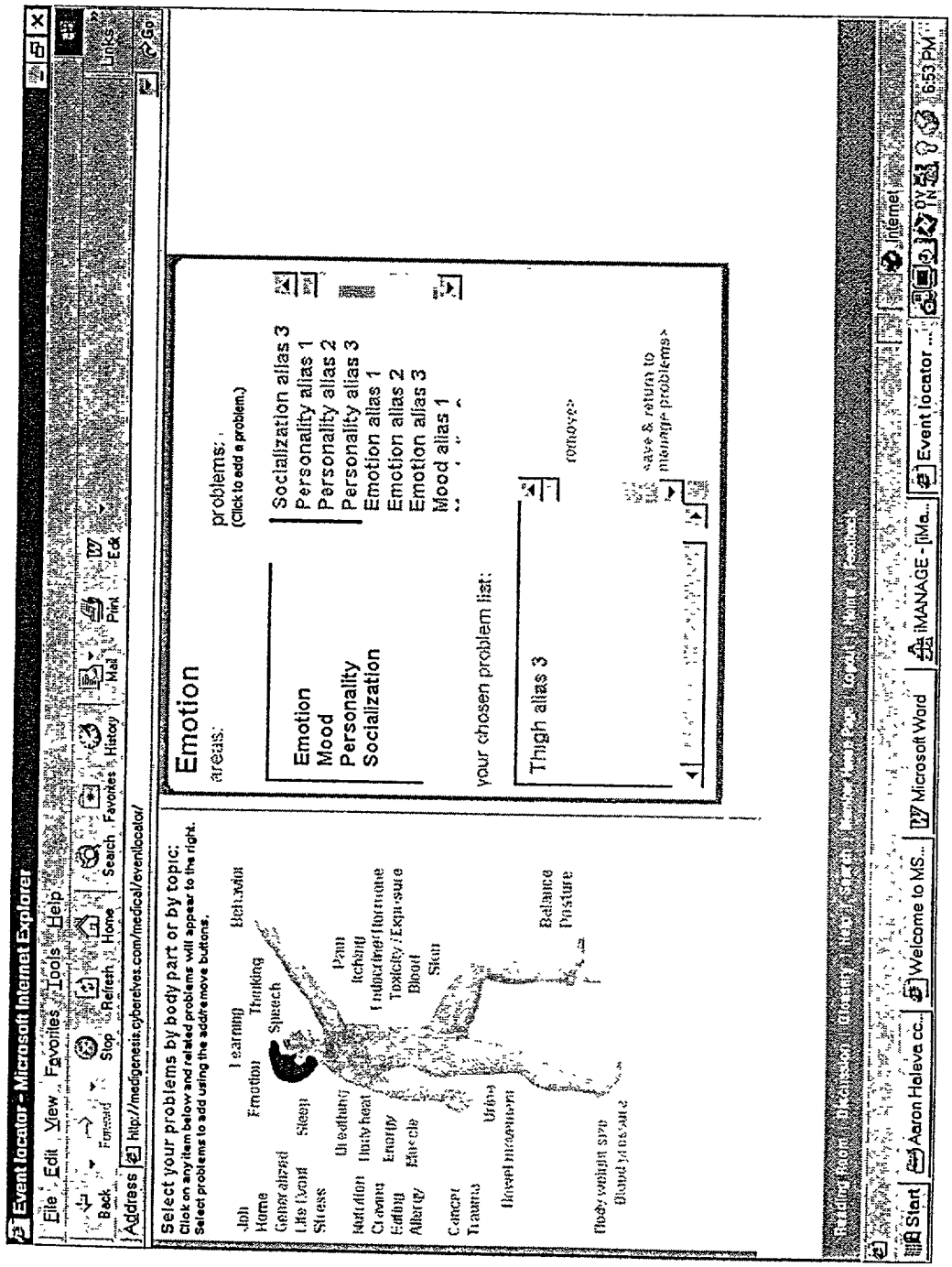
Figure 22:
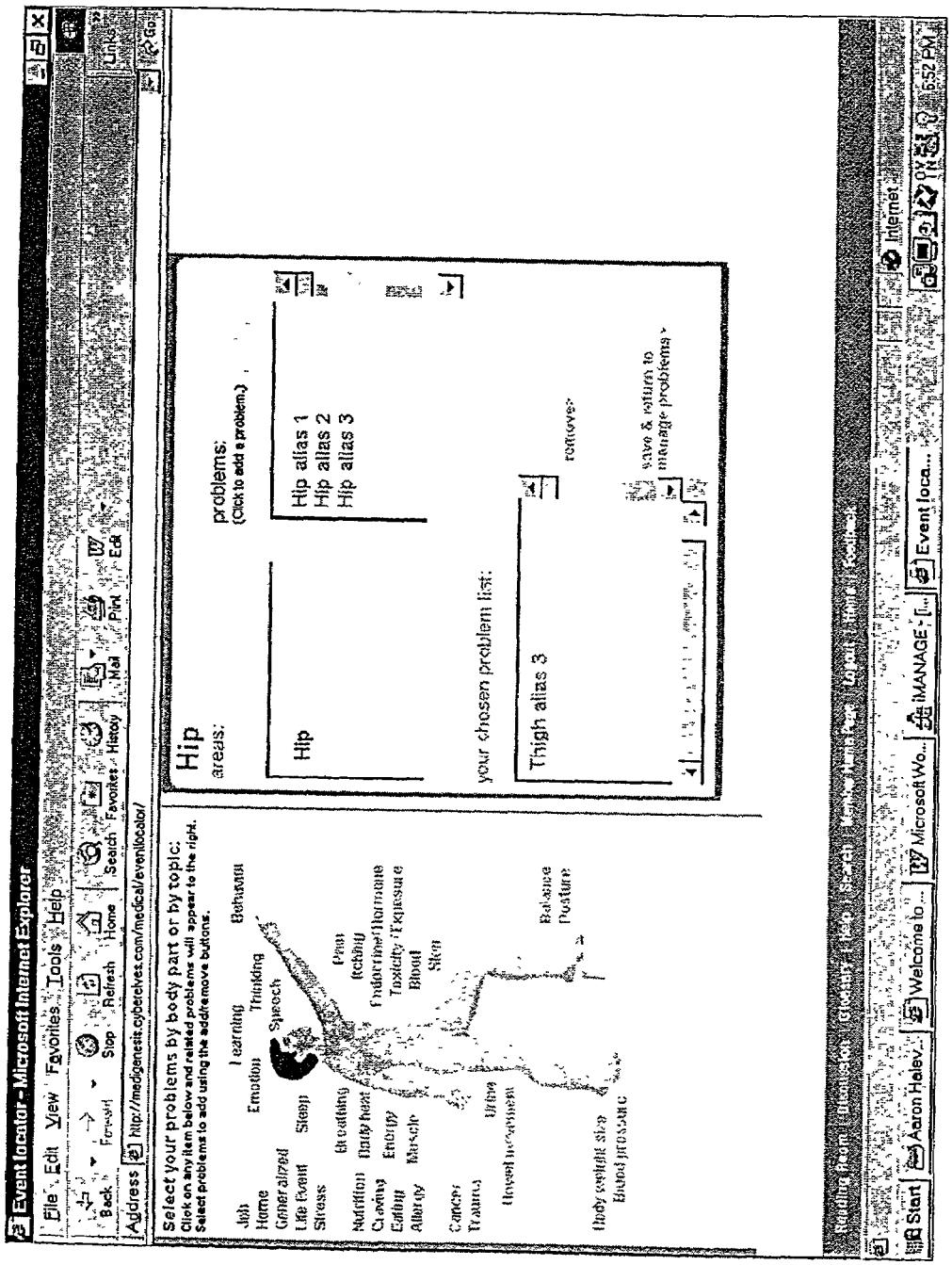

From the Your Health Profile screen a user accesses the primary problems screen by either clicking on the Add Primary Problem or the manage primary problem links. This takes the user to the Event Locator, as shown in FIGS. 16 and 17, for a young female child, and in FIGS. 18-22 for an adult male. The user clicks on the body of the Event Locator FIG. 1801 in FIG. 18, and a part of the body is highlighted. Alternatively, the user clicks on one of the words located around the figure. In either case the chosen body part or topic appears at the top 1805 of the interactive box on the right of the screen, and a list of "aliases" or sub categories of the chosen category appear for choosing and adding to the problem list shown in the Chosen Problem List box 1802. The user continues in this fashion until all the primary problems are chosen. The user then returns to the Your Health Profile page by clicking on the save and return button 1806, and sees the modified Primary Problems section as depicted in FIG. 37.

Secondary Problems are queried by an exhaustive questionnaire. Sample pages of the questionnaire are provided as Exhibit B-1. The questions seek to elicit the various problems a user has, and track the Exhibit A-1 set of all possible problems in all possible phrasings inherent in the system. As described above, the critical information gleaned is mapped to the SFWs and stored in the user's PDV.

Clicking on the "Run a new Medical Summary Report" link from section 5 of the Your Health Profile page generates a report, an example of which is shown in FIGS. 38-41. With reference to FIG. 1A, this is step 1A20. The report, inter alia, is characterized by an informational display similar to the following example text:

| Your Cluster[1] | | |
|---|---|---|
| Exact[2] | Similar[3] | 0% ... 100% | number of people in your cluster: 23
Defining symptoms in your cluster:

Within your cluster, the following
percentage of people have experienced
symptoms exactly like, or similar to your problems ...

| | | | |
|---|---|---|---|
| >>headaches[4] | 10% | 30% | (Bar Chart) |
| >>staph | 30% | 40% | (Bar Chart) |

Other people in your cluster also had ...

| | | |
|---|---|---|
| >>allergy to gluten[5] | 70% | (Bar Chart) |
| >>red hair | 60% | |

Treatments in your cluster

People within your cluster have reported good responses to ...

| | | |
|---|---|---|
| >>magnesium | 70%[6] | (Bar Chart) |

People within your cluster have reported bad responses from ...

| | | |
|---|---|---|
| >>trepanning | 20% | (Bar Chart) |

Common discussion forums for people in your cluster

If you wish to share information, or collaborate with others who are 'like you' then you will be interested to know the forums they are subscribed to:

| | | |
|---|---|---|
| >>staph infections forum | 70% | (Bar Chart) <<subscribe>>[7] |
| >>headaches forum | 20% | (Bar Chart) Already subscribed |

[1]This information is presented as part of the model report.
[2]This value indicates the percentage of members (in the cluster) having at least one event with the exact same formal problem id.
[3]This indicates the percentage of members (in the cluster) having at least one event which is 'simllar' to the event listed. Here similarity is defined as a match on the SFW record.
[4]The members chosen alias (as chosen on the Event Locator, Exhibit A-2, for example) is used to label the events listed in the rows here.
[5]Options listed here are those with more than one exact match (in the cluster) on formal problem id (but not shared by the member in question) - consequently, the formal problem name is used to label the events listed here.
[6]This gives the percentage of people within the cluster who have had good responses to this treatment. (Not the percentage of people who have taken the treatment who indicated a good response)
[7]Clicking the 'subscribe' link will take you to the default interface for subscription to a group.

Note that the report summarizes the reported problems, provides the benefit of the system's statistical analysis, and can even suggest, based upon such analysis, further diagnostic tests. As well, the report draws on all the information stored in the system, and not just that information encoded in the PDV.

Thus, if the user complies with the suggested diagnostic tests, assumably she will report the results of the diagnostic test to the system, generate a new medical summary report, and both she, and the knowledge inherent in the system, will obtain further useful information. Clicking on the Manage Diagnostic Tests link at section 6 of the Your Health Profile Page displays the screen shown in FIG. 42.

The system thus serves as the direct recipient of laboratory tests, and reports the results back to the user. Clicking on the link 4201 at the top right, or using the go button 4203 and menu bar 4204 returns the user to the Your Health Profile page.

To use a signal processing analogy, the bandwidth of the information acquired in the information acquisition phase is simply too great to be processed in real time by the information processor. Thus, for the purposes of generating a cluster, the signal is downsampled, and high frequency information is discarded. Once, however, the cluster is found, and computation does not require all the users in the system database to be operands to the processing algorithms, the bandwidth can again be increased to the original bandwidth, and all information, no mater how complex, available in the system regarding the user, and the other members of the cluster, is available for analysis in generating the user reports. With reference to FIG. 1A, the cluster 1A15, and all of its users' complete records, as well as the user's complete original records, collectively 1A16, are available as operands to the report generating algorithms.

Thus, once the cluster closest to the new user is arrived at, additional analysis such as data mining using association rules is employed to derive useful information for the nearest users, as above. One of the data mining techniques employed is the discovery of association rules. Association rules discover the correlations between attributes, such as the presence of a particular attribute implying the presence of other attributes for a user. As described above, for the sake of analytical tractability, many auxiliary dimensions, elicited in the user interface from the user, but not encoded in the SFWs, were omitted from the original clustering. These dimensions, such as aggravating factors, alleviating factors, etc. (see Exhibits A-1 and A-2) hold rich information that has, in the SFW encoding and cluster generation process, been unexplored.

An example of an association rule is that "whenever a patient has disease X, the common aggravating factor is wheat". For two sets of items X and Y, an association rule is usually denoted as x~y to convey that the presence of the attribute X in a vector implies the presence of Y. The role of associations would be complementary to clustering (once the clusters are determined, mining for association rules within the cluster provides useful information on the medical experiences of the clusters).

Primary Scenario

To summarize the operation of the system of the preferred embodiment, the flow of events, in the usual case, is as follows.

1. A member accesses the system, and completes the steps in the Your Health section. (Detailing their Primary Problems, Treatments, and taking the Questionnaire, all as described above).
2. The User (Member) chooses to generate a new Report.
3. The original User's record is mapped to a PDV, based on the medical information that the user has entered. This discards some information in the User's record for the purposes of generating the cluster.
4. The PDV, and supporting user choices from the Exhibit A-1 list, as well as the formal problems of the A-2 list that the A-1 list choices are mapped to, is stored for later retrieval.
5. The PDV is compared against all existing PDVs in the database to find a cluster of members (users) who are 'close' to this member.
6. Queries are generated against the top 'n' members to determine their most common discussion groups, defining problems and good/bad treatments. All available information in the system is used at this stage.
7. This information is presented to the user in a table, or other meaningful and efficient formats.
8. Reports can be sent electronically, or via hard copy, to a User's doctor or other designated parties. FIG. 1A30.

Event Locator and Questionnaire Design Issues:

The design issues behind, and the functionalities of, the Questionnaire, will next be discussed.

The capacity of databases to permit new methods of viewing patterns of information and finding matches is not worth much without ways to capture accurate, detailed, and structured input.

The user is the original, most reliable and most efficient source of most information about symptoms, life events, environmental exposures, past illness, operations, allergies, and family history. The user has a story—referred to medically as the medical, social, environmental, family history. The system database has rows and columns waiting to receive the story. The interface between the input and storage of this data fulfills the following criteria:

1. Engaging;
2. Intuitive;
3. Uses everyday language;
4. Codes the data on entry.

Questionnaires in current medical use have narrow or superficial areas of interest in information that can expand in the context of a personal interview. There does not now exist a method for the free-form capture of detailed coded data in a system that begins with the same kind of question one would ask when sitting down with a patient for the first time: "Please tell me what is bothering you?" The Event Locator (FIGS. 16-22, and the listings in Exhibit A-1 which can all be addressed in the Event Locator and/or follow up Questionnaire) starts from that point and leads to a questionnaire that follows up on symptoms and other events captured in the event locator, as described above.

A database providing vernacular descriptions of most medical symptoms and events matched to their coded dimensional meanings provides the foundation for the preferred embodiment of the present invention's capacity to encode natural language descriptions.

The present invention's first device is a graphic representation of a figure corresponding to the user's gender and age group (adult, child, toddler). The screen presented to the user shows the figure on the left. See FIGS. 16-22. Moving a mouse over the figure, the user sees the names of various body areas or organs pop up in text boxes (leg, liver, intestines, nose, face, etc) and a mouse click then gives the user a list in one of the three boxes on the right side of the screen the top 15 symptoms associated with that area (precisely, it is the upper left hand box on the right half of the screen, labeled "areas").

The user finds that selecting a small area (e.g. nose) will produce a list of problems whose associations are restricted to the nose, whereas selection of face will beget a list that includes nose problems along with eyes, mouth, chin, lips, etc. A substantial subset of symptoms can be addressed simply by reference to a part of or place on the body. Other problems may be identified by identifying the function (e.g. pain, itching) or the cause (allergy, trauma) of the symptom to be described. Thus a user with a headache may click on "pain," or "head" to reach a list from which his or her type of headache can be selected. A person with itching on the elbows and knees may select "itching" or click first on elbows and then knees bringing them sequentially to elbow itching and knee itching.

All possible primary events in the invention's database can be found by at least one, and usually several redundant clicking choices. A primary event is one that is susceptible of being considered as a problem that would be described in response to the question, "Please tell me what is bothering you" and which would then populate the primary problem list. Thus the user can locate all sorts of trauma, allergies, pains, itching, and other disturbances of function as well as important toxic exposures and life events. Linkage of all the symptoms is assured by a table maintained in the database denoting which symptoms are grouped under subgroups (e.g., nose) and bigger groups (e.g., face). The following options appear after the top 15 symptoms (associated with the user designated area, function or trauma) list appears on the right side of the screen:

1. The user may select a symptom from the list.
2. The user may expand the list to include all the choices (i.e. beyond the top 15) in a scrollable enlargement of the top 15 list.
3. The user may compact the symptom list by clicking to its left, on the human figure, on a location (e.g. nose, ear, mouth) representing a narrowing of the choices in a bigger groups (e.g. face). Similarly, for say, Life Events, the user may narrow its list by choosing the type of Life Event he or she wishes to select as a primary problem (death, job change, family change).

The user adds a problem to his or her primary problem list by clicking on the words that best describe one of his or her difficulties. The process may be repeated until the user has described all symptoms and events.

Once the graphic device has permitted the capture of the free form aspect of a medical interview in which the top of the user's problem list can be obtained thanks to the users incentive to input his or her main problems the user moves to the primary problem list screen for rating (assigning a numerical value representing the relative importance of each problem to the user), scoring (indicating whether the symptom is milder moderate severe, or variable in its intensity) and describing (with drop down table choices) the onset, frequency, and episodic duration (when you get the headache how long does that episode last?) of each problem.

After the primary problems have been dealt with, the system moves the user on to describing her secondary problems. As described above, this occurs via the medium of the questionnaire.

The Questionnaire

The questionnaire allows for an inventory of other remaining difficulties that add detail to the sketch of primary problems and thus results in a true portrait of the user's unique combination of symptoms (events) stored in a manner that allows it to be matched with other individuals in the database as they are represented by statistical clusters. The key to the questionnaire is its presentation of branching, from general questions such as "Do you have any muscles spasms, tics, cramps, or tension?" to a specific list of symptoms that fall naturally into such a group. Questionnaire logic that recognizes symptoms entered in the primary problem list acknowledges previous answers ("We see that you have problems with headache; please tell us more about the factors influencing your headaches"), or builds from previous responses: ("We see that you have itchy elbows, please tell us if you have other itches that are important.")

The lexicon or taxonomy referred to above, i.e. the listings of Exhibit A-1 is the foundation of the questionnaire. The lexicon gives the invention the capacity to exchange information with users in a language that is at the same time vernacular, yet coded in ways that preserve the detailed individuality of each user. Unlike a paper questionnaire, in which the device of e.g., "If 'no' skip to question 161", has obvious limitations to one level of logical branching, an Internet or other data network accessed questionnaire has the capacity for many layers of branching that permit drilling down from a very general question. For example, from the general question "Do you have any skin problems or changes of any kind in your skin?" to (if yes) a group of more specific header questions which (if yes) permit the presentation of very specific skin symptoms. The more specific skin header questions have been formulated so that the vernacular terms used reflect the realities of medical dialog while their clusterings within each header question reflect functional (pain, itching, disruption, dryness) distinctions allowing for the specific questions at the third layer of branching to be of the same general type.

The questions found in an example questionnaire cover all of the issues contained in the Exhibit A-1 listing. The preferred embodiment has approximately 7400 of them. Primary Problem categories are asked to nearly everyone, termed "header questions", and specific follow ups only to those indicating the presence of the problem. In this manner, the system "drills down" from the general to the specific, and thus hones in with great detail on the user's particular problems. Exhibit B-1 contains sample pages from the on screen version of an example questionnaire as seen by a user, depicting the skin header (or general) questions.

The skin header questions (Exhibit B-1), show how a complete inventory of skin questions was built from the lexicon by grouping words commonly expressed by patients to describe related problems.

Muscular problems provide another example of the way that the data in the database generates the terms used in the questionnaire. The question: "Do you have any tics, cramps, twitches, spasms, or muscle tension?" is a concatenation of terms joined by the functional pathology having to do with an abnormal increase in the normal function of muscles, to contract. It would not, however, due to ask a patient "Do you have an abnormal increase in the tendency of your muscles to contract?", because that description is too far from the vernacular. On the other hand, to design a questionnaire entirely on the basis of being able to think up all the variations of how people express such categories of symptoms without reference to a lexicon of how they actually did so would be impossibly tedious. With each question the user is presented with the appropriate modifiers of severity, onset, frequency, episodic duration, and overall duration (for problems that ended in the past).

After completing the questionnaire, the user may promote problems uncovered in the questionnaire process to be primary problems if he or she appreciates during the questionnaire process that such and such a problem is, in fact, of sufficient concern to be rated among the ones that he or she mentioned in the primary problem phase (Event Locator, FIGS. 16-22).

Coding Examples

In what follows, examples of possible coding are presented to illustrate one implementation of key system computational functionalities. Numerous variations are obviously possible, and the following examples are for illustration only, and in no way are intended to limit or restrict the multiplicity of possible embodiments of the invention covered by the claims.

The key steps of the preferred embodiment are:
1—Calculate the weightings matrix W;
2—Generate a PDV for a particular member;
3—Calculate medical similarity of this PDV to the other members; and
4—Find the cluster of nearest N members (dynamic calculation based upon moving averages not shown; considered a trivial extension of the example depicted given the discussion in the specification above).

1. Calculate Weightings Matrix

This is done as a two step process:

Firstly the following code runs as a stored procedure and creates the 'first pass' approximation for the most common cases. Basically it gives a weighting of 1 if only s,f, or w are shared between two columns. 2 if two things are shared and 3 if all three are shared (ie they are the same column).

```
<CODE>
insert into clusterweightings
    select c1.clusterColumnId, c2.clusterColumnId,
        case
            when (sfw1.systemId = sfw2.systemId and
                sfw1.functionId = sfw2.functionId and
                sfw1.whereId = sfw2.whereId)
            then 3
            when ((sfw1.systemId = sfw2.systemId and
                sfw1.functionId = sfw2.functionId) or
                (sfw1.functionId = sfw2.functionId and
                sfw1.whereId = sfw2.whereId) or
                (sfw1.systemId = sfw2.systemId and
                sfw1.whereId = sfw2.whereId))
            then 2
            else 1
        end
    from (clusterColumn as c1 inner join sfw as sfw1 on
c1.sfwid = sfw1.sfwId)
    cross join
        (clusterColumn as c2 inner join sfw as sfw2 on c2.sfwid =
sfw2.sfwId)
        where sfw1.systemId = sfw2.systemId or
            sfw1.functionId = sfw2.functionId or
            sfw1.whereId = sfw2.whereId
</CODE>
```

Then, to refine the weightings matrix we pass over the columns again using VB code, the purpose of which is to deal with the situation that different Systems, or Functions , e.g. CNS and Behaviour are actually somewhat related, and should have some "closeness" score.

updateSystemSFW("X", "X", 1) for all columns that have the same system, i.e. "X" in two different columns.

The last stage downgrades the weight (by 1) when the where value that is shared is "not specified" (as opposed to e.g. "leg").

```
<CODE>
Call updateSystemSFW("CNS", "Behavior", 0.8)
Call updateSystemSFW("Craving", "Behavior", 0.6)
Call updateSystemSFW("Development", "Behavior", 0.6)
Call updateSystemSFW("Emotion", "Behavior", 0.8)
Call updateSystemSFW("Neuromuscular", "Behavior", 0.2)
Call updateSystemSFW("Speech", "Behavior", 0.4)
Call updateSystemSFW("Vascular", "Blood", 0.2)
Call updateSystemSFW("Metabolic", "Blood chemistry", 0.4)
Call updateSystemSFW("Digestive", "Body weight", 0.4)
Call updateSystemSFW("Metabolic", "Body weight", 0.4)
Call updateSystemSFW("Nutrition", "Body weight", 0.2)
Call updateSystemSFW("Vascular", "Cardiovascular", 0.6)
Call updateSystemSFW("Development", "CNS", 0.4)
Call updateSystemSFW("Emotion", "CNS", 0.6)
Call updateSystemSFW("Hearing", "CNS", 0.2)
Call updateSystemSFW("Immune", "CNS", 0.4)
Call updateSystemSFW("Neuromuscular", "CNS", 0.2)
Call updateSystemSFW("Speech", "CNS", 0.4)
Call updateSystemSFW("Vision", "CNS", 0.2)
Call updateSystemSFW("Eating", "Craving", 0.8)
Call updateSystemSFW("Emotion", "Craving", 0.4)
Call updateSystemSFW("Metabolic", "Craving", 0.2)
Call updateSystemSFW("Nutrition", "Craving", 0.6)
Call updateSystemSFW("Life Event", "Development", 0.2)
Call updateSystemSFW("Eating", "Digestive", 0.8)
Call updateSystemSFW("Exocrine", "Digestive", 0.2)
Call updateSystemSFW("Immune", "Digestive", 0.4)
Call updateSystemSFW("Nutrition", "Digestive", 0.6)
Call updateSystemSPW("Emotion", "Eating", 0.2)
Call updateSystemSFW("Nutrition", "Eating", 0.8)
Call updateSystemSFW("Metabolic", "Endocrine", 0.6)
Call updateSystemSFW("Reproductive", "Endocrine", 0.6)
Call updateSystemSFW("Metabolic", "Energy", 0.6)
Call updateSystemSFW("Warmth", "Energy", 0.4)
Call updateSystemSFW("Skin", "Hair", 0.6)
Call updateSystemSFW("Immune/lymph", "Immune", 1)
Call updateSystemSFW("Warmth", "Metabolic", 0.4)
Call updateSystemSFW("Skin", "Nails", 0.6)
Call updateSystemSFW("Skeletal-joint", "Neuromuscular", 0.2)
Call updateFunctionSFW("Abnormal color", "Abnormal", 1)
Call updateFunctionSFW("Abnormal growth", "Abnormal", 1)
Call updateFunctionSFW("Abnormal lab test", "Abnormal", 1)
Call updateFunctionSFW("Abnormal odor", "Abnormal", 1)
Call updateFunctionSFW("Abnormal PE", "Abnormal", 1)
Call updateFunctionSFW("Abnormal rhythm", "Abnormal", 1)
Call updateFunctionSFW("Abnormal sensation", "Abnormal", 1)
Call updateFunctionSFW("Abnorrnal sound", "Abnormal", 1)
Call UpdateNotSpecifiedWhere (1)
</CODE>
```

2. Generate PDV for a Particular Member

This is all implemented in a class called "BoundedPDv.java." The method works as follows:

```
<CODE language="java" doctored="heavily doctored">
public void generatePdvColumns( ) throws DomainException {
    getPdvColumns( ).clear( );
    generateGenderColumns(memberId);
    generateAgeColumns(memberId);
    generateSfwColumns(memberId);
}
/** retrieve gender information from member
 * object and update corresponding columns */
private void generateGenderColumns(Long memberId) throws
DomainException {
    Member member = new Member(new MemberIdKey(memberId));
    String gender = member.getGender( );
    if ("m".equalsIgnoreCase(gender)) {
```

-continued

```
            Long columnId = new Long(MALE_COLUMN_ID);
            setColumn(columnId, 1);
            return;
    }
    if ("f".equalsIgnoreCase(gender)) {
            Long columnId = new Long(FEMALE_COLUMN_ID);
            setColumn(columnId, 1);
            return;
        }
        Log.write(Log.ERROR,"could not determine gender of
member, got gender:" +
gender + " for memberId" + memberId + "- continuing
silently", this);
        }
        /** retrieve age information from member
         *  object and update corresponding columns */
        private void generateAgeColumns(Long memberId) throws
        DomainException {
        Member member = new Member(new MemberIdKey(memberId));
        int maxAge = NUM_AGE_COLUMNS*YEARS_IN_AGE_BRACKET; //
15*7=105
        int lastAgeColumn = NUM_AGE_COLUMNS+FIRST_AGE_COLUMN-1;
//15+3-1=17
(columnId,17) at the mo
        int age = member.getAge( ).intValue( );
        // find the highest age bracket in which the member
        // exceeds minimum age
        int bracketMin = maxAge;
        for (int columnId=lastAgeColumn;
columnId>=FIRST_AGE_COLUMN; columnId--) {
            bracketMin=bracketMin-YEARS_IN_AGE_BRACKET;
            if (age>=bracketMin) {
            // NB.. if older than maxAge, they end up in the
highest bracket
            setColumn(new Long(columnId),1);
            return;
            }
        }
        }
/** call a stored procedure (for speed)
 *  to get the columns relating to SFW information, calculate
 *  corresponding value and call setColumn to update into
pdv column list
*/
        private void generateSfwColumns (Long memberId) throws
DomainException {
            String retrieveQuery = "{call
cluster_event_seventies_sp(" + memberId + ")}";
        while (resultSet.next( )) {
            rowCount++;
            // retrieve the severity info
            int i = resultSet.getInt("i");
            int j = resultSet.getInt("j");
            int k = resultSet.getInt("k");
            int l = resultSet.getInt("l");
            // calculate value for column from these
severities
            // lose accuracy at this, the last point, in
equation
            float value = (float)calculateSfwValue(i, j, k, l);
            // and update/add this value into pdvColumnList
            Long columnId = new
Long (resultSet.getLong("columnId"));
            setColumn(columnId, value);
            }
        }
        // calculate these values once per each initialisation
of the instance
    private double aInv=1/ClusterParam.a;
    private double bInv=1/ClusterParam.b;
    private double cInv=1/ClusterParam.c;
    private double dInv=1/ClusterParam.d;
    private double calculateSfwValue(int i, int j, int k,
int l) throws
DomainException {
    return 1 + ClusterParam.upperB * (1- (Math.pow(aInv, i)
* Math.pow(bInv, j)
*Math.pow(cInv, k) *Math.pow(dInv, l)));
    }
```

```
}
</CODE>
for completeness the stored procedure which gets
the severity i, j, k, l for the member's events
is defined as follows:
<CODE language="TSQL">
CREATE PROCEDURE cluster_event_severities_sp
(
    @MemberId INT
)
AS
DECLARE
@num_mild        int,
@num_moderate    int,
@num_severe      int,
@num_variable    int,
@column_id       int,
@sfw_id          int
create table #temp(columnId int, SFWId int, I int, J int, K
int, L int)
declare cluster_col_cursor cursor for
    select distinct cc.ClusterColumnId, cc.SfwId
        from ClusterColumn cc,
            FormalProblem fp,
            Event e
        where e.MemberId = @MemberId
        and e.FormalProblemId = fp.FormalProblemId
        and fp.SFWId = cc.SFWId
        and cc.ClusterColumnType = 'Sfw'
        and e.OnsetSeverity in ('mild', 'moderate', 'severe',
'variable')
open cluster_col_cursor
fetch next from cluster_col_cursor into @column_id, @sfw_id
while @@FETCH_STATUS = 0
begin
    select @num_mild = count(*)
    from Event e,
        FormalProblem fp
    where e.FormalProblemId = fp.FormalProblemId
    and e.MemberId = @MemberId
    and fp.SfwId = @sfw_id
    and e.OnsetSeverity = 'mild'
    select @num_moderate = count(*)
    from Event e,
        FormalProblem fp
    where e.FormalProblemId = fp.FormalProblemId
    and e.MemberId = @MemberId
    and fp.SfwId = @sfw_id
    and e.OnsetSeverity = 'moderate'
    select @num_severe = count(*)
    from Event e,
        FormalProblem fp
    where e.FormalProblemId = fp.FormalProblemId
    and e.MemberId = @MemberId
    and fp.SfwId = @sfw_id
    and e.OnsetSeverity = 'severe'
    select @num_variable = count(*)
    from Event e,
        FormalProblem fp
    where e.FormalProblemId = fp.FormalProblemId
    and e.MemberId = @MemberId
    and fp.SfwId = @sfw_id
    and e.OnsetSeverity = 'variable'
    insert into #temp values(@column_id, @sfw_id, @num_mild,
@num_moderate,
@num_severe, @num_variable)
    fetch next from cluster_col_cursor into @column_id,
@sfw_id
end
close cluster_col_cursor
deallocate cluster_col_cursor
select * from #temp
drop table #temp
GO
</CODE>
```

3. Calculate Similarities from this PDV to Other Members.

This is all done inside the database.

The key code that does this is the bits of sql that follow, essentially it just implements the formula that is in the spec.

```
<CODE lanquage="TSQL">
CREATE PROCEDURE cluster_calculate_similarities_sp
(
    @PdvIdIn    int,
    @Tau        float
)
AS
DECLARE
@PdvIdOut       int
declare cluster_potential_cursor cursor for
    select distinct PdvIdOut
    from cluster_find_potential_pdv_list_view
    where PdvIdIn = @PdvIdIn
    and Tau > @Tau
delete from clusterMetric where pdvId=@pdvIdIn
open cluster_potential_cursor
fetch next from cluster_potential_cursor into @PdvIdOut
while @@FETCH_STATUS = 0
begin
    insert into ClusterMetric(PdvId, PdvId2, AmendDate, Val)
    select @PdvIdIn, @PdvIdOut, getdate( ), sum(cw.weighting *
pd.Val * pd2.Val)
        from PdvDetail pd,
            ClusterWeightings cw,
            PdvDetail pd2
        where cw.ClusterColumnId = pd.ClusterColumnId
        and cw.ClusterColumnId2 = pd2.ClusterColumnId
        and pd.PdvId = @PdvIdIn
        and pd2.PdvId = @PdvIdOut
        and cw.Weighting > @Tau
    fetch next from cluster_potential_cursor into @PdvIdOut
end
close cluster_potential_cursor
deallocate cluster_potential_cursor
GO
</CODE>
```

The above code depends on "cluster_find_potential_pdv_list_view" which is a view used, for speed purposes only, to create virtual subset of all pdvs. (Ie only the pdv-pdv matches where the similarity is >0 get a value inserted)

That view is defined as follows:

```
<CODE language="TSQL">
CREATE PROCEDURE cluster_find_potential_pdv_list_sp
(
    @PdvId  int,
    @Tau    float
)
AS
insert into #potential_pdv
select distinct p2.PdvId
from Pdv p,
    PdvDetail pd,
    ClusterWeightings cw,
    PdvDetail pd2,
    Pdv p2
where pd.PdvId = p.PdvId
and cw.ClusterColumnId = pd.ClusterColumnId
and cw.ClusterColumnId2 = pd2.ClusterColumnId
and pd2.PdvId = p2.PdvId
and p.PdvId = @PdvId
and p2.isDefault='Y'
and cw.Weighting > @Tau
GO
</CODE>
```

4. Find the top N members:

This is pretty simple really . . . Essentially we just iterate through the list of pdvs starting at the most similar until we get to the nth member. At that point we have a value which can be used to select out the speific members via code which says basically "get all members where the similarity value >@calculatedMinValue" to get our N members.

```
<CODE language="TSQL">
CREATE PROCEDURE cluster_find_value_sp
(
    @pdvID INT,
    @n INT
)
AS
declare
@tmpVal as float,
@curVal as float,
@cnt as int
set @curval = 0
set @cnt = 0
--create cursor
DECLARE val_cursor CURSOR FOR
    SELECT   val from clustermetric
    WHERE    pdvid = @pdvID
    ORDER BY val desc
--search for nth value
--search for null values??
OPEN val_cursor
FETCH NEXT FROM val_cursor INTO @curVal
SET @cnt = @cnt + 1
while @@FETCH_STATUS = 0 AND @cnt < @n−1
begin
    FETCH NEXT FROM val_cursor INTO @curVal
    SET @cnt = @cnt + 1
end
print @curVal
CLOSE val_cursor
DEALLOCATE val_cursor
return @curVal
GO
</CODE>
```

The foregoing description of the preferred embodiments of this invention has been presented for purposes of illustration and description. It is not intended to be exhaustive or to limit the invention to the precise form disclosed, and obviously, many modifications and variations are possible, such as different listings (and thus divisions of the semantic plane) of the SFW's, available reportable problems and formal problems, different subject matter than human medical systemic states of being being encoded and mined, etc. Such modifications and variations that may be apparent to persons skilled in the art are intended to be included within the scope of this invention as defined by the accompanying claims.

What is claimed:

1. An interactive medico-health data acquisition, storage and analysis system, comprising:
    a display;
    an interactive medico-health data acquisition interface displayed on the display;
    a memory;
    at least one data processor; and
    a reporting module to report conclusions to a user, wherein, in operation, the interactive medico-health data acquisition interface prompts a user to provide data sufficient to comprise a comprehensive description of his health status;
    wherein the user provided data is simplified so as to remove redundancies and is conceptually organized according to a defined comprehensive medico-health taxonomy;

wherein the data is stored in the memory in a multidimensional data structure having at least three dimensions whose dimensions reflect said taxonomy, said at least three dimensions comprising a systemic field, a functional field and a locational field, and wherein the display of the medico-health data acquisition interface, the prompting of a user, the simplification and organization of data, the storage of data and the reporting to a user is performed by the at least one data processor.

2. The system of claim 1, wherein the interactive medico-health data acquisition interface obtains the data by dynamically posing a plurality of questions to a user.

3. The system of claim 1, wherein the at least one data processor processes the stored data by implementing a clustering generation algorithm to find a set of other users whose multidimensional data structures are within a certain distance of the user's data structure according to a defined distance metric.

4. The system of claim 3, further comprising at least one of storing the cluster for further processing, reporting the members of the cluster to the user, further processing the data associated with the users in the cluster and facilitating on-line communications between the various members of the cluster.

5. The system of claim 4, wherein the at least one data processor further processes the generated cluster to generate useful information for the user.

6. A method of medico-health data acquisition, storage, comparison and analysis, comprising:
providing a first multidimensional data structure comprising a comprehensive description of a health status of a first human being, said multidimensional data structure having at least three dimensions, comprising a systemic field, a functional field and a locational field;
storing said data structure in a database containing a plurality of other multidimensional data structures, each of said multidimensional data structures having at least three dimensions, comprising a systemic field, a functional field and a locational field, and each comprising a comprehensive description of the health status of another human being;
measuring a distance between the first multidimensional data structure and the plurality of other multidimensional data structures using a defined distance metric;
identifying a cluster of closest other multidimensional data structures within the database; and
analyzing the cluster of closest other multidimensional data structures for useful information,
wherein the providing, storing, measuring, identifying and analyzing is performed by a data processor.

7. The method of claim 6, where the number of other multidimensional data structures in the cluster is set dynamically.

8. The method of claim 7, where the number of other multidimensional data structures in the cluster is determined by means of comparing the moving average of the incremental increase in the distance associated with each added multidimensional data structure to a defined threshold.

9. The method of claim 8, wherein the analysis of the cluster generates useful medical information for one of the first human being and the other human beings in the cluster.

10. The method of claim 9, wherein the distance between the multidimensional data structures in the database is a measure of medico-health similarity.

11. A method of expressing a human's comprehensive medico-health state as a multidimensional vector in a hyperspace, comprising:
articulating a substantially comprehensive description of a human's medico-health state using a specialized taxonomy via an interactive medico-health data acquisition interface; and
mapping the articulation to a vector in hyperspace whose components are numbers indicating a measure of a presence or an absence of each of a set of medico-health attributes, said vector having a plurality of components, each of said components having at least three dimensions, comprising a systemic field, a functional field and a locational field;
wherein said articulating and mapping is performed by a data processor, and wherein the components of said vector constitute a orthogonal basis set for specifying a point in the hyperspace.

12. The method of claim 11, wherein the numbers vary between zero and an integer upper bound.

13. A computerized method of comprehensive medico-health data encoding, comprising:
encoding a comprehensive description of a human's health status as a set of numerical values, said values organized in a plurality of records, each record having at least three fields corresponding to a systemic field, a functional field and a locational field;
wherein said encoding is implemented by a data processor in response to data supplied by a user interacting with an automated interactive medico-health data acquisition interface controlled by said data processor that queries a user and elicits said user's responses in terms of a defined comprehensive medico-health taxonomy; and
wherein the set of numerical values comprise the values of categories or qualities that collectively form a orthogonal basis set in a hyperspace.

14. The method of claim 13 wherein each of the values of said categories or qualities itself has M fields or dimensions.

15. The method of claim 14, wherein M equals three.

16. The method of claim 15, wherein each three-dimensional value is a unique coincidence of: a bodily system identifier; an identifier of a medical condition or pertinent fact; and an identifier of anatomical location.

17. A computer storage medium having software code stored thereon, the software code being configured to cause a computer to execute a method for interactive medico-health data acquisition, storage and analysis, the method comprising:
displaying a an interactive medico-health data acquisition interface on a display;
prompting a user to provide data sufficient to comprise a comprehensive description of his health status via the interface;
simplifying the user provided data so as to remove redundancies;
conceptually organize the data according to a defined comprehensive medico-health taxonomy; and
storing the data in a memory in a multidimensional data structure having at least three dimensions whose dimensions reflect said taxonomy, said at least three dimensions comprising a systemic field, a functional field and a locational field.

18. The computer storage medium of claim 17, wherein the prompting of the user to provide data obtains the data by dynamically posing a plurality of questions to the user.

19. The computer storage medium of claim 17, said method further comprising processing the stored data by implementing a clustering generation algorithm to find a set of other users whose multidimensional data structures are within a certain distance of the user's data structure according to a defined distance metric.

20. The computer storage medium of claim 19, said method further comprising at least one of storing the cluster for further processing, reporting the members of the cluster to the user, further processing the data associated with the users in the cluster and facilitating on-line communications between the various members of the cluster.

21. The computer storage medium of claim 20, said method further comprising processing the generated cluster to generate useful information for the user.

* * * * *